US012735476B2

(12) United States Patent
Wang et al.

(10) Patent No.: US 12,735,476 B2
(45) Date of Patent: Sep. 15, 2026

(54) ANTI-GARP/TGF-β ANTIBODIES AND METHODS OF USE

(71) Applicant: SHANGHAI HENLIUS BIOTECH, INC., Shanghai (CN)

(72) Inventors: Jiin-Tarng Wang, Shanghai (CN); Chi-Ling Tseng, Shanghai (CN); Wei-Dong Jiang, Shanghai (CN); Bin Chen, Shanghai (CN); Yao Xu, Shanghai (CN); Jie Gao, Shanghai (CN)

(73) Assignee: SHANGHAI HENLIUS BIOTECH, INC., Shanghai (CN)

( * ) Notice: Subject to any disclaimer, the term of this patent is extended or adjusted under 35 U.S.C. 154(b) by 616 days.

(21) Appl. No.: 18/326,748

(22) Filed: May 31, 2023

(65) Prior Publication Data

US 2023/0340098 A1 Oct. 26, 2023

Related U.S. Application Data

(63) Continuation of application No. PCT/CN2021/132753, filed on Nov. 24, 2021.

(51) Int. Cl.

| | |
|---|---|
| ***C07K 16/22*** | (2006.01) |
| ***A61K 39/00*** | (2006.01) |
| ***A61P 35/00*** | (2006.01) |
| ***C07K 16/28*** | (2006.01) |

(52) U.S. Cl.

CPC .............. *C07K 16/22* (2013.01); *A61P 35/00* (2018.01); *C07K 16/2818* (2013.01); *C07K 16/2863* (2013.01); *A61K 2039/505* (2013.01); *C07K 2317/31* (2013.01); *C07K 2317/52* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 8,840,894 | B2 | 9/2014 | Stitt |
| 2016/0251438 | A1 | 9/2016 | Lucas et al. |
| 2018/0258184 | A1 | 9/2018 | Satoh et al. |
| 2019/0077872 | A1 | 3/2019 | Igawa |
| 2019/0209682 | A1 | 7/2019 | Schurpf et al. |
| 2020/0079840 | A1 | 3/2020 | Datta et al. |

FOREIGN PATENT DOCUMENTS

| | | | |
|---|---|---|---|
| JP | 2016529892 | A | 9/2016 |
| RU | 2710156 | C2 | 12/2019 |
| WO | WO 2015/015003 | A1 | 2/2015 |
| WO | WO 2016/125017 | A1 | 8/2016 |
| WO | 2017051888 | A1 | 3/2017 |
| WO | WO 2018/132427 | A1 | 7/2018 |
| WO | WO 2018/206790 | A1 | 11/2018 |
| WO | WO 2019/075090 | A1 | 4/2019 |
| WO | WO 2019/215151 | A1 | 11/2019 |
| WO | WO 2022/116877 | A1 | 6/2022 |

OTHER PUBLICATIONS

Dondelinger, M. et al.; "Understanding the Significance and Implications of Antibody Numbering and Antigen-Binding Surface/ Residue Definition," Front. Immunol., vol. 9, No. 2278, pp. 1-15 (2018).

Extended European Search Report for Application No. EP 21899910. 0, mailed Jan. 22, 2025 (28 pages).

International Search Report in PCT Application No. PCT/CN2021/ 132753, mailed Feb. 22, 2022 (nine pages).

Written Opinion in PCT Application No. PCT/CN2021/132753, mailed Feb. 22, 2022 (four pages).

Supplementary Partial European Search Report for Application No. EP 21899910.0, mailed Oct. 4, 2024 (24 pages).

Du, Jiamu et al., "Molecular basis of recognition of human osteopontin by 23C3, a potential therapeutic antibody for treatment of rheumatoid arthritis," *J. Mol. Biol.*, vol. 382, No. 4, pp. 835-842 (2008).

Caldas, Cristina et al., "Humanization of the anti-CD18 antibody 6.7: an unexpected effect of a framework residue in binding to antigen," *Molecular Immunology,* vol. 39, No. 15, pp. 941-952 (2003).

Xiang, Jianhua et al. "Modification in framework region I results in a decreased affinity of chimeric anti-tag72 antibody," *Molecular Immunology,* vol. 28, No. 1/2, pp. 141-148 (1991).

Panka, David et al., "Variable region framework differences result in decreased or increased affinity of variant anti-digoxin antibodies," *Immunology,* vol. 85, No. 9, pp. 3080-3084 (1988).

Kunik, Vered et al., "Structural consensus among antibodies defines the antigen binding site," *PLOS Computational Biology,* vol. 8, No. 2, pp. 1-12 (2012).

Rudikoff, Stuart et al., "Single amino acid substitution altering antigen-binding specificity," *Immunology,* vol. 79, No. 6, pp. 1979-1983 (1982).

Winkler, Karsten et al., "Changing the antigen binding specificity by single point mutations of an anti-p24 (HIV-1) antibody," *The Journal of Immunology,* vol. 165, No. 8, pp. 4505-4514 (2000).

*Primary Examiner* — Maher M Haddad
*Assistant Examiner* — Alan Alfano
(74) *Attorney, Agent, or Firm* — Finnegan, Henderson, Farabow, Garrett & Dunner LLP

(57) ABSTRACT

Provided are antibodies and antibody derivatives that bind to GARP (also known as LRRC32 and CPPRDD) and/or GARP/TGFβ complex and methods of using the same. In certain embodiments, an anti-GARP/TGFβ antibody or antibody derivative provided herein can inhibit a TGFβ signal pathway in a target cell.

19 Claims, 14 Drawing Sheets

Specification includes a Sequence Listing.

ANTI-GARP/TGF-β ANTIBODIES AND METHODS OF USE

CROSS-REFERENCE TO RELATED APPLICATIONS

This application is a continuation application of International Application No. PCT/CN2021/132753, filed on Nov. 24, 2021, which claims priority to International Patent Application No. PCT/CN2020/133398 filed on Dec. 2, 2020, the contents of all of which are incorporated herein by reference in its their entirety, and to which priority is claimed.

STATEMENT REGARDING SEQUENCE LISTING

The sequence listing associated with this application is provided in XML format and is hereby incorporated by reference in its entirety into the specification. The name of the XML file containing the sequence listing is FPCH23160069US_SEQUENCE_LISTING.xml, the XML file is 197,839 bytes in size, the XML file was created on Apr. 25, 2023, and the XML file is being submitted via Patent Center with the filing of the application.

FIELD

The present disclosure relates to antibodies and antibody derivatives that bind to GARP/TGFβ complex and methods of using the same.

BACKGROUND

Glycoprotein A repetition predominant (GARP, also known as LRRC32 and CPPRDD) is a transmembrane cell surface docking protein for latent transforming growth factorβ (TGFβ). GARP comprises three domains: a large N-terminal extracellular domain that accounts for about 70% of the protein, a transmembrane domain, and a short C-terminal cytoplasmic tail. GARP plays important roles in multiple tightly regulated steps of TGFβ production, accumulation and activation. Furthermore, GARP/TGFβ complex is expressed on regulatory T lymphocytes (Treg), platelets and a variety of human cancer cells, where it reportedly support cancer cell growth and migration by providing an excessive source of TGFβ, which functions in the tumor microenvironment and promote tumor immune evasion. Given the significant roles of GARP and TGFβ signaling in immune regulation and cancer biology, there is a need in the art for the development of therapeutic molecules and methods targeting GARP/TGFβ signaling for immune therapy and cancer treatment.

SUMMARY OF THE INVENTION

The present disclosure provides isolated monoclonal antibodies and antibody derivatives that bind specifically to GARP/TGFβ complex with high affinity, including monospecific anti-GARP/TGFβ antibodies and multispecific antibodies that binds to GARP/TGFβ complex and one or more additional target. In certain embodiments, an antibody or antibody derivative disclosed herein comprises a full-length antibody that binds to GARP/TGFβ complex. In certain embodiments, an antibody or antibody derivative disclosed herein comprises a scFv that binds to GARP/TGFβ complex. This disclosure further provides methods of making and using antibodies and antibody derivatives disclosed herein and pharmaceutical compositions comprising the same, e.g., for treating diseases and disorders, e.g., cancer. The invention is based, in part, on the discovery of novel antibodies that bind to GARP/TGFβ complex, which can target a tumor cell and/or increase an immune response against a tumor cell.

The present disclosure provides an antibody that binds to GARP/TGFβ complex comprising: a) a heavy chain variable region comprising: (1) a heavy chain variable region CDR-H1 comprising an amino acid sequence of any one of SEQ ID NOs: 1, 11, 21, 31, 41, 51, 61 and 105, or a variant thereof comprising up to about 3 amino acid substitutions; (2) a heavy chain variable region CDR-H2 comprising an amino acid sequence of any one of SEQ ID NOs: 2, 12, 22, 32, 42, 52, 62 and 106, or a variant thereof comprising up to about 3 amino acid substitutions; and (3) a heavy chain variable region CDR-H3 comprising an amino acid sequence of any one of SEQ ID NOs: 3, 13, 23, 33, 43, 53, 63 and 107, or a variant thereof comprising up to about 3 amino acid substitutions; and b) a light chain variable region comprising: (1) a light chain variable region CDR-L1 comprising an amino acid sequence of any one of SEQ ID NOs: 4, 14, 24, 34, 44, 54, 64 and 108, or a variant thereof comprising up to about 3 amino acid substitutions; (2) a light chain variable region CDR-L2 comprising an amino acid sequence of any one of SEQ ID NOs: 5, 15, 25, 35, 45, 55, 65 and 109, or a variant thereof comprising up to about 3 amino acid substitutions; and (3) a light chain variable region CDR-L3 comprising an amino acid sequence of any one of SEQ ID NOs: 6, 16, 26, 36, 46, 56, 66 and 110, or a variant thereof comprising up to about 3 amino acid substitutions.

In certain embodiments, the antibody binds to GARP/TGFβ complex with a KD of $1\times10^{-7}$ M or less. In certain embodiments, the antibody binds to GARP/TGFβ complex with a KD of $1\times10^{-8}$ M or less. In certain embodiments, the antibody binds to GARP/TGFβ complex with a KD of between about $1\times10^{-11}$ M and about $1\times10^{-7}$ M. In certain embodiments, the antibody binds to GARP/TGFβ complex with a KD of between about $1\times10^{-10}$ M and about $5\times10^{-8}$ M.

In certain embodiments, the antibody cross-competes with a reference anti-GARP/TGFβ antibody comprising: a) a heavy chain variable domain (VH) sequence comprising (1) a CDR-H1 comprising the amino acid sequence set forth in SEQ ID NO: 1, (2) a CDR-H2 comprising the amino acid sequence set forth in SEQ ID NO: 2, and (3) a CDR-H3 comprising the amino acid sequence set forth in SEQ ID NO: 3; and a light chain variable domain (VL) sequence comprising (1) a CDR-L1 comprising the amino acid sequence set forth in SEQ ID NO: 4, (2) a CDR-L2 comprising the amino acid sequence set forth in SEQ ID NO: 5, and (3) a CDR-L3 comprising the amino acid sequence set forth in SEQ ID NO: 6; b) a heavy chain variable domain (VH) sequence comprising (1) a CDR-H1 comprising the amino acid sequence set forth in SEQ ID NO: 11, (2) a CDR-H2 comprising the amino acid sequence set forth in SEQ ID NO: 12, and (3) a CDR-H3 comprising the amino acid sequence set forth in SEQ ID NO: 13; and a light chain variable domain (VL) sequence comprising (1) a CDR-L1 comprising the amino acid sequence set forth in SEQ ID NO: 14, (2) a CDR-L2 comprising the amino acid sequence set forth in SEQ ID NO: 15, and (3) a CDR-L3 comprising the amino acid sequence set forth in SEQ ID NO: 16; c) a heavy chain variable domain (VH) sequence comprising (1) a CDR-H1 comprising the amino acid sequence set forth in SEQ ID NO: 21, (2) a CDR-H2 comprising the amino acid sequence set forth in SEQ ID NO: 22, and (3) a CDR-H3 comprising the amino acid sequence set forth in SEQ ID NO: 23; and a light chain variable domain (VL) sequence comprising (1) a CDR-L1 comprising the amino acid sequence set forth in SEQ ID NO: 24, (2) a CDR-L2 comprising the amino acid sequence set forth in SEQ ID NO: 25, and (3) a CDR-L3 comprising the amino acid sequence set forth in SEQ ID NO: 26; d) a heavy chain variable domain (VH) sequence comprising (1) a CDR-H1 comprising the amino acid sequence set forth in SEQ ID NO: 31, (2) a CDR-H2 comprising the amino acid sequence set forth in SEQ ID NO: 32, and (3) a CDR-H3 comprising the amino acid sequence set forth in SEQ ID NO: 33; and a light chain variable domain (VL) sequence comprising (1) a CDR-L1 comprising the amino acid sequence set forth in SEQ ID NO: 34, (2) a CDR-L2 comprising the amino acid sequence set forth in SEQ ID NO: 35, and (3) a CDR-L3 comprising the amino acid sequence set forth in SEQ ID NO: 36; e) a heavy chain variable domain (VH) sequence comprising (1) a CDR-H1 comprising the amino acid sequence set forth in SEQ ID NO: 41, (2) a CDR-H2 comprising the amino acid sequence set forth in SEQ ID NO: 42, and (3) a CDR-H3 comprising the amino acid sequence set forth in SEQ ID NO: 43; and a light chain variable domain (VL) sequence comprising (1) a CDR-L1 comprising the amino acid sequence set forth in SEQ ID NO: 44, (2) a CDR-L2 comprising the amino acid sequence set forth in SEQ ID NO: 45, and (3) a CDR-L3 comprising the amino acid sequence set forth in SEQ ID NO: 46; f) a heavy chain variable domain (VH) sequence comprising (1) a CDR-H1 comprising the amino acid sequence set forth in SEQ ID NO: 51, (2) a CDR-H2 comprising the amino acid sequence set forth in SEQ ID NO: 52, and (3) a CDR-H3 comprising the amino acid sequence set forth in SEQ ID NO: 53; and a light chain variable domain (VL) sequence comprising (1) a CDR-L1 comprising the amino acid sequence set forth in SEQ ID NO: 54, (2) a CDR-L2 comprising the amino acid sequence set forth in SEQ ID NO: 55, and (3) a CDR-L3 comprising the amino acid sequence set forth in SEQ ID NO: 56; g) a heavy chain variable domain (VH) sequence comprising (1) a CDR-H1 comprising the amino acid sequence set forth in SEQ ID NO: 61, (2) a CDR-H2 comprising the amino acid sequence set forth in SEQ ID NO: 62, and (3) a CDR-H3 comprising the amino acid sequence set forth in SEQ ID NO: 63; and a light chain variable domain (VL) sequence comprising (1) a CDR-L1 comprising the amino acid sequence set forth in SEQ ID NO: 64, (2) a CDR-L2 comprising the amino acid sequence set forth in SEQ ID NO: 65, and (3) a CDR-L3 comprising the amino acid sequence set forth in SEQ ID NO: 66; or h) a heavy chain variable domain (VH) sequence comprising (1) a CDR-H1 comprising the amino acid sequence set forth in SEQ ID NO: 105, (2) a CDR-H2 comprising the amino acid sequence set forth in SEQ ID NO: 106, and (3) a CDR-H3 comprising the amino acid sequence set forth in SEQ ID NO: 107; and a light chain variable domain (VL) sequence comprising (1) a CDR-L1 comprising the amino acid sequence set forth in SEQ ID NO: 108, (2) a CDR-L2 comprising the amino acid sequence set forth in SEQ ID NO: 109, and (3) a CDR-L3 comprising the amino acid sequence set forth in SEQ ID NO: 110.

In certain embodiments, the antibody comprises: a) a heavy chain variable region that comprises a CDR-H1 domain, a CDR-H2 domain and a CDR-H3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence selected from the group consisting of SEQ ID NOs: 7, 17, 27, 37, 47, 57, 67, 85, 89, 93, 97, 101 and 111; and b) a light chain variable region that comprises a CDR-L1 domain, a CDR-L2 domain and a CDR-L3 domain, wherein the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence selected from the group consisting of SEQ ID NOs: 8, 18, 28, 38, 48, 58, 68, 83, 84, 86, 90, 94, 98, 102 and 112.

In certain embodiments, the antibody comprises a heavy chain variable domain (VH) sequence comprising (1) a CDR-H1 comprising the amino acid sequence set forth in SEQ ID NO: 1, (2) a CDR-H2 comprising the amino acid sequence set forth in SEQ ID NO: 2, and (3) a CDR-H3 comprising the amino acid sequence set forth in SEQ ID NO: 3; and a light chain variable domain (VL) sequence comprising (1) a CDR-L1 comprising the amino acid sequence set forth in SEQ ID NO: 4, (2) a CDR-L2 comprising the amino acid sequence set forth in SEQ ID NO: 5, and (3) a CDR-L3 comprising the amino acid sequence set forth in SEQ ID NO: 6. In certain embodiments, the antibody comprises a heavy chain variable domain (VH) sequence comprising (1) a CDR-H1 comprising the amino acid sequence set forth in SEQ ID NO: 11, (2) a CDR-H2 comprising the amino acid sequence set forth in SEQ ID NO: 12, and (3) a CDR-H3 comprising the amino acid sequence set forth in SEQ ID NO: 13; and a light chain variable domain (VL) sequence comprising (1) a CDR-L1 comprising the amino acid sequence set forth in SEQ ID NO: 14, (2) a CDR-L2 comprising the amino acid sequence set forth in SEQ ID NO: 15, and (3) a CDR-L3 comprising the amino acid sequence set forth in SEQ ID NO: 16. In certain embodiments, the antibody comprises a heavy chain variable domain (VH) sequence comprising (1) a CDR-H1 comprising the amino acid sequence set forth in SEQ ID NO: 21, (2) a CDR-H2 comprising the amino acid sequence set forth in SEQ ID NO: 22, and (3) a CDR-H3 comprising the amino acid sequence set forth in SEQ ID NO: 23; and a light chain variable domain (VL) sequence comprising (1) a CDR-L1 comprising the amino acid sequence set forth in SEQ ID NO: 24, (2) a CDR-L2 comprising the amino acid sequence set forth in SEQ ID NO: 25, and (3) a CDR-L3 comprising the amino acid sequence set forth in SEQ ID NO: 26. In certain embodiments, the antibody comprises a heavy chain variable domain (VH) sequence comprising (1) a CDR-H1 comprising the amino acid sequence set forth in SEQ ID NO: 31, (2) a CDR-H2 comprising the amino acid sequence set forth in SEQ ID NO: 32, and (3) a CDR-H3 comprising the amino acid sequence set forth in SEQ ID NO: 33; and a light chain variable domain (VL) sequence comprising (1) a CDR-L1 comprising the amino acid sequence set forth in SEQ ID NO: 34, (2) a CDR-L2 comprising the amino acid sequence set forth in SEQ ID NO: 35, and (3) a CDR-L3 comprising the amino acid sequence set forth in SEQ ID NO: 36. In certain embodiments, the antibody comprises a heavy chain variable domain (VH) sequence comprising (1) a CDR-H1 comprising the amino acid sequence set forth in SEQ ID NO: 41, (2) a CDR-H2 comprising the amino acid sequence set forth in SEQ ID NO: 42, and (3) a CDR-H3 comprising the amino acid sequence set forth in SEQ ID NO: 43; and a light chain variable domain (VL) sequence comprising (1) a CDR-L1 comprising the amino acid sequence set forth in SEQ ID NO: 44, (2) a CDR-L2 comprising the amino acid sequence set forth in SEQ ID NO: 45, and (3) a CDR-L3 comprising the amino acid sequence set forth in SEQ ID NO: 46. In certain embodiments, the antibody comprises a heavy chain variable domain (VH) sequence comprising (1) a CDR-H1 comprising the amino acid sequence set forth in SEQ ID NO: 51, (2) a CDR-H2 comprising the amino acid sequence set forth in SEQ ID NO: 52, and (3) a CDR-H3 comprising the amino acid sequence set forth in SEQ ID NO: 53; and a light chain variable domain (VL) sequence comprising (1) a CDR-L1 comprising the amino acid sequence set forth in SEQ ID NO: 54, (2) a CDR-L2 comprising the amino acid sequence set forth in SEQ ID NO: 55, and (3) a CDR-L3 comprising the amino acid sequence set forth in SEQ ID NO: 56. In certain embodiments, the antibody comprises a heavy chain variable domain (VH) sequence comprising (1) a CDR-H1 comprising the amino acid sequence set forth in SEQ ID NO: 61, (2) a CDR-H2 comprising the amino acid sequence set forth in SEQ ID NO: 62, and (3) a CDR-H3 comprising the amino acid sequence set forth in SEQ ID NO: 63; and a light chain variable domain (VL) sequence comprising (1) a CDR-L1 comprising the amino acid sequence set forth in SEQ ID NO: 64, (2) a CDR-L2 comprising the amino acid sequence set forth in SEQ ID NO: 65, and (3) a CDR-L3 comprising the amino acid sequence set forth in SEQ ID NO: 66. In certain embodiments, the antibody comprises a heavy chain variable domain (VH) sequence comprising (1) a CDR-H1 comprising the amino acid sequence set forth in SEQ ID NO: 105, (2) a CDR-H2 comprising the amino acid sequence set forth in SEQ ID NO: 106, and (3) a CDR-H3 comprising the amino acid sequence set forth in SEQ ID NO: 107; and a light chain variable domain (VL) sequence comprising (1) a CDR-L1 comprising the amino acid sequence set forth in SEQ ID NO: 108, (2) a CDR-L2 comprising the amino acid sequence set forth in SEQ ID NO: 109, and (3) a CDR-L3 comprising the amino acid sequence set forth in SEQ ID NO: 110.

In certain embodiments, the antibody comprises a heavy chain variable region comprising the amino acid sequence set forth in SEQ ID NO: 7, and a light chain variable region comprising the amino acid sequence set forth in SEQ ID NO: 8. In certain embodiments, the antibody comprises a heavy chain variable region comprising the amino acid sequence set forth in SEQ ID NO: 17, and a light chain variable region comprising the amino acid sequence set forth in SEQ ID NO: 18. In certain embodiments, the antibody comprises a heavy chain variable region comprising the amino acid sequence set forth in SEQ ID NO: 27, and a light chain variable region comprising the amino acid sequence set forth in SEQ ID NO: 28. In certain embodiments, the antibody comprises a heavy chain variable region comprising the amino acid sequence set forth in SEQ ID NO: 37, and a light chain variable region comprising the amino acid sequence set forth in SEQ ID NO: 38. In certain embodiments, the antibody comprises a heavy chain variable region comprising the amino acid sequence set forth in SEQ ID NO: 37, and a light chain variable region comprising the amino acid sequence set forth in SEQ ID NO: 83. In certain embodiments, the antibody comprises a heavy chain variable region comprising the amino acid sequence set forth in SEQ ID NO: 47, and a light chain variable region comprising the amino acid sequence set forth in SEQ ID NO: 48. In certain embodiments, the antibody comprises a heavy chain variable region comprising the amino acid sequence set forth in SEQ ID NO: 47, and a light chain variable region comprising the amino acid sequence set forth in SEQ ID NO: 84. In certain embodiments, the antibody comprises a heavy chain variable region comprising the amino acid sequence set forth in SEQ ID NO: 57, and a light chain variable region comprising the amino acid sequence set forth in SEQ ID NO: 58. In certain embodiments, the antibody comprises a heavy chain variable region comprising the amino acid sequence set forth in SEQ ID NO: 67, and a light chain variable region comprising the amino acid sequence set forth in SEQ ID NO: 68. In certain embodiments, the antibody comprises a heavy chain variable region comprising the amino acid sequence set forth in SEQ ID NO: 85, and a light chain variable region comprising the amino acid sequence set forth in SEQ ID NO: 86. In certain embodiments, the antibody comprises a heavy chain variable region comprising the amino acid sequence set forth in SEQ ID NO: 89, and a light chain variable region comprising the amino acid sequence set forth in SEQ ID NO: 90. In certain embodiments, the antibody comprises a heavy chain variable region comprising the amino acid sequence set forth in SEQ ID NO: 93, and a light chain variable region comprising the amino acid sequence set forth in SEQ ID NO: 94. In certain embodiments, the antibody comprises a heavy chain variable region comprising the amino acid sequence set forth in SEQ ID NO: 97, and a light chain variable region comprising the amino acid sequence set forth in SEQ ID NO: 98. In certain embodiments, the antibody comprises a heavy chain variable region comprising the amino acid sequence set forth in SEQ ID NO: 101, and a light chain variable region comprising the amino acid sequence set forth in SEQ ID NO: 102. In certain embodiments, the antibody comprises a heavy chain variable region comprising the amino acid sequence set forth in SEQ ID NO: 111, and a light chain variable region comprising the amino acid sequence set forth in SEQ ID NO: 112.

In certain embodiments, the antibody comprises a human framework. In certain embodiments, the antibody is a human antibody. In certain embodiments, the antibody is a humanized antibody. In certain embodiments, the antibody comprises a full-length immunoglobulin, a single-chain Fv (scFv) fragment, a Fab fragment, a Fab' fragment, a F(ab')2, a Fv fragment, a disulfide stabilized Fv fragment (dsFv), a (dsFv)2, a Fv-Fc fusion, a scFv-Fc fusion, a scFv-Fv fusion, a diabody, a tribody, a tetrabody or any combination thereof.

In certain embodiments, the antibody comprises a Fc region. In certain embodiments, the Fc region comprises a human Fc region. In certain embodiments, the Fc region comprises a Fc region selected from the group consisting of the Fc regions of IgG, IgA, IgD, IgE and IgM.

In certain embodiments, the Fc region comprises a Fc region selected from the group consisting of the Fc regions of IgG1, IgG2, IgG3 and IgG4. In certain embodiments, the Fc region comprises an IgG1 Fc region. In certain embodiments, the Fc region comprises an IgG4 Fc region. In certain embodiments, the antibody binds to human GARP/TGFβ complex. In certain embodiments, the antibody binds to cynomolgus GARP/TGFβ complex. In certain embodiments, the antibody binds to human GARP/TGFβ complex, cynomolgus GARP/TGFβ complex and mouse GARP/TGFβ complex. In certain embodiments, the Fc region comprises a C-terminal lysine. In certain embodiments, the Fc region comprises a deletion of a C-terminal lysine.

In certain embodiments, the antibody is comprised in a multispecific antibody, e.g., a bispecific antibody, wherein the multispecific antibody comprises a second antibody moiety that specifically binds to a second antigen. In certain embodiments, the second antigen is a tumor associated antigen. In certain embodiments, the tumor associated antigen is selected from the group consisting of Her-2, EGFR, PDL1, MSLN, c-Met, B Cell Maturation Antigen (BCMA), carbonic anhydrase IX (CA1X), carcinoembryonic antigen (CEA), CD5, CD7, CD10, CD19, CD20, CD22, CD30, CD33, CD34, CD38, CD41, CD44, CD47, CD49f, CD56, CD74, CD123, CD133, CD138, CD276 (B7H3), epithelial glycoprotein (EGP2), trophoblast cell-surface antigen 2 (TROP-2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human telomerase reverse transcriptase (hTERT), kinase insert domain receptor (KDR), Lewis A (CA 1.9.9), Lewis Y (LeY), Glypican-3 (GPC3), L1 cell adhesion molecule (L1CAM), Mucin 16 (Muc-16), Mucin 1 (Muc-1), NG2D ligands, oncofetal antigen (h5T4), prostate stem cell antigen (PSCA), prostate-specific membrane antigen (PSMA), tumor-associated glycoprotein 72 (TAG-72), Claudin18.2 (CLDN18.2), vascular endothelial growth factor R2 (VEGF-R2), Wilms tumor protein (WT-1), type 1 tyrosine-protein kinase transmembrane receptor (ROR1), PVR, PVRL2, and any combination thereof. In certain embodiments, the second antigen is an immune checkpoint regulator. In certain embodiments, the immune checkpoint regulator is selected from the group consisting of TIGIT, PD1, CTLA4, LAG-3, 2B4, BTLA and any combination thereof. In certain embodiments, the second antigen is an immune costimulatory molecule or a subunit of a T cell receptor/CD3 complex. In certain embodiments, the immune costimulatory molecule is selected from the group consisting of CD28, ICOS, CD27, 4-1BB, OX40 and CD40 and any combination thereof. In certain embodiments, the subunit of the T cell receptor/CD3 complex is selected from the group consisting of CD3γ, CD3δ, CD3ε and any combination thereof.

The present disclosure provides an immunoconjugate comprising any antibody disclosed herein linked to a therapeutic agent or a label. In certain embodiments, the therapeutic agent is a cytotoxin or a radioactive isotope. In certain embodiments, the label is selected from the group consisting of a radioisotope, a fluorescent dye and an enzyme.

The present disclosure provides an antigen-recognizing receptor comprising an extracellular antigen-binding domain that comprises an antibody disclosed herein. In certain embodiments, the antigen-recognizing receptor isa Chimeric Antigen Receptor (CAR) or a recombinant T cell Receptor. In certain embodiments, the antigen-recognizing receptor isa CAR. In certain embodiments, the antibody is a scFv or a Fab.

The present disclosure provides an immunoresponsive cell comprising an antigen-recognizing receptor disclosed herein. In certain embodiments, the immunoresponsive cell is selected from the group consisting of a T cell, a Natural Killer (NK) cell, a cytotoxic T lymphocyte (CTL), a regulatory T cell, a Natural Killer T (NKT) cell and a myeloid cell. In certain embodiments, the immunoresponsive cell is a T cell.

The present disclosure further provides pharmaceutical compositions. In certain embodiments, the pharmaceutical composition comprises a) an antibody, an immunoconjugate or an immunoresponsive cell disclosed herein, and b) a pharmaceutically acceptable carrier.

The present disclosure further provides one or more nucleic acid encoding any antibodies disclosed herein, one or more vector comprising any nucleic acid disclosed herein, and host cells comprising any nucleic acid or any vector disclosed herein.

The present disclosure provides methods for preparing an antibody disclosed herein. In certain embodiments, the method comprises expressing an antibody in a host cell disclosed herein and isolating the antibody from the host cell.

The present disclosure further provides methods of reducing tumor burden in a subject. In certain embodiments, the method comprises administering to the subject an effective amount of an antibody, an immunoconjugate, or a pharmaceutical composition disclosed herein.

In certain embodiments, the method reduces the number of tumor cells. In certain embodiments, the method reduces tumor size. In certain embodiments, the method eradicates the tumor in the subject. In certain embodiments, the tumor exhibits high microsatellite instability (MSI). In certain embodiments, the tumor is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer and a combination thereof.

The present disclosure further provides methods of treating and/or preventing cancer in a subject. In certain embodiments, the method comprises administering to the subject an effective amount of an antibody, an immunoconjugate, or a pharmaceutical composition disclosed herein.

The present disclosure further provides methods of lengthening survival of a subject having cancer. In certain embodiments, the method comprises administering to the subject an effective amount of an antibody, an immunoconjugate, or a pharmaceutical composition disclosed herein.

In certain embodiments, the cancer exhibits high microsatellite instability (MSI). In certain embodiments, the cancer is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer and a combination thereof.

The present disclosure provides any antibodies disclosed herein for use as a medicament. The present disclosure further provides any antibodies disclosed herein for use in treating cancer. The present disclosure further provides pharmaceutical compositions disclosed herein for use as a medicament. The present disclosure further provides pharmaceutical compositions disclosed herein for use in treating cancer. In certain embodiments, the cancer exhibits high microsatellite instability (MSI). In certain embodiments, the cancer is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer and a combination thereof.

The present disclosure provides kits comprising an antibody, an immunoconjugate, a pharmaceutical composition, a nucleic acid, a vector or an immunoresponsive cell disclosed herein. In certain embodiments, the kit comprise a written instruction for treating and/or preventing a neoplasm.

The present disclosure further provides a method of treating cancer in a subject comprising administering to the subject an effective amount of an anti-GARP/TGFβ antibody and an anti-PD1 antibody. In certain embodiments, the anti-GARP/TGFβ antibody is an anti-GARP/TGFβ antibody disclosed herein. In certain embodiments, the cancer exhibits high microsatellite instability (MSI). In certain embodiments, the cancer is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer and a combination thereof. In certain embodiments, the anti-GARP/TGFβ antibody and the anti-PD1 antibody are administered concurrently or sequentially. In certain embodiments, the anti-GARP/TGFβ antibody and the anti-PD1 antibody are administered concurrently. In certain embodiments, one or more doses of the anti-PD1 antibody is administered prior to administering the anti-GARP/TGFβ antibody. In certain embodiments, the subject received a complete course of the anti-PD1 antibody therapy prior to administration of the anti-GARP/TGFβ antibody. In certain embodiments, the anti-GARP/TGFβ antibody is administered during a second course of the anti-PD1 antibody therapy. In certain embodiments, the subject received at least one, at least two, at least three, or at least four doses of the anti-PD1 antibody prior to administration of the anti-GARP/TGFβ antibody. In certain embodiments, at least one dose of the anti-PD1 antibody is administered concurrently with the anti-GARP/TGFβ inhibitor. In certain embodiments, one or more doses of the anti-GARP/TGFβ antibody are administered prior to administering the anti-PD1 antibody. In certain embodiments, the subject received at least two, at least three, at least three, or at least four doses of the anti-GARP/TGFβ antibody prior to administration of the anti-PD1 antibody. In certain embodiments, at least one dose of the anti-GARP/TGFβ antibody is administered concurrently with the anti-PD1 antibody. In certain embodiments, the anti-GARP/TGFβ antibody and the anti-PD1 antibody are administered once every 1, 2, 3, 4, or 5 weeks. In certain embodiments, the cancer is recurrent or progressive after a therapy selected from the group consisting of surgery, chemotherapy, radiation therapy and any combination thereof.

BRIEF DESCRIPTION OF THE FIGURES

FIG. 21A depicts tumor growth curves under the treatment of indicated anti-GARP/TGFβ antibodies and control. FIG. 21B depicts Treg cell population in the blood of the mice in each treatment group. FIG. 21C depicts Treg cell population in the spleens of the mice in each treatment group.

DETAILED DESCRIPTION

Figure 1A:
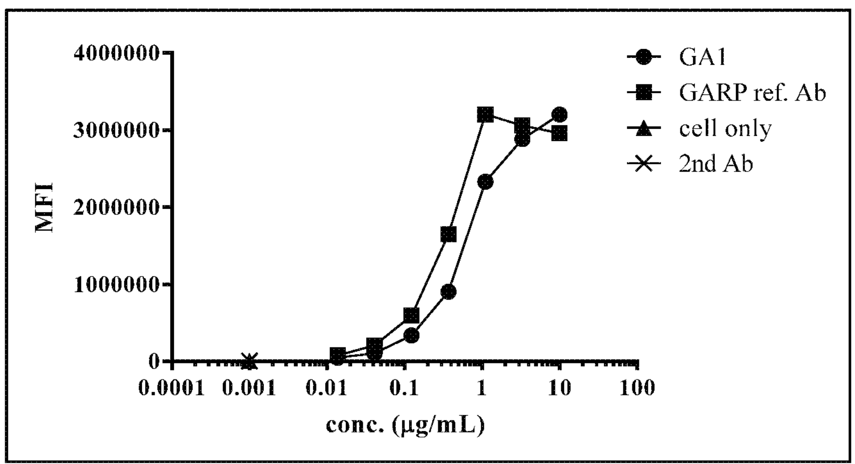
FIGS. 1A-1E depict GARP/latent TGFβ1 binding of selected antibody clone. Antibody clone GA1 was selected from a naïve human Fab phage library and was tested for its binding ability to human GARP/latent TGFβ1 transfected CHO-S cells (1A), cynomolgus GARP/latent TGFβ1 transfected CHO-S cells (1B), mouse GARP/latent TGFβ1 transfected CHO-S cells (1C), thrombin-activated human platelets (1D), and anti-CD3/CD28 beads-activated human Treg (1E) by flow cytometry. GARP ref. Ab, an ABBV-151 analog, was used as a positive control. Isotype control (bevacizumab) was used as a negative control.
Figure 1B:
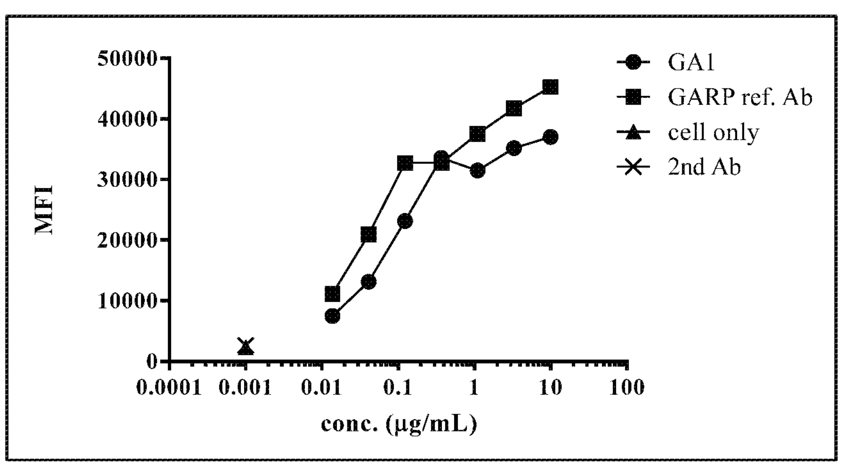

The present disclosure provides isolated monoclonal antibodies and antibody derivatives that bind specifically to GARP/TGFβ complex with high affinity, including monospecific anti-GARP/TGFβ antibodies and multispecific antibodies that binds to GARP/TGFβ complex and one or more additional target. In certain embodiments, an antibody or antibody derivative disclosed herein comprises a full-length antibody that binds to GARP/TGFβ complex. In certain embodiments, an antibody or antibody derivative disclosed herein comprises a scFv that binds to GARP/TGFβ complex. This disclosure further provides methods of making and using antibodies and antibody derivatives disclosed herein and pharmaceutical compositions comprising the same, e.g., for treating diseases and disorders, e.g., cancer. The invention is based, in part, on the discovery of novel antibodies that bind to GARP/TGFβ complex, which can target a tumor cell and/or increase an immune response against a tumor cell.

For clarity and not by way of limitation the detailed description of the presently disclosed subject matter is divided into the following subsections:

1. Definitions;
2. Antibodies and antibody derivatives;
3. Methods of use;
4. Pharmaceutical formulations; and
5. Articles of manufacture.

1. Definitions

The term "antibody" as referred to herein includes full-length antibodies and any antigen-binding fragment thereof (i.e., antibody fragment). An "antibody" can be a standalone molecule or a portion of an antibody derivative. Exemplary antibody derivatives include, but are not limited to, a multifunctional antibody, e.g., a multispecific antibody (e.g., a bispecific antibody), an antigen-recognizing receptor (e.g., a chimeric antigen receptor), an antibody conjugate comprising an additional proteinaceous or non-proteinaceous moiety (e.g., an antibody-drug conjugate or a polymer-coated antibody), and other multifuctional molecules comprising an antibody.

A "full-length antibody", "intact antibody" and "whole antibody" refers to an antibody similar to a native antibody structure or having heavy chains that contain an Fc region as defined herein. In certain embodiments, a full-length antibody comprises two heavy chains and two light chains. In certain embodiments, the variable regions of the light and heavy chains are responsible for antigen binding. The variable regions of a heavy chain and a light chain may be referred to as "VH" and "VL", respectively. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by well-known conventions, e.g., the conventions of Kabat, Chothia, MacCallum, IMGT and AHo as described below. The three CDRs of the heavy or light chains are interposed between flanking stretches known as framework regions (FRs), which are more conserved than the CDRs and form a scaffold to support the hypervariable loops. The constant regions of the heavy and light chains are not involved in antigen binding but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 ($\gamma^4$ heavy chain), IgAQ1 (α1 heavy chain), or IgA2 (α2 heavy chain). In certain embodiments, a full-length antibody is glycosylated. In certain embodiments, a full-length antibody comprises a glycan linked to its Fc region. In certain embodiments, a full-length antibody comprises a branched glycan.

The term "antigen-binding portion", "antibody fragment" and "antibody portion" of an antibody, as used herein, refers to one or more fragments of an antibody that retain the ability to specifically bind to an antigen. It has been shown that the antigen-binding function of an antibody can be performed by fragments of a full-length antibody. Examples of antibody fragments include but are not limited to Fv, Fab, Fab', Fab'-SH, F(ab')2, diabodies, linear antibodies, single-chain antibody molecules (e.g., scFv and scFv-Fc), a single domain antibody, a VHH, a VHH-Fc, a nanobody, a domain antibody, a bivalent domain antibody, or any other fragment or combination thereof of an antibody that binds to an antigen. A "VHH" refers to a single domain antibody isolated from a camelid animal. In certain embodiments, a VHH comprises a variable region of a heavy chain of a camelid heavy chain antibody. In certain embodiments, a VHH has a size of no more than about 25 kDa. In certain embodiments, a VHH has a size of no more than about 20 kDa. In certain embodiments, a VHH has a size of no more than about 15 kDa.

An "antibody that cross-competes for binding" with a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is described in Antibodies, Harlow and Lane (Cold Spring Harbor Press, Cold Spring Harbor, NY).

"Fv" is a minimum antibody fragment which contains a complete antigen-recognition and -binding site. This fragment consists of a dimer of one heavy- and one light-chain variable region in tight, non-covalent association. From the folding of these two domains emanate six hypervariable loops (3 loops in each of the heavy and light chains) that contribute the amino acid residues to antigen binding and confer antigen binding specificity to the antibody. However, even a single variable domain (or half of a Fv comprising only three CDRs specific for an antigen) can recognize and bind to an antigen, although sometimes at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

An "acceptor human framework" or "human framework" for the purposes herein is a framework comprising the amino acid sequence of a light chain variable domain (VL) framework or a heavy chain variable domain (VH) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In certain embodiments, the number of amino acid changes are 10 or less, 9 or less, 8 or less, 7 or less, 6 or less, 5 or less, 4 or less, 3 or less, or 2 or less. In certain embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Specific illustrative and exemplary embodiments for measuring binding affinity are described in the following.

An "affinity matured" antibody refers to an antibody with one or more alterations in one or more CDRs or hypervariable regions (HVRs), compared to a parent antibody which does not possess such alterations, which alterations provide improved affinity of the antibody for antigen.

"GARP", "GARP protein" or "GARP polypeptide" as used herein, refers to any GARP polypeptide from any vertebrate source, including mammals such as primates (e.g., humans and cynomolgus monkeys), or any fragment thereof, and may optionally comprise up to one, up to two, up to three, up to four, up to five, up to six, up to seven, up to eight, up to nine or up to ten amino acid substitutions, additions and/or deletions. The term encompasses full-length, unprocessed GARP as well as any form of GARP that results from processing in the cell. The term also encompasses naturally occurring variants of GARP, e.g., splice variants or allelic variants. In certain embodiments, a GARP polypeptide comprises or has an amino acid sequence that is at least about 80%, at least about 85%, at least about 90%, at least about 95%, at least about 96%, at least about 97%, at least about 98%, at least about 99% or at least about 100% homologous or identical to the sequence having a NCBI Reference Nos: NP_001122394.1, NP_001357116.1, NP 001357117.1, NP 001357118.1, NP_001357119.1, NP_001357120.1, or NP_005503.1 (homology herein may be determined using standard software such as BLAST or FASTA). In certain embodiments, the GARP polypeptide comprises or has an amino acid sequence that is the entirety or a consecutive portion of SEQ ID NO: 85. In certain embodiments, a GARP protein is in a GARP/TGFβ complex. In certain embodiments, a GARP protein is not in a GARP/TGFβ complex, e.g., an isolated GARP protein.

The term "ECD of GARP" refers to an extracellular domain of GARP. In certain embodiments, the extracellular domain of GARP is a N-terminal extracellular domain of GARP. In certain embodiments, the N-terminal ECD of an exemplary GARP polypeptide can comprise the amino acid sequence set forth in SEQ ID NO: 86.

The terms "anti-GARP/TGFβ antibody" and "an antibody that binds to GARP/TGFβ complex" refer to an antibody that is capable of binding to GARP/TGFβ complex with sufficient affinity such that the antibody is useful as a diagnostic and/or therapeutic agent for targeting GARP/TGFβ complex. In one embodiment, the extent of binding of an anti-GARP/TGFβ antibody to an unrelated, non-GARP/TGFβ protein is less than about 10% of the binding of the antibody to GARP/TGFβ complex as measured, e.g., by a BIACORE® surface plasmon resonance assay. In certain embodiments, an antibody that binds to GARP/TGFβ complex has a dissociation constant (KD) of <about 1 μM, <about 100 nM, <about 10 nM, <about 1 nM, <about 0.1 nM, <about 0.01 nM, or <about 0.001 nM (e.g., $10^{-8}$ M or less, e.g., from $10^{-1}$ M to $10^{-12}$ M, e.g., from $10^{-9}$ M to $10^{-1}$ M). In certain embodiments, an anti-GARP/TGFβ antibody binds to an epitope of a GARP/TGFβ complex that is conserved among the GARP/TGFβ complex from different species. In certain embodiments, an anti-GARP/TGFβ antibody binds to an epitope on a GARP protein that is in the ECD of the protein. In certain embodiments, an anti-GARP/TGFβ antibody binds to a GARP protein in a GARP/TGFβ complex. In certain embodiments, an anti-GARP/TGFβ antibody binds to a GARP protein that is not in a GARP/TGFβ complex, e.g., an isolated GARP protein. In certain embodiments, an anti-GARP/TGFβ antibody does not bind to a GARP protein that is not a GARP/TGFβ complex.

The term "chimeric" antibody refers to an antibody in which a portion of the heavy and/or light chain is derived from a particular source or species, while the remainder of the heavy and/or light chain is derived from a different source or species. In certain embodiments, a chimeric antibody disclosed herein comprises a camelid heavy chain variable region and a human Fc region.

As used herein, the term "CDR" or "complementarity determining region" is intended to mean the non-contiguous antigen combining sites within the variable region of a heavy chain and/or a light chain. These particular regions have been described by Kabat et al., J. Biol. Chem. 252: 6609-6616 (1977); Kabat et al., U.S. Dept. of Health and Human Services, "Sequences of proteins of immunological interest" (1991); Chothia et al., J. Mol. Biol. 196:901-917 (1987); Al-Lazikani B. et al., J. Mol. Biol., 273: 927-948 (1997); MacCallum et al., J. Mol. Biol. 262:732-745 (1996); Abhinandan and Martin, Mol. Immunol., 45: 3832-3839 (2008); Lefranc M. P. et al., Dev. Comp. Immunol., 27: 55-77 (2003); and Honegger and Plückthun, J. Mol. Biol., 309:657-670 (2001), where the definitions include overlapping or subsets of amino acid residues when compared against each other. Nevertheless, application of any one of the definitions to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, Mol. Immunol., 45: 3832-3839 (2008); Ehrenmann F. et al., Nucleic Acids Res., 38: D301-D307 (2010); and Adolf-Bryfogle J. et al., Nucleic Acids Res., 43: D432-D438 (2015). The contents of the references cited in this paragraph are incorporated herein by reference in their entireties for use in the present application and for possible inclusion in one or more claims herein.

TABLE 1

| CDR definitions | | | | | |
|---|---|---|---|---|---|
| | Kabat[1] | Chothia[2] | MacCallum[3] | IMGT[4] | AHo[5] |
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

TABLE 1-continued

| CDR definitions | | | | | |
|---|---|---|---|---|---|
| | Kabat[1] | Chothia[2] | MacCallum[3] | IMGT[4] | AHo[5] |

[1]Residue numbering follows the nomenclature of Kabat et al., supra.
[2]Residue numbering follows the nomenclature of Chothia et al., supra.
[3]Residue numbering follows the nomenclature of MacCallum et al., supra.
[4]Residue numbering follows the nomenclature of Lefranc et al., supra.
[5]Residue numbering follows the nomenclature of Honegger and Plückthun, supra.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or CDR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

In certain embodiments, the amino acid residues which encompass the CDRs of a single domain antibody is defined according to the IMGT nomenclature in Lefranc et al., supra. In certain embodiments, the amino acid residues which encompass the CDRs of a full-length antibody or a scFv is defined according to the Kabat nomenclature in Kabat et al., supra. In certain embodiments, the numbering of the residues in an immunoglobulin heavy chain, e.g., in an Fc region, is that of the EU index as in Kabat et al., supra. The "EU index as in Kabat" refers to the residue numbering of the human IgG1 EU antibody.

"Framework" or "FR" refers to residues are those variable-domain residues other than the CDR residues as herein defined.

A "humanized" antibody refers to a chimeric antibody comprising amino acid residues from non-human CDRs/HVRs and amino acid residues from human FRs. In certain embodiments, a humanized antibody will comprise substantially all of at least one, and typically two, variable domains, in which all or substantially all of the HVRs/CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985);

Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., Nucleic Acids Research 32(5):1792-1797, 2004; Edgar, R. C., BMC Bioinformatics 5(1):113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the $C_L$domain of the light chain.

The "light chains" of antibodies (e.g., immunoglobulins) from any mammalian species can be assigned to one of two clearly distinct types, called kappa ("κ") and lambda ("λ"), based on the amino acid sequences of their constant domains.

The "CH1 domain" (also referred to as "C1" of "H1" domain) usually extends from about amino acid 118 to about amino acid 215 (EU numbering system).

"Hinge region" is generally defined as a region in IgG corresponding to Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S-S bonds in the same positions.

The "CH2 domain" of a human IgG Fc region (also referred to as "C2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec Immunol. 22:161-206 (1985).

The "CH3 domain" (also referred to as "C2" domain) comprises the residues between a CH2 domain and the C-terminal of an Fc region (i.e. from about amino acid residue 341 to the C-terminal end of an antibody sequence, typically at amino acid residue 446 or 447 of an IgG).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibitory receptor FcγRIIB contains an immunoreceptor tyrosine-based inhibition motif (ITIM) in its cytoplasmic domain. (See M. Daeron, Annu. Rev. Immunol. 15:203-234 (1997). FcRs are reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995). Other FcRs, including those to be identified in the future, are encompassed by the term "FcR" herein.

The term "epitope" as used herein refers to the specific group of atoms or amino acids on an antigen to which an antibody or antibody derivative binds. Two antibodies or antigen-binding moieties may bind the same epitope within an antigen if they exhibit competitive binding for the antigen.

As use herein, the terms "specifically binds," "specifically recognizing," and "is specific for" refer to measurable and reproducible interactions, such as binding between a target and an antibody or antibody moiety, which is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, greater avidity, greater readiness, and/or greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant ($K_D$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-, BIACORE™-tests and peptide scans.

An "isolated" antibody (or construct) is one that has been identified, separated and/or recovered from a component of its production environment (e.g., natural or recombinant). In certain embodiments, the isolated polypeptide is free or substantially free from association with all other components from its production environment.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. In certain embodiments, the isolated nucleic acid is free or substantially free from association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

Nucleic acid is "operably linked" or "operatively linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid, which cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell and may contain mutations. Mutant progeny that have the same function or biological activity as screened or selected for in the originally transformed cell are included herein.

The terms "subject," "individual," and "patient" are used interchangeably herein to refer to a mammal, including, but not limited to, human, bovine, horse, feline, canine, rodent, or primate. In some embodiments, the subject is a human.

An "effective amount" of an agent refers to an amount effective, at dosages and for periods of time necessary, to achieve the desired therapeutic or prophylactic result. The specific dose may vary depending on one or more of the particular agent chosen, the dosing regimen to be followed, whether it is administered in combination with other compounds, timing of administration, the tissue to be imaged, and the physical delivery system in which it is carried.

A "therapeutically effective amount" of a substance/molecule of the application, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the application contemplate any one or more of these aspects of treatment. "Treatment" does not necessarily mean that the condition being treated will be cured.

It is understood that embodiments of the application described herein include "consisting" and/or "consisting essentially of" embodiments.

As used herein, the term "about" or "approximately" means within an acceptable error range for the particular value as determined by one of ordinary skill in the art, which will depend in part on how the value is measured or determined, i.e., the limitations of the measurement system. In certain embodiments, "about" can mean within 3 or more than 3 standard deviations, per the practice in the art. In certain embodiments, "about" can mean a range of up to 20%, e.g., up to 10%, up to 5%, or up to 1% of a given value. In certain embodiments, particularly with respect to biological systems or processes, the term can mean within an order of magnitude, e.g., within 5-fold or within 2-fold, of a value.

As used herein, the term "modulate" means positively or negatively alter. Exemplary modulations include a about 1%, about 2%, about 5%, about 10%, about 25%, about 50%, about 75%, or about 100% change.

As used herein, the term "increase" means alter positively by at least about 5%. An alteration may be by about 5%, about 10%, about 25%, about 30%, about 50%, about 75%, about 100% or more.

As used herein, the term "reduce" means alter negatively by at least about 5%. An alteration may be by about 5%, about 10%, about 25%, about 30%, about 50%, about 75%, or even by about 100%.

The term "about X-Y" used herein has the same meaning as "about X to about Y."

As used herein and in the appended claims, the singular forms "a," "or," and "the" include plural referents unless the context clearly dictates otherwise.

"Effector functions" refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), phagocytosis, down regulation of cell surface receptors (e.g., B cell receptor), and B cell activation.

An "immunoconjugate" refers to an antibody conjugated to one or more heterologous molecule(s), including but not limited to a cytotoxic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier," as used herein, refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "variable region" or "variable domain" refers to the domain of an antibody heavy or light chain that is involved in binding the antibody to antigen. In certain embodiments, the variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 61ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "antigen-recognizing receptor" as used herein refers to a receptor that is capable of activating an immunoresponsive cell (e.g., a T-cell) in response to its binding to an antigen. Non-limiting examples of antigen-recognizing receptors include native and modified T cell receptors ("TCRs") and chimeric antigen receptors ("CARs").

The term "chimeric antigen receptor" or "CAR" as used herein refers to a molecule comprising an extracellular antigen-binding domain that is fused to an intracellular signaling domain that is capable of activating or stimulating an immunoresponsive cell, and a transmembrane domain. In certain embodiments, the extracellular antigen-binding domain of a CAR comprises an antibody or an antibody fragment, e.g., a VHH or a scFv. In certain embodiments, the antibody (e.g., VHH or scFv) is fused to the transmembrane domain, which is fused to the intracellular signaling domain. In certain embodiments, the CAR is selected to have high binding affinity or avidity for the antigen.

By"immunoresponsive cell" is meant a cell that functions in an immune response or a progenitor or progeny thereof.

2. Antibodies and Antibody Derivatives

The present disclosure provides antibodies and antibody derivatives. In certain embodiments, the disclosure is based, in part, on the discovery of a monoclonal antibodies that bind to GARP/TGFβ complex, which can be used in anti-tumor therapeutics where the antibodies selectively target a tumor cell and/or inhibit a signal pathway mediated by GARP/TGFβ complex and thereby induce beneficial anti-tumor effects against a tumor cell. In certain embodiments, an antibody disclosed herein is an antagonist antibody, which inhibits GARP/TGFβ complex functions. In certain embodiments, the anti-GARP/TGFβ antibody inhibit an interaction between GARP and one or more TGFβ molecules. In certain embodiments, the anti-GARP/TGFβ antibody blocks the signal pathway involving a GARP/TGFβ complex. In certain embodiments, the anti-GARP/TGFβ antibody blocks the release of mature TGFβ from a GARP/TGFβ complex. In certain embodiments, the anti-GARP/TGFβ antibody inhibits a TGFβ signal pathway in a tumor cell. In certain embodiments, the anti-GARP/TGFβ antibody inhibits a TGFβ signal pathway in an immune cell, e.g., a Treg cell. In certain embodiments, the anti-GARP/TGFβ antibody reduces an immune suppressive effect caused by a Treg cell. In certain embodiments, the anti-GARP/TGFβ antibody increases antitumor cytokine secretion in an immune cell, e.g., an effector T cell. In certain embodiments, the anti-GARP/TGFβ antibody exhibits a superior ability to increase antitumor cytokine secretion in an immune cell, e.g., an effector T cell, compared to a reference antibody, e.g., an ABBV-151 analog. In certain embodiments, the anti-GARP/TGFβ antibody exhibits antitumor efficacy in a subject. In certain embodiments, the anti-GARP/TGFβ antibody exhibits superior antitumor efficacy compared to a reference antibody, e.g., an ABBV-151 analog or a DS-1005a analog. ABBV-151, also known as LHG10.6, is an anti-GARP/TGFβ therapeutic antibody in clinical stage, the sequences of which are disclosed in US 2016/0251438.DS-1005a also known as H151D-H1L1, is an anti-GARP/TGFβ IgG1 antibody in clinical stage, the sequences of which are disclosed in US 2018/0258184.

In certain embodiments, an antibody of the present disclosure can be or comprise a monoclonal antibody, including a chimeric, humanized or human antibody. In certain embodiments, the antibody disclosed herein comprises a humanized antibody. In certain embodiments, the antibody comprises an acceptor human framework, e.g., a human immunoglobulin framework or a human consensus framework. In certain embodiments, the antibody disclosed herein comprises a human antibody.

In certain embodiments, an antibody of the present disclosure can be an antibody fragment, e.g., a Fv, Fab, Fab', scFv, diabody, or F(ab')2 fragment. In certain embodiments, the antibody is a full-length antibody, e.g., an intact IgG4 antibody, or other antibody class or isotype as defined herein. In certain embodiments, an antibody or antibody derivative of the present disclosure can incorporate any of the features, singly or in combination, as described in this application, e.g., Sections 2.1-2.12 detailed herein.

Antibodies and antibody derivatives of the present disclosure are useful, e.g., for the diagnosis or treatment of a neoplasm or a cancer. In certain embodiments, the neoplasia and cancers whose growth may be inhibited using the antibodies of this disclosure include neoplasia and cancers typically responsive to immunotherapy. In certain embodiments, the neoplasia and cancers include breast cancer (e.g., breast cell carcinoma), ovarian cancer (e.g., ovarian cell carcinoma) and renal cell carcinoma (RCC). Examples of other cancers that may be treated using the methods of this disclosure include melanoma (e.g., metastatic malignant melanoma), prostate cancer, colon cancer, lung cancer, bone cancer, pancreatic cancer, skin cancer, brain tumors, chronic or acute leukemias including acute myeloid leukemia, chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma) nasopharangeal carcinomas, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the breast gland, sarcoma of soft tissue, cancer of the urethra, cancer of the penis, solid tumors of childhood, cancer of the bladder, cancer of the kidney or ureter, carcinoma of the breast pelvis, neoplasm of the central nervous system (CNS), tumor angiogenesis, spinal axis tumor, brain stem glioma, pituitary adenoma, Kaposi's sarcoma, epidermoid cancer, squamous cell cancer, environmentally induced cancers including those induced by asbestos, e.g., mesothelioma and combinations of said cancers.

2.1.1 Exemplary Anti-GARP/TGFβ Antibodies

The present disclosure provides isolated antibodies that bind to a GARP/TGFβ complex. In certain embodiments, an anti-GARP/TGFβ antibody of the present disclosure binds to an ECD of GARP. In certain embodiments, the anti-GARP/TGFβ antibody binds to the N-terminal ECD of GARP that comprises the amino acid sequence set forth in SEQ ID NO: 86. In certain embodiments, the anti-GARP/TGFβ antibody binds to a GARP protein that is in a GARP/TGFβ complex. In certain embodiments, the anti-GARP/TGFβ antibody binds to a GARP protein that is not in a GARP/TGFβ complex, e.g., an isolated GARP protein. In certain embodiments, the anti-GARP/TGFβ antibody does not bind to a GARP protein that is not in a GARP/TGFβ complex. In certain embodiments, the anti-GARP/TGFβ antibody binds to the same epitope with an anti-GARP/TGFβ antibody described herein, e.g., Clone GA1, Clone hGA17 or their variants, e.g., GA1 #7, GA1 #8 or GA1 #9. In certain embodiments, the anti-GARP/TGFβ antibody binds to human GARP/TGFβ complex. In certain embodiments, the anti-GARP/TGFβ antibody binds to cynomolgus GARP/TGFβ complex. In certain embodiments, the anti-GARP/TGFβ antibody binds to mouse GARP/TGFβ complex. In certain embodiments, the anti-GARP/TGFβ antibody binds to human GARP/TGFβ complex, cynomolgus GARP/TGFβ complex and mouse GARP/TGFβ complex.

In certain embodiments, the anti-GARP/TGFβ antibody disclosed herein can function as an antagonist of a GARP/TGFβ-based signal pathway. In certain embodiments, the anti-GARP/TGFβ antibody can block or reduce the interaction between GARP and one or more of TGFβ molecules, e.g., TGFβ1, TGFβ2 or TGFβ3. In certain embodiments, the anti-GARP/TGFβ antibody can reduce the interaction between GARP and a TGFβ molecule by at least about 10%, about 20%, about 30%, about 40%, about 50%, about 60%, about 70%, about 80%, about 90%, about 99% or about 99.9%. In certain embodiments, the anti-GARP/TGFβ antibody blocks the function of a GARP/TGFβ complex. In certain embodiments, the anti-GARP/TGFβ antibody blocks the release of mature TGFβ from a GARP/TGFβ complex.

In certain embodiments, the anti-GARP/TGFβ antibody inhibits a TGFβ signal pathway in a target cell, e.g., by at least about 10%, about 20%, about 30%, about 40%, about 50%, about 60%, about 70%, about 80%, about 90%, about 99% or about 99.9%. In certain embodiments, the target cell is a tumor cell. In certain embodiments, the target cell is an immune cell, e.g., a Treg cell. In certain embodiments, the anti-GARP/TGFβ antibody reduces an immune suppressive effect caused by a Treg cell. In certain embodiments, the anti-GARP/TGFβ antibody increases antitumor cytokine secretion in an immune cell, e.g., an effector T cell. In certain embodiments, the anti-GARP/TGFβ antibody exhibits a superior ability to increase antitumor cytokine secretion in an immune cell, e.g., an effector T cell, compared to a reference antibody, e.g., an ABBV-151 analog.

In certain embodiments, treatment using the anti-GARP/TGFβ antibody exhibits antitumor efficacy in a subject, whereby reduces tumor growth and/or lengthen the survival of a subject. In certain embodiments, the anti-GARP/TGFβ antibody increases an immune response and/or an antitumor effect of an immune cell, e.g., an effector T cell and/or a NK cell. In certain embodiments, the anti-GARP/TGFβ antibody exhibits superior antitumor efficacy compared to a reference anti-GARP/TGFβ antibody, e.g., an ABBV-151analog or a DS-1055a analog.

In certain embodiments, the antibody binds to GARP/TGFβ complex with a KD of about $1\times10^{-7}$ M or less. In certain embodiments, the antibody binds to GARP/TGFβ complex with a KD of about $1\times10^{-8}$ M or less. In certain embodiments, the antibody binds to GARP/TGFβ complex with a KD of about $5\times10^{-9}$ M or less. In certain embodiments, the antibody binds to GARP/TGFβ complex with a KD of about $1\times10^{-9}$ M or less. In certain embodiments, the antibody binds to GARP/TGFβ complex with a KD of about $1\times10^{-10}$ M or less. In certain embodiments, the antibody binds to GARP/TGFβ complex with a KD of between about $1\times10^{-12}$ M and about $1\times10^{-7}$ M. In certain embodiments, the antibody binds to GARP/TGFβ complex with a KD of between about $1\times10^{-11}$ M and about $1\times10^{-8}$ M. In certain embodiments, the antibody binds to GARP/TGFβ complex with a KD of between about $1\times10^{-10}$ M and about $1\times10^{-8}$ M. In certain embodiments, the antibody binds to GARP/TGFβ complex with a KD of between about $1\times10^{-10}$ M and about $5\times10^{-8}$ M. In certain embodiments, the antibody binds to GARP/TGFβ complex with a KD of between about $5\times10^{-10}$ M and about $1\times10^{-9}$ M. In certain embodiments, the antibody binds to GARP/TGFβ complex with a KD of between about $1\times10^{-9}$ M and about $5\times10^{-8}$ M. In certain embodiments, the antibody binds to GARP/TGFβ complex with a KD of between about $1\times10^{-10}$ M and about $5\times10^{-9}$ M.

In certain embodiments, the anti-GARP/TGFβ antibody comprises: a) a heavy chain variable region comprising: (1) a heavy chain variable region CDR-H1 comprising an amino acid sequence of any one of SEQ ID NOs: 1, 11, 21, 31, 41, 51, 61 and 105, or a variant thereof comprising up to about 3 amino acid substitutions; (2) a heavy chain variable region CDR-H2 comprising an amino acid sequence of any one of SEQ ID NOs: 2, 12, 22, 32, 42, 52, 62 and 106, or a variant thereof comprising up to about 3 amino acid substitutions; and (3) a heavy chain variable region CDR-H3 comprising an amino acid sequence of any one of SEQ ID NOs: 3, 13, 23, 33, 43, 53, 63 and 107, or a variant thereof comprising up to about 3 amino acid substitutions; and b) a light chain variable region comprising: (1) a light chain variable region CDR-L1 comprising an amino acid sequence of any one of SEQ ID NOs: 4, 14, 24, 34, 44, 54, 64 and 108, or a variant thereof comprising up to about 3 amino acid substitutions; (2) a light chain variable region CDR-L2 comprising an amino acid sequence of any one of SEQ ID NOs: 5, 15, 25, 35, 45, 55, 65 and 109, or a variant thereof comprising up to about 3 amino acid substitutions; and (3) a light chain variable region CDR-L3 comprising an amino acid sequence of any one of SEQ ID NOs: 6, 16, 26, 36, 46, 56, 66 and 110, or a variant thereof comprising up to about 3 amino acid substitutions.

In certain embodiments, the anti-GARP/TGFβ antibody cross-competes with a reference anti-GARP/TGFβ antibody that comprises: a) a heavy chain variable domain (VH) sequence comprising (1) a CDR-H1 comprising the amino acid sequence set forth in SEQ ID NO: 1, (2) a CDR-H2 comprising the amino acid sequence set forth in SEQ ID NO: 2, and (3) a CDR-H3 comprising the amino acid sequence set forth in SEQ ID NO: 3; and a light chain variable domain (VL) sequence comprising (1) a CDR-L1 comprising the amino acid sequence set forth in SEQ ID NO: 4, (2) a CDR-L2 comprising the amino acid sequence set forth in SEQ ID NO: 5, and (3) a CDR-L3 comprising the amino acid sequence set forth in SEQ ID NO: 6; b) a heavy chain variable domain (VH) sequence comprising (1) a CDR-H1 comprising the amino acid sequence set forth in SEQ ID NO: 11, (2) a CDR-H2 comprising the amino acid sequence set forth in SEQ ID NO: 12, and (3) a CDR-H3 comprising the amino acid sequence set forth in SEQ ID NO: 13; and a light chain variable domain (VL) sequence comprising (1) a CDR-L1 comprising the amino acid sequence set forth in SEQ ID NO: 14, (2) a CDR-L2 comprising the amino acid sequence set forth in SEQ ID NO: 15, and (3) a CDR-L3 comprising the amino acid sequence set forth in SEQ ID NO: 16; c) a heavy chain variable domain (VH) sequence comprising (1) a CDR-H1 comprising the amino acid sequence set forth in SEQ ID NO: 21, (2) a CDR-H2 comprising the amino acid sequence set forth in SEQ ID NO: 22, and (3) a CDR-H3 comprising the amino acid sequence set forth in SEQ ID NO: 23; and a light chain variable domain (VL) sequence comprising (1) a CDR-L1 comprising the amino acid sequence set forth in SEQ ID NO: 24, (2) a CDR-L2 comprising the amino acid sequence set forth in SEQ ID NO: 25, and (3) a CDR-L3 comprising the amino acid sequence set forth in SEQ ID NO: 26; d) a heavy chain variable domain (VH) sequence comprising (1) a CDR-H1 comprising the amino acid sequence set forth in SEQ ID NO: 31, (2) a CDR-H2 comprising the amino acid sequence set forth in SEQ ID NO: 32, and (3) a CDR-H3 comprising the amino acid sequence set forth in SEQ ID NO: 33; and a light chain variable domain (VL) sequence comprising (1) a CDR-L1 comprising the amino acid sequence set forth in SEQ ID NO: 34, (2) a CDR-L2 comprising the amino acid sequence set forth in SEQ ID NO: 35, and (3) a CDR-L3 comprising the amino acid sequence set forth in SEQ ID NO: 36; e) a heavy chain variable domain (VH) sequence comprising (1) a CDR-H1 comprising the amino acid sequence set forth in SEQ ID NO: 41, (2) a CDR-H2 comprising the amino acid sequence set forth in SEQ ID NO: 42, and (3) a CDR-H3 comprising the amino acid sequence set forth in SEQ ID NO: 43; and a light chain variable domain (VL) sequence comprising (1) a CDR-L1 comprising the amino acid sequence set forth in SEQ ID NO: 44, (2) a CDR-L2 comprising the amino acid sequence set forth in SEQ ID NO: 45, and (3) a CDR-L3 comprising the amino acid sequence set forth in SEQ ID NO: 46; f) a heavy chain variable domain (VH) sequence comprising (1) a CDR-H1 comprising the amino acid sequence set forth in SEQ ID NO: 51, (2) a CDR-H2 comprising the amino acid sequence set forth in SEQ ID NO: 52, and (3) a CDR-H3 comprising the amino acid sequence set forth in SEQ ID NO: 53; and a light chain variable domain (VL) sequence comprising (1) a CDR-L1 comprising the amino acid sequence set forth in SEQ ID NO: 54, (2) a CDR-L2 comprising the amino acid sequence set forth in SEQ ID NO: 55, and (3) a CDR-L3 comprising the amino acid sequence set forth in SEQ ID NO: 56; g) a heavy chain variable domain (VH) sequence comprising (1) a CDR-H1 comprising the amino acid sequence set forth in SEQ ID NO: 61, (2) a CDR-H2 comprising the amino acid sequence set forth in SEQ ID NO: 62, and (3) a CDR-H3 comprising the amino acid sequence set forth in SEQ ID NO: 63; and a light chain variable domain (VL) sequence comprising (1) a CDR-L1 comprising the amino acid sequence set forth in SEQ ID NO: 64, (2) a CDR-L2 comprising the amino acid sequence set forth in SEQ ID NO: 65, and (3) a CDR-L3 comprising the amino acid sequence set forth in SEQ ID NO: 66; or h) a heavy chain variable domain (VH) sequence comprising (1) a CDR-H1 comprising the amino acid sequence set forth in SEQ ID NO: 105, (2) a CDR-H2 comprising the amino acid sequence set forth in SEQ ID NO: 106, and (3) a CDR-H3 comprising the amino acid sequence set forth in SEQ ID NO: 107; and a light chain variable domain (VL) sequence comprising (1) a CDR-L1 comprising the amino acid sequence set forth in SEQ ID NO: 108, (2) a CDR-L2 comprising the amino acid sequence set forth in SEQ ID NO: 109, and (3) a CDR-L3 comprising the amino acid sequence set forth in SEQ ID NO: 110.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence selected from the group consisting of SEQ ID NOs: 7, 17, 27, 37, 47, 57, 67, 85, 89, 93, 97, 101 and 111, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence selected from the group consisting of SEQ ID NOs: 8, 18, 28, 38, 48, 58, 68, 83, 84, 86, 90, 94, 98, 102 and 112.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 7, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 8.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 17, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 18.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 27, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 28.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 37, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 38.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 37, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 83.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 47, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 48.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 47, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 84.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 57, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 58.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 67, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 68.

In certain embodiments, the anti-GARP/TGFβ antibody comprises a heavy chain variable region that comprises a CDR-H1 domain, a CDR-H2 domain and a CDR-H3 domain, and a light chain variable region that comprises a CDR-L1 domain, a CDR-L2 domain and a CDR-L3 domain, wherein the CDR-H1 domain, the CDR-H2 domain and the CDR-H3 domain respectively comprise a CDR-H1 domain, a CDR-H2 domain and a CDR-H3 domain comprised in a reference heavy chain variable region comprising the amino acid sequence set forth in SEQ ID NO: 111, and the CDR-L1 domain, the CDR-L2 domain and the CDR-L3 domain respectively comprise a CDR-L1 domain, a CDR-L2 domain and a CDR-L3 domain comprised in a reference light chain variable region comprising the amino acid sequence forth in SEQ ID NO: 112.

In certain embodiments, the anti-GARP/TGFβ antibody comprises a heavy chain variable domain (VH) sequence comprising (1) a CDR-H1 comprising the amino acid sequence set forth in SEQ ID NO: 1, (2) a CDR-H2 comprising the amino acid sequence set forth in SEQ ID NO: 2, and (3) a CDR-H3 comprising the amino acid sequence set forth in SEQ ID NO: 3; and a light chain variable domain (VL) sequence comprising (1) a CDR-L1 comprising the amino acid sequence set forth in SEQ ID NO: 4, (2) a CDR-L2 comprising the amino acid sequence set forth in SEQ ID NO: 5, and (3) a CDR-L3 comprising the amino acid sequence set forth in SEQ ID NO: 6. In certain embodiments, the anti-GARP/TGFβ antibody comprises a heavy chain variable domain (VH) sequence comprising (1) a CDR-H1 comprising the amino acid sequence set forth in SEQ ID NO: 11, (2) a CDR-H2 comprising the amino acid sequence set forth in SEQ ID NO: 12, and (3) a CDR-H3 comprising the amino acid sequence set forth in SEQ ID NO: 13; and a light chain variable domain (VL) sequence comprising (1) a CDR-L1 comprising the amino acid sequence set forth in SEQ ID NO: 14, (2) a CDR-L2 comprising the amino acid sequence set forth in SEQ ID NO: 15, and (3) a CDR-L3 comprising the amino acid sequence set forth in SEQ ID NO: 16. In certain embodiments, the anti-GARP/TGFβ antibody comprises a heavy chain variable domain (VH) sequence comprising (1) a CDR-H1 comprising the amino acid sequence set forth in SEQ ID NO: 21, (2) a CDR-H2 comprising the amino acid sequence set forth in SEQ ID NO: 22, and (3) a CDR-H3 comprising the amino acid sequence set forth in SEQ ID NO: 23; and a light chain variable domain (VL) sequence comprising (1) a CDR-L1 comprising the amino acid sequence set forth in SEQ ID NO: 24, (2) a CDR-L2 comprising the amino acid sequence set forth in SEQ ID NO: 25, and (3) a CDR-L3 comprising the amino acid sequence set forth in SEQ ID NO: 26. In certain embodiments, the anti-GARP/TGFβ antibody comprises a heavy chain variable domain (VH) sequence comprising (1) a CDR-H1 comprising the amino acid sequence set forth in SEQ ID NO: 31, (2) a CDR-H2 comprising the amino acid sequence set forth in SEQ ID NO: 32, and (3) a CDR-H3 comprising the amino acid sequence set forth in SEQ ID NO: 33; and a light chain variable domain (VL) sequence comprising (1) a CDR-L1 comprising the amino acid sequence set forth in SEQ ID NO: 34, (2) a CDR-L2 comprising the amino acid sequence set forth in SEQ ID NO: 35, and (3) a CDR-L3 comprising the amino acid sequence set forth in SEQ ID NO: 36. In certain embodiments, the anti-GARP/TGFβ antibody comprises a heavy chain variable domain (VH) sequence comprising (1) a CDR-H1 comprising the amino acid sequence set forth in SEQ ID NO: 41, (2) a CDR-H2 comprising the amino acid sequence set forth in SEQ ID NO: 42, and (3) a CDR-H3 comprising the amino acid sequence set forth in SEQ ID NO: 43; and a light chain variable domain (VL) sequence comprising (1) a CDR-L1 comprising the amino acid sequence set forth in SEQ ID NO: 44, (2) a CDR-L2 comprising the amino acid sequence set forth in SEQ ID NO: 45, and (3) a CDR-L3 comprising the amino acid sequence set forth in SEQ ID NO: 46. In certain embodiments, the anti-GARP/TGFβ antibody comprises a heavy chain variable domain (VH) sequence comprising (1) a CDR-H1 comprising the amino acid sequence set forth in SEQ ID NO: 51, (2) a CDR-H2 comprising the amino acid sequence set forth in SEQ ID NO: 52, and (3) a CDR-H3 comprising the amino acid sequence set forth in SEQ ID NO: 53; and a light chain variable domain (VL) sequence comprising (1) a CDR-L1 comprising the amino acid sequence set forth in SEQ ID NO: 54, (2) a CDR-L2 comprising the amino acid sequence set forth in SEQ ID NO: 55, and (3) a CDR-L3 comprising the amino acid sequence set forth in SEQ ID NO: 56. In certain embodiments, the anti-GARP/TGFβ antibody comprises a heavy chain variable domain (VH) sequence comprising (1) a CDR-H1 comprising the amino acid sequence set forth in SEQ ID NO: 61, (2) a CDR-H2 comprising the amino acid sequence set forth in SEQ ID NO: 62, and (3) a CDR-H3 comprising the amino acid sequence set forth in SEQ ID NO: 63; and a light chain variable domain (VL) sequence comprising (1) a CDR-L1 comprising the amino acid sequence set forth in SEQ ID NO: 64, (2) a CDR-L2 comprising the amino acid sequence set forth in SEQ ID NO: 65, and (3) a CDR-L3 comprising the amino acid sequence set forth in SEQ ID NO: 66. In certain embodiments, the anti-GARP/TGFβ antibody comprises a heavy chain variable domain (VH) sequence comprising (1) a CDR-H1 comprising the amino acid sequence set forth in SEQ ID NO: 105, (2) a CDR-H2 comprising the amino acid sequence set forth in SEQ ID NO: 106, and (3) a CDR-H3 comprising the amino acid sequence set forth in SEQ ID NO: 107; and a light chain variable domain (VL) sequence comprising (1) a CDR-L1 comprising the amino acid sequence set forth in SEQ ID NO: 108, (2) a CDR-L2 comprising the amino acid sequence set forth in SEQ ID NO: 109, and (3) a CDR-L3 comprising the amino acid sequence set forth in SEQ ID NO: 110.

In certain embodiments, the anti-GARP/TGFβ antibody comprises a heavy chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 7, 17, 27, 37, 47, 57, 67, 85, 89, 93, 97, 101 and 111, and a light chain variable region comprising an amino acid sequence having at least about 80%, 85%, 90%, 91%, 92%, 93%, 94%, 95%, 96%, 97%, 98%, 99%, or 100% sequence identity to the amino acid sequence selected from the group consisting of SEQ ID NOs: 8, 18, 28, 38, 48, 58, 68, 83, 84, 86, 90, 94, 98, 102 and 112. In certain embodiments, the anti-GARP/TGFβ antibody comprises a heavy chain variable region comprising an amino acid sequence selected from the group consisting of SEQ ID NOs: 7, 17, 27, 37, 47, 57, 67, 85, 89, 93, 97, 101 and 111, and a light chain variable region comprising an amino acid sequence selected from the group consisting of SEQ ID NOs: 8, 18, 28, 38, 48, 58, 68, 83, 84, 86, 90, 94, 98, 102 and 112.

In certain embodiments, the anti-GARP/TGFβ antibody comprises a heavy chain variable region comprising the amino acid sequence set forth in SEQ ID NO: 7, and a light chain variable region comprising the amino acid sequence set forth in SEQ ID NO: 8. In certain embodiments, the anti-GARP/TGFβ antibody comprises a heavy chain variable region comprising the amino acid sequence set forth in SEQ ID NO: 17, and a light chain variable region comprising the amino acid sequence set forth in SEQ ID NO: 18. In certain embodiments, the anti-GARP/TGFβ antibody comprises a heavy chain variable region comprising the amino acid sequence set forth in SEQ ID NO: 27, and a light chain variable region comprising the amino acid sequence set forth in SEQ ID NO: 28. In certain embodiments, the anti-GARP/TGFβ antibody comprises a heavy chain variable region comprising the amino acid sequence set forth in SEQ ID NO: 37, and a light chain variable region comprising the amino acid sequence set forth in SEQ ID NO: 38. In certain embodiments, the anti-GARP/TGFβ antibody comprises a heavy chain variable region comprising the amino acid sequence set forth in SEQ ID NO: 37, and a light chain variable region comprising the amino acid sequence set forth in SEQ ID NO: 83. In certain embodiments, the anti-GARP/TGFβ antibody comprises a heavy chain variable region comprising the amino acid sequence set forth in SEQ ID NO: 47, and a light chain variable region comprising the amino acid sequence set forth in SEQ ID NO: 48. In certain embodiments, the anti-GARP/TGFβ antibody comprises a heavy chain variable region comprising the amino acid sequence set forth in SEQ ID NO: 47, and a light chain variable region comprising the amino acid sequence set forth in SEQ ID NO: 84. In certain embodiments, the anti-GARP/TGFβ antibody comprises a heavy chain variable region comprising the amino acid sequence set forth in SEQ ID NO: 57, and a light chain variable region comprising the amino acid sequence set forth in SEQ ID NO: 58. In certain embodiments, the anti-GARP/TGFβ antibody comprises a heavy chain variable region comprising the amino acid sequence set forth in SEQ ID NO: 67, and a light chain variable region comprising the amino acid sequence set forth in SEQ ID NO: 68. In certain embodiments, the antibody comprises a heavy chain variable region comprising the amino acid sequence set forth in SEQ ID NO: 85, and a light chain variable region comprising the amino acid sequence set forth in SEQ ID NO: 86. In certain embodiments, the antibody comprises a heavy chain variable region comprising the amino acid sequence set forth in SEQ ID NO: 89, and a light chain variable region comprising the amino acid sequence set forth in SEQ ID NO: 90. In certain embodiments, the antibody comprises a heavy chain variable region comprising the amino acid sequence set forth in SEQ ID NO: 93, and a light chain variable region comprising the amino acid sequence set forth in SEQ ID NO: 94. In certain embodiments, the antibody comprises a heavy chain variable region comprising the amino acid sequence set forth in SEQ ID NO: 97, and a light chain variable region comprising the amino acid sequence set forth in SEQ ID NO: 98. In certain embodiments, the antibody comprises a heavy chain variable region comprising the amino acid sequence set forth in SEQ ID NO: 101, and a light chain variable region comprising the amino acid sequence set forth in SEQ ID NO: 102. In certain embodiments, the antibody comprises a heavy chain variable region comprising the amino acid sequence set forth in SEQ ID NO: 111, and a light chain variable region comprising the amino acid sequence set forth in SEQ ID NO: 112.

In certain embodiments, any one of the amino acid sequences comprised in the heavy chain variable region can comprise up to about 1, about 2, about 3, about 4, about 5, about 6, about 7, about 8, about 9 or about 10 amino acid substitutions, deletions and/or additions. In certain embodiments, the amino acid substitution is a conservative substitution.

In certain embodiments, the antibody comprises a human framework. In certain embodiments, the antibody is a human antibody. In certain embodiments, the antibody is isolated from a human-derived phage display library.

In certain embodiments, the anti-GARP/TGFβ antibody does not comprise a Fc region. In certain embodiments, the anti-GARP/TGFβ antibody further comprises a Fc region. In certain embodiments, the Fc region comprises a human Fc region. In certain embodiments, the Fc region comprises a Fc region selected from the group consisting of the Fc regions of IgG, IgA, IgD, IgE and IgM. In certain embodiments, the Fc region comprises a Fc region selected from the group consisting of the Fc regions of IgG1, IgG2, IgG3 and IgG4. In certain embodiments, the Fc region comprises an IgG1 Fc region. In certain embodiments, the IgG1 Fc region comprising one or more mutation that modifies an antibody-dependent cell-mediated cytotoxicity (ADCC). In certain embodiments, the IgG1 Fc region comprising one or more mutation that reduces an antibody-dependent cell-mediated cytotoxicity (ADCC). In certain embodiments, the IgG1 Fc region comprising one or more mutation that enhances an antibody-dependent cell-mediated cytotoxicity (ADCC). In certain embodiments, the Fc region comprises an IgG4 Fc region. In certain embodiments, the IgG4 Fc region comprises a mutation of S228P. In certain embodiments, the Fc region comprises a C-terminal lysine. In certain embodiments, the Fc region comprises a deletion of a C-terminal lysine.

In certain embodiments, the anti-GARP/TGFβ antibody comprises a heavy chain and a light chain comprising respectively the amino acid sequences set forth in SEQ ID NOs: 71 and 72, respectively (GA1 #7K). In certain embodiments, the anti-GARP/TGFβ antibody comprises a heavy chain and a light chain comprising respectively the amino acid sequences set forth in SEQ ID NOs: 73 and 74, respectively (GA1 #7K (LC_FS/IT)). In certain embodiments, the anti-GARP/TGFβ antibody comprises a heavy chain and a light chain comprising respectively the amino acid sequences set forth in SEQ ID NOs: 75 and 76, respectively (GA1 #7 (LC_FS/IT)). In certain embodiments, the anti-GARP/TGFβ antibody comprises a heavy chain and a light chain comprising respectively the amino acid sequences set forth in SEQ ID NOs: 77 and 78, respectively (GA1 #8K). In certain embodiments, the anti-GARP/TGFβ antibody comprises a heavy chain and a light chain comprising respectively the amino acid sequences set forth in SEQ ID NOs: 79 and 80, respectively (GA1 #8K (LC_FS/IT)). In certain embodiments, the anti-GARP/TGFβ antibody comprises a heavy chain and a light chain comprising respectively the amino acid sequences set forth in SEQ ID NOs: 81 and 82, respectively (GA1 #8 (LC_FS/IT)). In certain embodiments, the anti-GARP/TGFβ antibody comprises a heavy chain and a light chain comprising respectively the amino acid sequences set forth in SEQ ID NOs: 87 and 88, respectively (GA1 #8_14). In certain embodiments, the anti-GARP/TGFβ antibody comprises a heavy chain and a light chain comprising respectively the amino acid sequences set forth in SEQ ID NOs: 91 and 92, respectively (GA1 #8_17). In certain embodiments, the anti-GARP/TGFβ antibody comprises a heavy chain and a light chain comprising respectively the amino acid sequences set forth in SEQ ID NOs: 95 and 96, respectively (GA1 #8_18). In certain embodiments, the anti-GARP/TGFβ antibody comprises a heavy chain and a light chain comprising respectively the amino acid sequences set forth in SEQ ID NOs: 99 and 100, respectively (GA1 #8_20). In certain embodiments, the anti-GARP/TGFβ antibody comprises a heavy chain and a light chain comprising respectively the amino acid sequences set forth in SEQ ID NOs: 103 and 104, respectively (GA1 #8_21). In certain embodiments, the anti-GARP/TGFβ antibody comprises a heavy chain and a light chain comprising respectively the amino acid sequences set forth in SEQ ID NOs: 113 and 114, respectively (hGA17).

In certain embodiments, the anti-GARP/TGFβ antibody comprises a full-length immunoglobulin, a single-chain Fv (scFv) fragment, a Fab fragment, a Fab' fragment, a F(ab')2, a Fv fragment, a disulfide stabilized Fv fragment (dsFv), a (dsFv)2, a VHH, a Fv-Fc fusion, a scFv-Fc fusion, a VHH-Fv fusion, a diabody, a tribody, a tetrabody or any combination thereof.

In certain embodiments, the antibody is comprised in a larger molecule that is an antibody derivative. In certain embodiments, the antibody derivative is a multispecific antibody, e.g., a bispecific antibody, wherein the multispecific antibody comprises a second antibody moiety that specifically binds to a second antigen. In certain embodiments, the second antigen is a tumor associated antigen. In certain embodiments, the tumor associated antigen is selected from the group consisting of Her-2, B7H3, EGFR, PD-L1, MSLN, c-Met, B Cell Maturation Antigen (BCMA), carbonic anhydrase IX (CA1X), carcinoembryonic antigen (CEA), CD5, CD7, CD10, CD19, CD20, CD22, CD30, CD33, CD34, CD38, CD41, CD44, CD47, CD49f, CD56, CD74, CD123, CD133, CD138, CD276 (B7H3), epithelial glycoprotein (EGP2), trophoblast cell-surface antigen 2 (TROP-2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human telomerase reverse transcriptase (hTERT), kinase insert domain receptor (KDR), Lewis A (CA 1.9.9), Lewis Y (LeY), Glypican-3 (GPC3), L1 cell adhesion molecule (LiCAM), Mucin 16 (Muc-16), Mucin 1 (Muc-1), NG2D ligands, oncofetal antigen (h5T4), prostate stem cell antigen (PSCA), prostate-specific membrane antigen (PSMA), tumor-associated glycoprotein 72 (TAG-72), Claudini8.2 (CLDN18.2), vascular endothelial growth factor R2 (VEGF-R2), Wilms tumor protein (WT-1), type 1 tyrosine-protein kinase transmembrane receptor (ROR1), PVR, PVRL2 and any combination thereof. In certain embodiments, the second antigen is an immune checkpoint regulator. In certain embodiments, the immune checkpoint regulator is selected from the group consisting of TIGIT, PD1, CTLA4, LAG-3, 2B4, BTLA and any combination thereof. In certain embodiments, binding of the antibody derivative or multispecific antibody to the second antigen inhibits the immune checkpoint regulator. In certain embodiments, the second antigen is an immune costimulatory molecule or a subunit of a T cell receptor/CD3 complex. In certain embodiments, the immune costimulatory molecule is selected from the group consisting of CD28, ICOS, CD27, 4-1BB, OX40 and CD40 and any combination thereof. In certain embodiments, binding of the antibody derivative or multispecific antibody to the second antigen activates the immune costimulatory molecule. In certain embodiments, the subunit of the T cell receptor/CD3 complex is selected from the group consisting of CD3γ, CD3δ, CD3ε and any combination thereof. In certain embodiments, binding of the antibody derivative or multispecific antibody to the second antigen activates the T cell receptor/CD3 complex.

In certain embodiments, the anti-GARP/TGFβ antibody is linked to the second antigen binding moiety via a linker. In certain embodiments, the linker is a peptide linker. In certain embodiments, the peptide linker comprises about four to about thirty amino acids. In certain embodiments, the peptide linker comprises about four to about fifteen amino acids. In certain embodiments, the peptide linker comprises an amino acid sequence selected from the group consisting of SEQ ID NOs: 117-145.

In certain embodiments, the anti-GARP/TGFβ antibody is conjugated to a therapeutic agent or a label. In certain embodiments, the label is selected from the group consisting of a radioisotope, a fluorescent dye and an enzyme. In certain embodiments, the therapeutic agent is a cytotoxin or a radioactive isotope.

2.2 Antibody Affinity

In certain embodiments, an antibody or antibody derivative disclosed herein has a high binding affinity to its target antigen. In certain embodiments, the antibody or antibody derivative binds to the target with a KD of about $1\times10^{-7}$ M or less. In certain embodiments, the antibody or antibody derivative binds to the target with a KD of about $1\times10^{-8}$ M or less. In certain embodiments, the antibody or antibody derivative binds to the target with a KD of about $5\times10^{-9}$ M or less. In certain embodiments, the antibody or antibody derivative binds to the target with a KD of about $1\times10^{-9}$ M or less. In certain embodiments, the antibody or antibody derivative binds to the target with a KD of about $1\times10^{-10}$ M or less.

In certain embodiments, the antibody or antibody derivative binds to the target with a KD of between about $1\times10^{-12}$ M and about $1\times10^{-7}$ M. In certain embodiments, the antibody or antibody derivative binds to the target with a KD of between about $1\times10^{-11}$ M and about $1\times10^{-7}$ M. In certain embodiments, the antibody or antibody derivative binds to the target with a KD of between about $1\times10^{-10}$ M and about $5\times10^{-8}$ M. In certain embodiments, the antibody or antibody derivative binds to the target with a KD of between about $1\times10^{-11}$ M and about $1\times10^{-9}$ M. In certain embodiments, the antibody or antibody derivative binds to the target with a KD of between about $2\times10^{-10}$ M and about $5\times10^{-9}$ M. In certain embodiments, the antibody or antibody derivative binds to the target with a KD of between about $1\times10^{-9}$ M and about $5\times10^{-8}$ M. In certain embodiments, the antibody or antibody derivative binds to the target with a KD of between about $1\times10^{-10}$ M and about $1\times10^{-9}$ M.

The KD of the antibody or antibody derivative can be determined by methods known in the art. Such methods comprise, but are not limited to Western blots, ELISA-, RIA-, ECL-, IRMA-, EIA-, Octet-BIACORE®-tests and peptide scans.

In certain embodiments, KD can be measured using a BIACORE® surface plasmon resonance assay. For example, and not by way of limitation, an assay using a BIACORE®-2000 or a BIACORE® 3000 (Biacore, Inc., Piscataway, NJ) is performed at 25° C. with immobilized antigen CMS chips at about 10 response units (RU). In certain embodiments, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (about 0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (KD) can be calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2.3 Antibody Fragments

In certain embodiments, an antibody of the present disclosure comprises an antigen-binding fragment or antibody fragment. Antibody fragments include, but are not limited to, Fab, Fab', Fab'-SH, F(ab')2, VHH, Fv, and scFv fragments, and other fragments described herein. For a review of certain antibody fragments, see Hudson et al. Nat. Med. 9: 129-134 (2003). For a review of scFv fragments, see e.g., Pluckthin, in The Pharmacology of Monoclonal Antibodies, vol. 113, Rosenburg and Moore eds., (Springer-Verlag, New York), pp. 269-31 5 (1994); see also WO 93/16185; and U.S. Pat. Nos. 5,571,894 and 5,587,458. For discussion of Fab and $F(ab)_2$ fragments comprising salvage receptor binding epitope residues and having increased in vivo half-life, see U.S. Pat. No. 5,869,046.

In certain embodiments, an antibody of the present disclosure can be a diabody. Diabodies are antibody fragments with two antigen-binding sites that may be bivalent or bispecific. See, for example, EP 404,097; WO 1993/01 161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9: 129-134 (2003).

In certain embodiments, an antibody of the present disclosure can comprise a single domain antibody. Single domain antibodies are antibody fragments that comprise all or a portion of the heavy chain variable domain or all or a portion of the light chain variable domain of an antibody. In certain embodiments, the single domain antibody is a human single-domain antibody (Domantis, Inc., Waltham, MA; see, e.g., U.S. Pat. No. 6,248,516 B1). In certain embodiments, the single domain antibody is camelid single-domain antibody. In certain embodiments, the single domain antibody is a VHH. In certain embodiments, the single domain antibody is a chimeric antibody. In certain embodiments, the single domain antibody is a humanized antibody.

Antibody fragments can be made by various techniques including, but not limited to, proteolytic digestion of an intact antibody as well as production by recombinant host cells (e.g., *E. coli* or phage), as described herein.

2.4 Chimeric and Humanized Antibodies

In certain embodiments, an antibody of the present disclosure is a chimeric antibody. Certain chimeric antibodies are described, e.g., in U.S. Pat. No. 4,816,567; and Morrison et al., Proc. Natl. Acad. Sci. USA, 81:6851-6855 (1984)). In certain embodiments, a chimeric antibody comprises a non-human variable region (e.g., a variable region derived from mouse) and a human constant region. In certain embodiments, a chimeric antibody is a "class switched" antibody in which the class or subclass has been changed from that of the parent antibody. Chimeric antibodies include antigen-binding fragments thereof.

In certain embodiments, an antibody of the present disclosure can be a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and one or more framework (FR) (or any portion thereof) are derived from human antibody sequences. A humanized antibody optionally can also comprise at least a portion of a human constant region. In certain embodiments, certain FR residues in a humanized antibody are substituted with corresponding residues from a non-human antibody (e.g., the antibody from which the HVR residues are derived), e.g., to restore or improve antibody specificity or affinity.

Humanized antibodies and methods of making them are described, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); Framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

2.5 Human Antibodies

In certain embodiments, an antibody of the present disclosure can be a human antibody (e.g., human domain antibody, or human DAb). Human antibodies can be produced using various techniques known in the art. Human antibodies are described generally in van Dijk and van de Winkel, Curr. Opin. Pharmacol. 5: 368-74 (2001), Lonberg, Curr. Opin. Immunol. 20:450-459 (2008), and Chen, Mol.

Immunol. 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies have been described (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991)). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4): 265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

2.6 Library-Derived Antibodies

An antibody of the present disclosure may be isolated by screening combinatorial libraries for antibodies with the desired activity or activities. For example, a variety of methods are known in the art for generating phage display libraries and screening such libraries for antibodies possessing the desired binding characteristics. Such methods are described, e.g., in Hoogenboom et al. in Methods in Molecular Biology 178:1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

2.7 Antibody Variants

The presently disclosure further provides amino acid sequence variants of the disclosed antibodies. For example, it may be desirable to improve the binding affinity and/or other biological properties of the antibody. Amino acid sequence variants of an antibody can be prepared by introducing appropriate modifications into the nucleotide sequence encoding the antibody, or by peptide synthesis. Such modifications include, but are not limited to, deletions from, and/or insertions into and/or substitutions of residues within the amino acid sequences of the antibody. Any combination of deletion, insertion, and substitution can be made to arrive at the final construct, provided that the final antibody, i.e., modified, possesses the desired characteristics, e.g., antigen-binding.

2.7.1 Substitution, Insertion, and Deletion Variants

In certain embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Amino acid substitutions | | |
|---|---|---|
| Original | Exemplary Substitutions | Preferred |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; | Leu |
| Leu (L) | Norleucine; Ile; Val; Met; | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. In certain embodiments, non-conservative substitutions will entail exchanging a member of one of these classes for another class.

In certain embodiments, a type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR (or CDR) residues are mutated and the variant antibodies displayed on phage and screened for a particular biological activity (e.g. binding affinity).

Alterations (e.g., substitutions) may be made in HVRs (or CDRs), e.g., to improve antibody affinity. Such alterations may be made in HVR (or CDRs) "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001)). In certain embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR (or CDRs)-directed approaches, in which several HVR (or CDRs) residues (e.g., 4-6 residues at a time) are randomized. HVR (or CDRs) residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs (or CDRs) so long as such alterations do not substantially reduce the ability of the antibody to bind antigen. For example, conservative alterations (e.g., conservative substitutions as provided herein) that do not substantially reduce binding affinity may be made in HVRs (or CDRs). Such alterations may be outside of HVR (or CDR) "hotspots" or CDRs. In certain embodiments of the variant VHH sequences provided above, each HVR (or CDR) either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

2.7.2 Glycosylation Variants

In certain embodiments, an antibody is altered to increase or decrease the extent to which the construct is glycosylated. Addition or deletion of glycosylation sites to an antibody may be conveniently accomplished by altering the amino acid sequence such that one or more glycosylation sites is created or removed.

Where the antibody comprises an Fc region (e.g., scFv-Fc), the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In certain embodiments, modifications of the oligosaccharide in the antibody may be made in order to create antibody variants with certain improved properties.

In certain embodiments, the antibody has a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Patent Application No. US 2003/0157108 A1, Presta, L; and WO 2004/056312 A1, Adams et al.), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

In certain embodiments, the antibody has bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

2.7.3 Fc Region Variants

In certain embodiments, the Fc region of a presently disclosed antibody or antibody derivative may comprise a human Fc region sequence (e.g., a human IgG1, IgG2, IgG3 or IgG4 Fc region) comprising an amino acid modification (e.g. a substitution) at one or more amino acid positions. In certain embodiments, one or more amino acid modifications may be introduced into the Fc region of the antibody moiety (e.g., scFv-Fc or VHH-Fc), thereby generating an Fc region variant.

In certain embodiments, the Fc region possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).) In certain embodiments, the Fc region comprises one or more mutation according to EU numbering of residues. In certain embodiments, the Fc region is an IgG1 Fc region. In certain embodiments, the IgG1 Fc region comprises a L234A mutation and/or a L235A mutation. In certain embodiments, the Fc region is an IgG2 or IgG4 Fc region. In certain embodiments, the Fc region is an IgG4 Fc region comprising a F234A, and/or a L235A mutation.

In certain embodiments, the Fc region is an IgG1 Fc region. In certain embodiments, the IgG1 Fc region comprising one or more mutation that modifies an antibody-dependent cell-mediated cytotoxicity (ADCC). In certain embodiments, the IgG1 Fc region comprising one or more mutation that reduces an antibody-dependent cell-mediated cytotoxicity (ADCC). In certain embodiments, the IgG1 Fc region comprising one or more mutation that enhances an antibody-dependent cell-mediated cytotoxicity (ADCC). In certain embodiments, the IgG1 Fc region comprises the mutations of L235V, F243L, R292P, Y300L and P396L. In certain embodiments, the IgG1 Fc region comprises the mutations of S239D, A330L and 1332E. In certain embodiments, the IgG1 Fc region comprises the mutations of L235V, F243L, R292P and Y300L. In certain embodiments, the IgG1 Fc region comprises substitutions at positions 298, 333, and/or 334 of the Fc region.

In certain embodiments, the Fc region comprises an IgG4 Fc region. In certain embodiments, the IgG4 Fc region comprises an S228P mutation.

In certain embodiments, the Fc region comprises a C-terminal lysine. In certain embodiments, the Fc region comprises a deletion of a C-terminal lysine.

In certain embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

In certain embodiments, the antibody (e.g., scFv-Fc or VHH-Fc) variant comprising a variant Fc region comprising one or more amino acid substitutions which alters half-life and/or changes binding to the neonatal Fc receptor (FcRn). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which alters binding of the Fc region to FcRn. Such Fc variants include those with substitutions at one or more of Fc region residues, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

2.7.4 Cysteine Engineered Antibody Variants

In certain embodiments, it may be desirable to create cysteine engineered antibody moieties, e.g., "thioMAbs," in which one or more residues of an antibody are substituted with cysteine residues. In certain embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: Al 18 (EU numbering) of the heavy chain; and S400 (EU numbering) of the heavy chain Fc region. Cysteine engineered antibody moieties may be generated as described, e.g., in U.S. Pat. No. 7,521,541.

2.8 Antibody Derivatives

In certain embodiments, an antibody described herein may be further modified to be an antibody derivative comprising additional proteinaceous or nonproteinaceous moieties that are known in the art and readily available. Nonproteinaceous moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in diagnosis under defined conditions, etc.

In certain embodiments, an antibody may be further modified to be an antibody derivative comprising one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In certain embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine.

2.9 Methods of Production

The antibodies and antibody derivatives disclosed herein can be produced using any available or known technique in the art. For example, but not by way of limitation, antibodies and antibody derivatives can be produced using recombinant methods and compositions, e.g., as described in U.S. Pat. No. 4,816,567. Detailed procedures to generate antibodies and antibody derivatives are described in the Examples below.

The presently disclosed subject matter further provides isolated nucleic acids encoding an antibody or antibody derivative disclosed herein. For example, the isolated nucleic acid can encode an amino acid sequence comprising the VL and/or an amino acid sequence comprising the VH of the antibody, e.g., the light and/or heavy chains of the antibody.

In certain embodiments, the nucleic acid can be present in one or more vectors, e.g., expression vectors. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, where additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the disclosed subject matter is intended to include such other forms of expression vectors, such as viral vectors (e.g., replication defective retroviruses, adenoviruses and adeno-associated viruses) that serve equivalent functions.

Different parts of an antibody or antibody derivative disclosed herein can be constructed in a single, multicistronic expression cassette, in multiple expression cassettes of a single vector, or in multiple vectors. Examples of elements that create polycistronic expression cassette include, but are not limited to, various viral and non-viral Internal Ribosome Entry Sites (TRES, e.g., FGF-1 IRES, FGF-2 IRES, VEGF IRES, IGF-II IRES, NF-kB IRES, RUNX1 TRES, p53 IRES, hepatitis A TRES, hepatitis C IRES, pestivirus IRES, aphthovirus TRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD 114 or GALV envelope and any other known in the art.

In certain embodiments, the nucleic acid encoding an antibody or antibody derivative of the present disclosure and/or the one or more vectors including the nucleic acid can be introduced into a host cell. In certain embodiments, the introduction of a nucleic acid into a cell can be carried out by any method known in the art including, but not limited to, transfection, electroporation, microinjection, infection with a viral or bacteriophage vector containing the nucleic acid sequences, cell fusion, chromosome-mediated gene transfer, microcell-mediated gene transfer, spheroplast fusion, etc. In certain embodiments, a host cell can include, e.g., has been transformed with: a vector comprising a nucleic acid that encodes an amino acid sequence comprising a single domain antibody and/or the VH of a single domain antibody. In certain embodiments, a host cell can include, e.g., has been transformed with: (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In certain embodiments, the host cell is eukaryotic, e.g., a Chinese Hamster Ovary (CHO) cell or lymphoid cell (e.g., YO, NSO, Sp20 cell).

In certain embodiments, the methods of making an antibody or antibody derivative disclosed herein can include culturing a host cell, in which a nucleic acid encoding the antibody or antibody derivative has been introduced, under conditions suitable for expression of the antibody or antibody derivative, and optionally recovering the antibody or antibody derivative from the host cell and/or host cell culture medium. In certain embodiments, the antibody or antibody derivative is recovered from the host cell through chromatography techniques.

For recombinant production of an antibody or antibody derivative of the present disclosure, a nucleic acid encoding an antibody or antibody derivative, e.g., as described above, can be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody or antibody derivative). Suitable host cells for cloning or expression of antibody-encoding vectors include prokaryotic or eukaryotic cells described herein. For example, an antibody or antibody derivative can be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*.) After expression, the antibody or antibody derivative may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody or antibody derivative with a partially or fully human glycosylation pattern. See Gemgross, Nat. Biotech. 22:1409-1414 (2004), and Li et al., Nat. Biotech. 24:21 0-215 (2006). Suitable host cells for the expression of glycosylated antibody can also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. In certain embodiments, plant cell cultures can be utilized as host cells. See, e.g., U.S. Pat. Nos. 5,959,177, 6,040,498, 6,420,548, 7,125,978, and 6,417,429 (describing PLANTIBODIES™ technology for producing antibodies in transgenic plants).

In certain embodiments, vertebrate cells can also be used as hosts. For example, and not by way of limitation, mammalian cell lines that are adapted to grow in suspension can be useful. Non-limiting examples of useful mammalian host cell lines are monkey kidney CVI line transformed by SY40 (COS-7); human embryonic kidney line (293 or 293 cells as described, e.g., in Graham et al., J Gen Viral. 36:59 (1977)); baby hamster kidney cells (BHK); mouse sertoli cells (TM4 cells as described, e.g., in Mather, Biol. Reprod. 23:243-251 (1980)); monkey kidney cells (CV 1); African green monkey kidney cells (VERO-76); human cervical carcinoma cells (HELA); canine kidney cells (MDCK; buffalo rat liver cells (BRL 3A); human lung cells (W138); human liver cells (Hep 02); mouse mammary tumor (MMT 060562); TRI cells, as described, e.g., in Mather et al., Annals N. Y. Acad. Sci. 383:44-68 (1982); MRC 5 cells; and FS4 cells. Other useful mammalian host cell lines include Chinese hamster ovary (CHO) cells, including DHFK CHO cells (Urlaub et al., Proc. Natl. Acad. Sci. USA 77:42 16 (1980)); and myeloma cell lines such as YO, NSO and Sp2/0. For a review of certain mammalian host cell lines suitable for antibody or antibody derivative production, see, e.g., Yazaki and Wu, Methods in Molecular Biology, Vol. 248 (B. K. C. Lo, ed., Humana Press, Totowa, NJ), pp. 255-268 (2003).

In certain embodiments, techniques for making bispecific and/or multispecific antibodies include, but are not limited to, recombinant expression of two immunoglobulin heavy chain-light chain pairs having the same specificity, where one or two of the heavy chains or the light chains are fuse to an antigen binding moiety (e.g., a VHH or scFv) having a different specificity, recombinant coexpression of two immunoglobulin heavy chain-light chain pairs having different specificities (see Milstein and Cuello, Nature 305: 537 (1983)), PCT Patent Application No. WO 93/08829, and Traunecker et al., EMBO J 10: 3655 (1991)), and "knobin-hole" engineering (see, e.g., U.S. Pat. No. 5,731,168). Bispecific antibodies can also be made by engineering electrostatic steering effects for making antibody Fc-heterodimeric molecules (WO 2009/089004A 1); cross-linking two or more antibodies or fragments (see, e.g., U.S. Pat. No. 4,676,980, and Brennan et al., Science, 229: 81 (1985)); using leucine zippers to produce bi specific antibodies (see, e.g., Kostelny et al., J Immunol., 148(5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J Immunol. 147: 60 (1991).

Bispecific and multispecific molecules of the present disclosure can also be made using chemical techniques (see, e.g., Kranz (1981) Proc. Natl. Acad. Sci. USA 78:5807), "polydoma" techniques (see, e.g., U.S. Pat. No. 4,474,893), or recombinant DNA techniques. Bispecific and multispecific molecules of the presently disclosed subject matter can also be prepared by conjugating the constituent binding specificities, e.g., a first epitope and a second epitope binding specificities, using methods known in the art and as described herein. For example, and not by way of limitation, each binding specificity of the bispecific and multispecific molecule can be generated together by recombinant fusion protein techniques, or can be generated separately and then conjugated to one another. When the binding specificities are proteins or peptides, a variety of coupling or cross-linking agents can be used for covalent conjugation. Non-limiting examples of cross-linking agents include protein A, carbodiimide, N-succinimidyl-S-acetyl-thioacetate (SATA), N-succinimidyl-3-(2-pyridyldithio)propionate (SPDP), and sulfosuccinimidyl 4-(N-maleimidomethyl) cyclohaxane-1-carboxylate (sulfo-SMCC) (see, e.g., Karpovsky (1984) J. Exp. Med. 160:1686; Liu (1985) Proc. Natl. Acad. Sci. USA 82:8648). Other methods include those described by Paulus (Behring Ins. Mitt. (1985) No. 78, 1 18-132; Brennan (1985) Science 229:81-83), Glennie (1987) J Immunol. 139: 2367-2375). When the binding specificities are antibodies (e.g., two humanized antibodies), they can be conjugated via sulfhydryl bonding of the C-terminus hinge regions of the two heavy chains. In certain embodiments, the hinge region can be modified to contain an odd number of sulfhydryl residues, e.g., one, prior to conjugation.

In certain embodiments, both binding specificities of a bispecific antibody can be encoded in the same vector and expressed and assembled in the same host cell. This method is particularly useful where the bispecific and multispecific molecule is a MAb×MAb, MAb×Fab, Fab×F(ab')2 or ligand x Fab fusion protein. In certain embodiments, a bispecific antibody of the present disclosure can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or can comprise at least two single chain molecules. Methods for preparing bi- and multispecific molecules are described, for example, in U.S. Pat. Nos. 5,260,203; 5,455,030; 4,881,175; 5,132,405; 5,091,513; 5,476,786; 5,013,653; 5,258,498; and 5,482,858. Engineered antibodies with three or more functional antigen binding sites (e.g., epitope binding sites) including "Octopus antibodies," are also included herein (see, e.g., US 2006/0025576A1).

In certain embodiments, an animal system can be used to produce an antibody or antibody derivative of the present disclosure. One animal system for preparing hybridomas is the murine system.

Hybridoma production in the mouse is a very well-established procedure. Immunization protocols and techniques for isolation of immunized splenocytes for fusion are known in the art. Fusion partners (e.g., murine myeloma cells) and fusion procedures are also known (see, e.g., Harlow and Lane (1988), Antibodies, A Laboratory Manual, Cold Spring Harbor Laboratory Press, Cold Spring Harbor New York).

2.10 Assays

The antibodies and antibody derivatives of the present disclosure provided herein can be identified, screened for, or characterized for their physical/chemical properties and/or biological activities by various assays known in the art and provided herein.

In certain embodiments, an antibody or antibody derivative of the present disclosure can be tested for its antigen binding activity by known methods, such enzyme-linked immunosorbent assay (ELISA), a radioimmunoassay (RIA), or a Western Blot Assay. Each of these assays generally detects the presence of protein-antibody complexes of particular interest by employing a labeled reagent (e.g., an antibody) specific for the complex of interest. For example, the antibody or antibody derivative can be detected using, e.g., an enzyme-linked antibody or antibody fragment which recognizes and specifically binds to the antibody or antibody derivative. Alternatively, the antibody or antibody derivative can be detected using any of a variety of other immunoassays. For example, the antibody or antibody derivative can be radioactively labeled and used in a radioimmunoassay (RIA) (see, for example, Weintraub, B., Principles of Radioimmunoassays, Seventh Training Course on Radioligand Assay Techniques, The Endocrine Society, March 1986, which is incorporated by reference herein). The radioactive isotope can be detected by such means as the use of a Geiger counter or a scintillation counter or by autoradiography.

In certain embodiments, competition assays can be used to identify an antibody or antibody derivative that competes with an antibody of the present disclosure for binding to GARP/TGFβ complex. In certain embodiments, such a competing antibody binds to the same epitope (e.g., a linear or a conformational epitope) that is bound by an antibody disclosed herein. Detailed exemplary methods for mapping an epitope to which an antibody binds are provided in Morris (1996) "Epitope Mapping Protocols," in Methods in Molecular Biology vol. 66 (Humana Press, Totowa, NJ).

In a non-limiting example of a competition assay, immobilized GARP/TGFβ complex can be incubated in a solution comprising a first labeled antibody or antibody derivative that binds to GARP/TGFβ complex and a second unlabeled antibody that is being tested for its ability to compete with the first antibody for binding to GARP/TGFβ complex. The second antibody may be present in a hybridoma supernatant. As a control, immobilized GARP/TGFβ complex is incubated in a solution comprising the first labeled antibody but not the second unlabeled antibody. After incubation under conditions permissive for binding of the first antibody to GARP/TGFβ complex, excess unbound antibody is removed, and the amount of label associated with immobilized GARP/TGFβ complex is measured. If the amount of label associated with immobilized GARP/TGFβ complex is substantially reduced in the test sample relative to the control sample, then that indicates that the second antibody is competing with the first antibody for binding to GARP/

TGFβ complex. See Harlow and Lane (1988) Antibodies: A Laboratory Manual ch. 14 (Cold Spring Harbor Laboratory, Cold Spring Harbor, NY).

The present disclosure provides assays for identifying anti-GARP/TGFβ antibodies or antibody derivatives thereof having biological activity. Biological activity may include, e.g., activating an immune cell or an immune activation reporter, e.g., a NFAT reporter or a NF-κB reporter. Antibodies having such biological activity in vivo and/or in vitro are also provided.

2.11 Immunoconjugates

The presently disclosed subject matter further provides immunoconjugates comprising an antibody or antibody derivative, disclosed herein, conjugated to one or more detection probe and/or cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes. For example, an antibody or antigen-binding portion of the disclosed subject matter can be functionally linked (e.g., by chemical coupling, genetic fusion, noncovalent association or otherwise) to one or more other binding molecules, such as another antibody, antibody fragment, peptide or binding mimetic.

In certain embodiments, an immunoconjugate is an antibody drug conjugate (ADC) in which an antibody is conjugated to one or more drugs, including but not limited to a maytansinoid (see U.S. Pat. Nos. 5,208,020, 5,416,064 and European Patent EP 0 425 235); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J Med. Chem. 45:4336-4343 (2002); and U.S. Pat. No. 6,630,579); methotrexate; vindesine; ataxane such as docetaxel, paclitaxel, larotaxel, tesetaxel, and ortataxel; a trichothecene; and CC1065.

In certain embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In certain embodiments, an immunoconjugate comprises an antibody as described herein conjugated to a radioactive atom to form a radioconjugate. A variety of radioactive isotopes are available for the production of radioconjugates. Non-limiting examples include $At^{211}$, $I^{131}$, $I^{125}$, $Y^{90}$, $Re^{186}$, $Re^{188}$, $Sm^{53}$, $Bi^{212}$, $P^{32}$, $Pb^{212}$ and radioactive isotopes of Lu. When the radioconjugate is used for detection, it can include a radioactive atom for scintigraphic studies, for example tc99m or 1123, or a spin label for nuclear magnetic resonance (NMR) imaging (also known as magnetic resonance imaging, MRI), such as iodine-123, iodine-131, indium-11, fluorine-19, carbon-13, nitrogen-15, oxygen-17, gadolinium, manganese or iron.

Conjugates of an antibody and cytotoxic agent can be made using a variety of bi functional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-4-labeled 1-isothiocyanatobenzyl-3-methyldiethylene triaminepentaacetic acid (MX-DTPA) is an exemplary chelating agent for conjugation of radionucleotide to the antibody. See WO94/11026. The linker can be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-1 31 (1992); U.S. Pat. No. 5,208,020) can be used.

The immunoconjugates or ADCs herein expressly contemplate, but are not limited to, such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

2.12 Antigen-Recognizing Receptor

The presently disclosed subject matter further provides antigen-recognizing receptors comprising an antibody or antibody fragment disclosed herein. An antigen-recognizing receptor is a receptor that is capable of activating, stimulating or inhibiting an immunoresponsive cell (e.g., a T-cell) in response to its binding to an antigen. Non-limiting examples of antigen-recognizing receptors include native and recombinant T cell receptors (TCRs), a chimeric co-stimulating receptor (CCRs), a chimeric antigen receptor (CARs) and an inhibitory CAR (iCARs). Antigen-recognizing receptor designs and methods of use are well known in the art, and is described in the literature, e.g., International Publications WO 2018/027155, WO 2019/099483, WO 2019/157454, WO 2019/133969, WO 2019/099993, WO 2015/142314, WO 2018/027197 and WO 2014055668.

In certain embodiments, the presently disclosed subject matter provides chimeric antigen receptors (CARs) comprising an antibody or antibody fragment disclosed herein. CARs are engineered receptors, which can graft or confer a specificity of interest onto an immune effector cell. In certain embodiments, a CAR can be used to graft the specificity of a monoclonal antibody onto a T cell; with transfer of its coding sequence facilitated by a vector. In certain embodiments, the CAR is a "First generation" CAR, which is typically composed of an extracellular antigen-binding domain (e.g., a scFv or a VHH) fused to a transmembrane domain, which is fused to cytoplasmic/intracellular signaling domain. "First generation" CARs can provide de novo antigen recognition and cause activation of an immunoresponsive cell, e.g., CD4+ and CD8+ T cells, through their CD3z chain signaling domain in a single fusion molecule, independent of HLA-mediated antigen presentation. In certain embodiments, the CAR is a "Second generation" CAR, which further comprises an intracellular signaling domain from various co-stimulatory molecules (e.g., CD28, 4-1BB, ICOS, 0X40, CD27, CD40/My88 and NKGD2) to the cytoplasmic tail of the CAR to provide additional signals to the immunoresponsive cell, whereby the "Second generation" CAR comprise those that provide both co-stimulation (e.g., CD28 or 4-1BB) and activation (CD3z). In certain embodiments, the CAR is a "Third generation" CAR, which comprises multiple co-stimulation domains (e.g., CD28 and 4-1BB) and activation (CD3z). In certain embodiments, the CAR is a second-generation CAR. In certain embodiments, the CAR comprises an extracellular antigen-binding domain that binds to an antigen, a transmembrane domain, and an intracellular signaling domain, wherein the intracellular signaling domain comprises a co-stimulatory signaling domain. In certain embodiments, the CAR further comprises a hinger/spacer region between the extracellular antigen-binding domain and the transmembrane domain. In certain embodiments, the extracellular antigen-binding domain comprises an antibody or antibody fragment disclosed herein. In certain embodiments, the antibody or antibody fragment comprises a VHH, a Fab or a scFv.

In certain embodiments, the presently disclosed subject matter provides recombinant TCRs comprising an antibody or antibody fragment disclosed herein. A native TCR is a protein complex comprising a disulfide-linked heterodimeric protein consisting of two variable chains expressed as part of a complex with CD3 chain molecules. A native TCR is found on the surface of T cells, and is responsible for recognizing antigens as peptides bound to major histocompatibility complex (MHC) molecules. In certain embodiments, a native TCR comprises an alpha chain and a beta chain (encoded by TRA and TRB genes, respectively). In certain embodiments, a TCR comprises a gamma chain and a delta chain (encoded by TRG and TRD genes, respectively). Each of the alpha chain, the beta chain, the gamma chain and the delta chain comprises two extracellular domains: a Variable (V) region and a Constant (C) region. The Constant region is proximal to the cell membrane, followed by a transmembrane region and a short cytoplasmic tail. The Variable region binds to the peptide/MHC complex. Each variable region has three complementarity determining regions (CDRs). In certain embodiments, a TCR comprises a receptor complex with CD3δ, CD3γ, CD3ε and CD3ζ. When a TCR complex engages with its antigen and MHC (peptide/MHC), the T cell expressing the TCR complex is activated.

In certain embodiments, a recombinant TCR is a non-naturally occurring TCR. In certain embodiments, the recombinant TCR comprises a recombinant alpha chain and/or a recombinant b chain, wherein a part or the entire variable region of the recombinant alpha chain and/or the recombinant b chain is replaced by an antibody or an antibody fragment disclosed herein. In certain embodiments, the antibody or antibody fragment comprises a VHH, a VH, a VL or a scFv. In certain embodiments, the antibody or antibody fragment comprises a VHH. In certain embodiments, the recombinant TCR binds to an antigen of interest in an MHC/HLA-independent manner. In certain non-limiting embodiments, binding of the antigen is capable of activating an immunoresponsive cell comprising the recombinant TCR.

The presently disclosed subject matter provides immunoresponsive cells comprising (a) an antigen-recognizing receptor (e.g., CAR or TCR) disclosed herein. In certain embodiments, the antigen-recognizing receptor is capable of activating the immunoresponsive cell. The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, helper T cells, cytotoxic T cells, memory T cells (including central memory T cells, stem-cell-like memory T cells (or stem-like memory T cells), and two types of effector memory T cells: e.g., TEM cells and TEMRA cells, Regulatory T cells (also known as suppressor T cells), Natural killer T cells, Mucosal associated invariant T cells, and gd T cells. Cytotoxic T cells (CTL or killer T cells) are a subset of T lymphocytes capable of inducing the death of infected somatic or tumor cells. A patient's own T cells may be genetically modified to target specific antigens through the introduction of an antigen recognizing receptor, e.g., a CAR or a TCR. In certain embodiments, the immunoresponsive cell is a T cell. The T cell can be a CD4+ T cell or a CD8+ T cell. In certain embodiments, the T cell is a CD4+ T cell. In certain embodiments, the T cell is a CD8+ T cell. Natural killer (NK) cells can be lymphocytes that are part of cell-mediated immunity and act during the innate immune response. NK cells do not require prior activation in order to perform their cytotoxic effect on target cells. Types of human lymphocytes of the presently disclosed subject matter include, without limitation, peripheral donor lymphocytes, e.g., those disclosed in Sadelain, M., et al. 2003 Nat Rev Cancer 3:35-45 (disclosing peripheral donor lymphocytes genetically modified to express CARs), in Morgan, R. A., et al. 2006 Science 314: 126-129 (disclosing peripheral donor lymphocytes genetically modified to express a full-length tumor antigen-recognizing T cell receptor complex comprising the a and b heterodimer), in Panelli, M. C., et al. 2000 J Immunol 164:495-504; Panelli, M. C., et al. 2000 J Immunol 164:4382-4392 (disclosing lymphocyte cultures derived from tumor infiltrating lymphocytes (TILs) in tumor biopsies), and in Dupont, J., et al. 2005 Cancer Res 65:5417-5427; Papanicolaou, G. A., et al. 2003 Blood 102:2498-2505 (disclosing selectively in vitro-expanded antigen-specific peripheral blood leukocytes employing artificial antigen-presenting cells (AAPCs) or pulsed dendritic cells). In certain embodiments, the immunoresponsive cells (e.g., T cells) can be autologous, non-autologous (e.g., allogeneic), or derived in vitro from engineered progenitor or stem cells.

3. Methods of Use

The presently disclosed subject matter further provides methods for using the disclosed antibodies and antibody derivatives. In certain embodiments, the methods are directed to therapeutic uses of a presently disclosed antibody or antibody derivative. In certain embodiments, the methods are directed to diagnostic use of a presently disclosed antibody or antibody derivative.

3.1 Treatment Methods

The present disclosure provides methods and use of an antibody or antibody derivative disclosed herein for treatment of diseases and disorders or for increasing an immune response. In certain embodiments, the antibody, antibody derivative or pharmaceutical compositions comprising the same disclosed herein can be administered to subjects (e.g., mammals such as humans) to treat diseases and disorders or to increases an immune response. In certain embodiments, the diseases and disorders involve Treg-mediated immune suppression and/or abnormal GARP/TGFβ activity. In certain embodiments, the diseases and disorders that can be treated by an antibody or antibody derivative disclosed herein include, but are not limited to, neoplasia, e.g., cancer.

In certain embodiments, the present disclosure provides an antibody or antibody derivative described herein (or fragments thereof) for use in the manufacture of a medicament. In certain embodiments, the present disclosure provides antibody or antibody derivative described herein (or fragments thereof) for use in the manufacture of a medicament for treating of cancer. In certain embodiments, the present disclosure provides an antibody or antibody derivative described herein (or fragments thereof) for use in treating cancer in a subject. In certain embodiments, the present disclosure provides pharmaceutical compositions comprising an antibody or antibody derivative provided herein (or fragments thereof) for use in treating cancer in a subject. In certain embodiments, the cancer can be blood cancers (e.g. leukemias, lymphomas, and myelomas), ovarian cancer, breast cancer, bladder cancer, brain cancer, colon cancer, intestinal cancer, liver cancer, lung cancer, pancreatic cancer, prostate cancer, skin cancer, stomach cancer, glioblastoma, throat cancer, melanoma, neuroblastoma, adenocarcinoma, glioma, soft tissue sarcoma, and various carcinomas (including prostate and small cell lung cancer). Suitable carcinomas further include any known carcinoma in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolar carcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

In certain embodiments, the cancer can be melanoma, NSCLC, head and neck cancer, urothelial cancer, breast cancer (e.g., triple-negative breast cancer, TNBC), gastric cancer, cholangiocarcinoma, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer or thyroid cancer. In certain embodiments, the cancer exhibits high microsatellite instability (MSI-high). In certain embodiments, the cancer exhibits low microsatellite instability (MSI-low).

In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is suspected of having or at risk of having a cancer or be diagnosed with a cancer or any other disease having abnormal GARP/TGFβ complex expression or activity.

Many diagnostic methods for cancer or any other disease exhibiting abnormal GARP/TGFβ activity and the clinical delineation of those diseases are known in the art. Such methods include, but are not limited to, e.g., immunohistochemistry, PCR, fluorescent in situ hybridization (FISH). Additional details regarding diagnostic methods for abnormal GARP/TGFβ activity or expression are described in, e.g., Gupta et al. (2009) Mod Pathol. 22(1): 128-133; Lopez-Rios et al. (2013) J Clin Pathol. 66(5): 381-385; Ellison et al. (2013) J Clin Pathol 66(2): 79-89; and Guha et al. (2013) PLoS ONE 8(6): e67782.

Administration can be by any suitable route including, e.g., intravenous, intramuscular, or subcutaneous. In some embodiments, the antibody or antibody derivative (or fragments thereof) and/or compositions provided herein are administered in combination with a second, third, or fourth agent (including, e.g., an antineoplastic agent, a growth inhibitory agent, a cytotoxic agent, or a chemotherapeutic agent) to treat the diseases or disorders involving abnormal GARP/TGFβ activity. Such agents include, e.g., an anti-PD1 antibody (e.g., pembrolizumab, nivolumab, serplulimab), docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4, infusional fluorouracil, leucovorin, oxaliplatin, afatinib, gemcitabine, capecitabine, pemetrexed, tivantinib, everolimus, CpG-ODN, rapamycin, lenalidomide, vemurafenib, endostatin, lapatinib, PX-866, Imprime PGG, and irlotinibm. In some embodiments, the antibody or antibody derivative (or fragments thereof) is conjugated to the additional agent.

In certain embodiments, the antibody or antibody derivative (or fragments thereof) and/or compositions provided herein are administered in combination with one or more additional therapies, such as radiation therapy, surgery, chemotherapy, and/or targeted therapy. In certain embodiments, the antibody, antibody derivative (or fragments thereof) and/or compositions provided herein are administered in combination with radiation therapy. In certain embodiments, the combination of an antibody, antibody derivative (or fragment thereof) and/or composition provided herein and radiation therapy is used for treating a neoplasm or cancer disclosed herein.

In certain embodiments, the anti-GARP/TGFβ antibody, antibody derivative (or fragments thereof) and/or compositions provided herein are administered in combination with an anti-PD1 antibody, e.g., serplulimab. In certain embodiments, the anti-GARP/TGFβ antibody and the anti-PD1 antibody are administered concurrently or sequentially. In certain embodiments, the anti-GARP/TGFβ antibody and the anti-PD1 antibody are administered concurrently. In certain embodiments, one or more doses of the anti-PD1 antibody is administered prior to administering the anti-GARP/TGFβ antibody. In certain embodiments, the subject received a complete course of the anti-PD1 antibody therapy prior to administration of the anti-GARP/TGFβ antibody. In certain embodiments, the anti-GARP/TGFβ antibody is administered during a second course of the anti-PD1 antibody therapy. In certain embodiments, the subject received at least one, at least two, at least three, or at least four doses of the anti-PD1 antibody prior to administration of the anti-GARP/TGFβ antibody. In certain embodiments, at least one dose of the anti-PD1 antibody is administered concurrently with the anti-GARP inhibitor. In certain embodiments, one or more doses of the anti-GARP/TGFβ antibody are administered prior to administering the anti-PD1 antibody. In certain embodiments, the subject received at least two, at least three, at least three, or at least four doses of the anti-GARP/TGFβ antibody prior to administration of the anti-PD1 antibody. In certain embodiments, at least one dose of the anti-GARP/TGFβ antibody is administered concurrently with the anti-PD1 antibody. In certain embodiments, the anti-GARP/TGFβ antibody and the anti-PD1 antibody are administered once every 1, 2, 3, 4, or 5 weeks. In certain embodiments, the cancer is recurrent or progressive after a therapy selected from the group consisting of surgery, chemotherapy, radiation therapy and any combination thereof.

Depending on the indication to be treated and factors relevant to the dosing that a physician of skill in the field would be familiar with, the antibody or antibody derivative provided herein will be administered at a dosage that is efficacious for the treatment of that indication while minimizing toxicity and side effects. For the treatment of a cancer, a typical dose can be, for example, in the rage of 0.001 to 1000 g; however, doses below or above this exemplary range are within the scope of the invention. The daily dose can be about 0.1 μg/kg to about 100 mg/kg of total body weight, about 0.1 μg/kg to about 100 μg/kg of total body weight or about 1 μg/kg to about 100 μg/kg of total body weight. As noted above, therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

A pharmaceutical composition comprising an antibody or antibody derivative disclosed herein can be administered one, two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In certain embodiments, the efficacy of treatment is measured by the percentage tumor growth inhibition (% TGI), calculated using the equation $100-(T/C\times100)$, where T is the mean relative tumor volume of the treated tumor, and C is the mean relative tumor volume of a non-treated tumor. In certain embodiments, the % TGI is about 10%, about 20%, about 30%, about 40%, about 50%, about 60%, about 70%, about 80%, about 90%, about 91%, about 92%, about 93%), about 94%), about 95%, or more than 95%.

3.2 Methods of Diagnosis and Imaging

Labeled antibody or antibody derivative can be used for diagnostic purposes to detect, diagnose, or monitor diseases and/or disorders associated with the expression, aberrant expression and/or activity of GARP/TGFβ complex. For example, the antibodies and antibody derivatives provided herein can be used in in situ, in vivo, ex vivo, and in vitro diagnostic assays or imaging assays. Methods for detecting expression of a GARP/TGFβ complex, comprising (a) assaying the expression of the polypeptide in cells (e.g., tissue) or body fluid of an individual using one or more antibody or antibody derivative and (b) comparing the level of gene expression with a standard gene expression level, whereby an increase or decrease in the assayed gene expression level compared to the standard expression level is indicative of aberrant expression.

Additional embodiments provided herein include methods of diagnosing a disease or disorder associated with expression or aberrant expression of GARP/TGFβ complex in an animal (e.g., a mammal such as a human). The methods comprise detecting GARP/TGFβ complex in the mammal. In certain embodiments, diagnosis comprises: (a) administering an effective amount of a labeled antibody or antibody derivative to a mammal (b) waiting for a time interval following the administering for permitting the labeled antibody or antibody derivative to preferentially concentrate at sites in the subject where the GARP/TGFβ complex is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of GARP/TGFβ complex. Background level can be determined by various methods including, comparing the amount of labeled molecule detected to a standard value previously determined for a particular system.

Antibodies and antibody derivatives provided herein can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$I, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{17}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003).

Alternatively, or additionally, one can measure levels of a GARP polypeptide-encoding nucleic acid or mRNA in the cell, e.g., via fluorescent in situ hybridization using a nucleic acid based probe corresponding to an GARP-encoding nucleic acid or the complement thereof, (FISH; see WO98/45479 published October, 1998), Southern blotting, Northern blotting, or polymerase chain reaction (PCR) techniques, such as real time quantitative PCR (RT-PCR). One can also study GARP/TGFβ complex overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the body cells can be evaluated, e.g., by external scanning for radioactivity or by analyzing a sample (e.g., a biopsy or other biological sample) taken from a mammal previously exposed to the antibody.

4. Pharmaceutical Formulations

The presently disclosed subject matter further provides pharmaceutical formulations containing an antibody or antibody derivative disclosed herein, with a pharmaceutically acceptable carrier. In certain embodiments, the pharmaceutical compositions can include a combination of multiple (e.g., two or more) antibodies and/or antibody derivatives of the presently disclosed subject matter.

In certain embodiments, the disclosed pharmaceutical formulations can be prepared by combining an antibody or antibody derivative having the desired degree of purity with one or more optional pharmaceutically acceptable carriers (Remington's Pharmaceutical Sciences 16th edition, Osol, A. Ed. (1980)), in the form of lyophilized formulations or aqueous solutions. For example, but not by way of limitation, lyophilized antibody formulations are described in U.S. Pat. No. 6,267,958. In certain embodiments, aqueous antibody formulations can include those described in U.S. Pat. No. 6,171,586 and WO2006/044908, the latter formulations including a histidine-acetate buffer. In certain embodiments, the antibody or antibody derivative can be of a purity greater than about 80%, greater than about 90%, greater than about 91%, greater than about 92%, greater than about 93%, greater than about 94%, greater than about 95%, greater than about 96%, greater than about 97%, greater than about 98%, greater than about 99%, greater than about 99.1%, greater than about 99.2%, greater than about 99.3%, greater than about 99.4%, greater than about 99.5%, greater than about 99.6%, greater than about 99.7%, greater than about 99.8% or greater than about 99.9%.

Pharmaceutically acceptable carriers are generally nontoxic to recipients at the dosages and concentrations employed, and include, but are not limited to: buffers such as phosphate, citrate, and other organic acids, antioxidants including ascorbic acid and methionine, preservatives (such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol), low molecular weight (less than about 10 residues) polypeptides, proteins, such as serum albumin, gelatin, or immunoglobulins, hydrophilic polymers such as polyvinylpyrrolidone, amino acids such as glycine, glutamine, asparagine, histidine, arginine, or lysine, monosaccharides, disaccharides, and other carbohydrates including glucose, mannose, or dextrins, chelating agents such as EDTA, sugars such as sucrose, mannitol, trehalose or sorbitol, salt-forming counter-ions such as sodium, metal complexes (e.g., Zn-protein complexes), and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In certain embodiments, a sHASEGP is combined with one or more additional glycosaminoglycanases such as chondroitinases.

The carrier can be suitable for intravenous, intramuscular, subcutaneous, parenteral, spinal or epidermal administration (e.g., by injection or infusion). Depending on the route of administration, the active compound, e.g., an anti-GARP/TGFβ antibody, can be coated in a material to protect the compound from the action of acids and other natural conditions that may inactivate the compound.

Pharmaceutical compositions of the present disclosure also can be administered in combination therapy, i.e., combined with other agents. In certain embodiments, pharmaceutical compositions disclosed herein canal so contain more than one active ingredient as necessary for the particular indication being treated, for example, those with complementary activities that do not adversely affect each other. In certain embodiments, the pharmaceutical formulation can include a second active ingredient for treating the same disease treated by the first therapeutic. Such active ingredients are suitably present in combination in amounts that are effective for the purpose intended. For example, and not by way of limitation, the formulation of the present disclosure can also contain more than one active ingredient as necessary for the particular indication being treated, preferably those with complementary activities that do not adversely affect each other. For example, it may be desirable to further provide a second therapeutic useful for treatment of the same disease. Such active ingredients are suitably present in combination in amounts that are effective for the purpose intended.

A composition of the present disclosure can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, 1978. In certain embodiments, the pharmaceutical compositions are manufactured under Good Manufacturing Practice (GMP) conditions of the U.S. Food and Drug Administration.

Sustained-release preparations containing an antibody or antibody derivative disclosed herein can also be prepared. Suitable examples of sustained-release preparations include semipermeable matrices of solid hydrophobic polymers containing the antibody or antibody derivative, which matrices are in the form of shaped articles, e.g. films, or microcapsules. In certain embodiments, active ingredients can be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

To administer an antibody or antibody derivative of the present disclosure by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J Neuroimmunol. 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

Except insofar as any conventional media or agent is incompatible with the active compound, use thereof in the pharmaceutical compositions of the present disclosure is contemplated. Supplementary active compounds can also be incorporated into the compositions.

Therapeutic compositions typically must be sterile, substantially isotonic, and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating one or more antibody or antibody derivative disclosed herein in the required amount in an appropriate solvent with one or a combination of ingredients enumerated above, as required, followed by sterilization microfiltration, e.g., by filtration through sterile filtration membranes. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Therapeutic compositions can also be administered with medical devices known in the art. For example, a therapeutic composition of the present disclosure can be administered with a needleless hypodermic injection device, such as the devices disclosed in, e.g., U.S. Pat. Nos. 5,399,163, 5,383,851, 5,312,335, 5,064,413, 4,941,880, 4,790,824 or 4,596,556. Examples of implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known.

For the therapeutic compositions, formulations of the present disclosure include those suitable for oral, nasal, topical (including buccal and sublingual), rectal, vaginal and/or parenteral administration. The formulations can conveniently be presented in unit dosage form and may be prepared by any methods known in the art of pharmacy. The amount of antibody or antibody derivative, which can be combined with a carrier material to produce a single dosage form, vary depending upon the subject being treated, and the particular mode of administration. The amount of the antibody or antibody derivative which can be combined with a carrier material to produce a single dosage form generally be that amount of the composition which produces a therapeutic effect. Generally, out of one hundred percent, this amount range from about 0.01 percent to about ninety-nine percent of active ingredient, from about 0.1 percent to about 70 percent, or from about 1 percent to about 30 percent.

Dosage forms for the topical or transdermal administration of compositions of the present disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These pharmaceutical compositions can also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In certain embodiments, when an antibody or antibody derivative of the present disclosure are administered as pharmaceuticals, to humans and animals, they can be given alone or as a pharmaceutical composition containing, for example, from about 0.01% to about 99.5% (or about 0.1% to about 90%) of the antibody or antibody derivative in combination with a pharmaceutically acceptable carrier.

5. Articles of Manufacture

The presently disclosed subject matter further provides articles of manufacture, e.g., kits, containing materials useful for the treatment, prevention and/or diagnosis of the disorders described above.

In certain embodiments, the article of manufacture/kit includes a container and a label or package insert on or associated with the container. Non limiting examples of suitable containers include bottles, vials, syringes, IV solution bags, etc. The containers can be formed from a variety of materials such as glass or plastic. The container can hold a composition which is by itself or combined with another composition effective for treating, preventing and/or diagnosing the condition and may have a sterile access port (for example, the container may be an intravenous solution bag or a vial having a stopper pierceable by a hypodermic injection needle).

In certain embodiments, at least one active agent in the composition is an antibody or antibody derivative of the present disclosure. The label or package insert can indicate that the composition is used for treating the condition of choice.

In certain embodiments, the article of manufacture/kit can comprise (a) a first container with a composition contained therein, wherein the composition comprises an antibody or antibody derivative of the present disclosure; and (b) a second container with a composition contained therein, wherein the composition comprises a further cytotoxic or otherwise therapeutic agent. In certain embodiments, the article of manufacture/kit can further comprise a package insert indicating that the compositions can be used to treat a particular condition.

Alternatively, or additionally, the article of manufacture/kit can further an additional container, e.g., a second or third container, including a pharmaceutically acceptable buffer, such as, but not limited to, bacteriostatic water for injection (BWFI), phosphate-buffered saline, Ringer's solution and dextrose solution. The article of manufacture/kit can include other materials desirable from a commercial and user standpoint, including other buffers, diluents, filters, needles, and syringes.

SEQUENCE TABLE

| SEQ ID NO | NAME | AMINO ACID SEQUENCE |
|---|---|---|
| 1. | Clone GA1 VH CDR1 | SYAMH |
| 2. | Clone GA1 VH CDR2 | VISYDGSNKYYADSVKG |
| 3. | Clone GA1 VH CDR3 | DVLRTYYYYGMDV |
| 4 | Clone GA1 VL CDR1 | SGDALPDRYTY |
| 5. | Clone GA1 VL CDR2 | SDNERPS |
| 6. | Clone GA1 VL CDR3 | QSADDTYT |
| 7. | Clone GA1 VH | QVQLVQSGGGVVQPGRSLRLSCAASGFTFSSYAMHQVRQAP<br>GKGLEWVAVISYDGSNKYYADSVKGRFTISRDNSKNTLYLQ<br>MNSLRAEDTAVYYCARDVLRTYYYYGMDVWGQGTTVTVSS |
| 8. | Clone GA1 VL | LSYELTQPPSVSVFPGQTARITCSGDALPDRYTYWYQQKPGQ<br>APVLVIYSDNERPSGIPERFSGSSSGTIATLTINGVQAEDEADY<br>YCQSADDTYTFGGGTKLTVLGQP |
| 9. | Clone GA1 HC | QVQLVQSGGGVVQPGRSLRLSCAASGFTFSSYAMHQVRQAP<br>GKGLEWVAVISYDGSNKYYADSVKGRFTISRDNSKNTLYLQ<br>MNSLRAEDTAVYYCARDVLRTYYYYGMDVWGQGTTVTVSS<br>ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKKVEPKSCDKTHTCPPCPAPELLGGPSVFLFPPK<br>PKDTLMISRTPEVTCVVVDVSHEDPEVKFNWYVDGVEVHNA<br>KTKPREEQYNSTYRVVSVLTVLHQDWLNGKEYKCKVSNKAL<br>PAPIEKTISKAKGQPREPQVYTLPPSRDELTKNQVSLTCLVKGF |

-continued

| SEQ ID NO | NAME | AMINO ACID SEQUENCE |
|---|---|---|
| | | YPSDIAVEWESNGQPENNYKTTPPVLDSDGSFFLYSKLTVDKS RWQQGNVFSCSVMHEALHNHYTQKSLSLSPGK |
| 10. | Clone GA1 LC | LSYELTQPPSVSVFPGQTARITCSGDALPDRYTYWYQQKPGQ APVLVIYSDNERPSGIPERFSGSSSGTIATLTINGVQAEDEADY YCQSADDTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 11. | Clone GA1#4 VH CDR1 | SYAMH |
| 12. | Clone GA1#4 VH CDR2 | TISYDGSNKIYADSVKG |
| 13. | Clone GA1#4 VH CDR3 | DSLRTYYYTGMDV |
| 14. | Clone GA1#4 VL CDR1 | SGDALPDRYTY |
| 15. | Clone GA1#4 VL CDR2 | SDNERPV |
| 16. | Clone GA1#4 VL CDR3 | QSSDDTYT |
| 17. | Clone GA1#4 VH | QVQLVQSGGGVVQPGRSLRLSCAASGFTFSSYAMHQVRQAP GKGLEWVATISYDGSNKIYADSVKGRFTISRDNSKNTLYLQM NSLRAEDTAVYYCARDSLRTYYYTGMDVWGQGTTVTVSS |
| 18. | Clone GA1#4 VL | LSYELTQPPSVSVFPGQTARITCSGDALPDRYTYWYQQKPGQ APVLVIYSDNERPVGIPERFSGSSSGTIATLTINGVQAEDEADY YCQSSDDTYTFGGGTKLTVLGQP |
| 19. | Clone GA1#4 HC | QVQLVQSGGGVVQPGRSLRLSCAASGFTFSSYAMHQVRQAP GKGLEWVATISYDGSNKIYADSVKGRFTISRDNSKNTLYLQM NSLRAEDTAVYYCARDSLRTYYYTGMDVWGQGTTVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCDKTHTCPPCPAPELLGGPSVFLFPPKPKD TLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSREEMTKNQVSLTCLVKGFYPS DIAVEWESNGQPENNYKTTPPVLDSDGSFFLYSKLTVDKSRW QQGNVFSCSVMHEALHNHYTQKSLSLSPG |
| 20. | Clone GA1#4 LC | LSYELTQPPSVSVFPGQTARITCSGDALPDRYTYWYQQKPGQ APVLVIYSDNERPVGIPERFSGSSSGTIATLTINGVQAEDEADY YCQSSDDTYTFGGGTKLTVLGQPKAAPSVTLFPPSSEELQANK ATLVCLISDFYPGAVTVAWKADSSPVKAGVETTTPSKQSNNK YAASSYLSLTPEQWKSHKSYSCQVTHEGSTVEKTVAPTECS |
| 21. | Clone GA1#6 VH CDR1 | SYAMH |
| 22. | Clone GA1#6 VH CDR2 | SISYDGSNVYYADSVKG |
| 23. | Clone GA1#6 VH CDR3 | DVLRTYYYMGMDV |
| 24. | Clone GA1#6 VL CDR1 | SGDALPDRYTY |
| 25. | Clone GA1#6 VL CDR2 | SDNERPV |
| 26. | Clone GA1#6 VL CDR3 | QSSDDTYT |

-continued

SEQUENCE TABLE

| SEQ ID NO | NAME | AMINO ACID SEQUENCE |
|---|---|---|
| 27. | Clone GA1#6 VH | QVQLVQSGGGVVQPGRSLRLSCAASGFTFSSYAMHQVRQAP GKGLEWVASISYDGSNVYYADSVKGRFTISRDNSKNTLYLQM NSLRAEDTAVYYCARDVLRTYYYMGMDVWGQGTTVTVSS |
| 28. | Clone GA1#6 VL | LSYELTQPPSVSVFPGQTARITCSGDALPDRYTYWYQQKPGQ APVLVIYSDNERPVGIPERFSGSSSGTIATLTINGVQAEDEADY YCQSSDDTYTFGGGTKLTVLGQP |
| 29. | Clone GA1#6 HC | QVQLVQSGGGVVQPGRSLRLSCAASGFTFSSYAMHQVRQAP GKGLEWVASISYDGSNVYYADSVKGRFTISRDNSKNTLYLQM NSLRAEDTAVYYCARDVLRTYYYMGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPG |
| 30. | Clone GA1#6 LC | LSYELTQPPSVSVFPGQTARITCSGDALPDRYTYWYQQKPGQ APVLVIYSDNERPVGIPERFSGSSSGTIATLTINGVQAEDEADY YCQSSDDTYTFGGGTKLTVLGQPKAAPSVTLFPPSSEELQANK ATLVCLISDFYPGAVTVAWKADSSPVKAGVETTTPSKQSNNK YAASSYLSLTPEQWKSHKSYSCQVTHEGSTVEKTVAPTECS |
| 31. | Clone GA1#7 VH CDR1 | SYAMH |
| 32. | Clone GA1#7 VH CDR2 | VISYDGSQKYYADSVKG |
| 33. | Clone GA1#7 VH CDR3 | DALRTYYYYGMDV |
| 34. | Clone GA1#7 VL CDR1 | SGDALPDRYTY |
| 35. | Clone GA1#7 VL CDR2 | SDNERPS |
| 36. | Clone GA1#7 VL CDR3 | QSSDDTYT |
| 37. | Clone GA1#7 VH | QVQLVQSGGGVVQPGRSLRLSCAASGFTFSSYAMHQVRQAP GKGLEWVAVISYDGSQKYYADSVKGRFTISRDNSKNTLYLQ MNSLRAEDTAVYYCARDALRTYYYYGMDVWGQGTTVTVSS |
| 38. | Clone GA1#7 VL | LSYELTQPPSVSVFPGQTARITCSGDALPDRYTYWYQQKPGQ APVLVIYSDNERPSGIPERFSGSSSGTIATLTINGVQAEDEADY YCQSSDDTYTFGGGTKLTVLGQP |
| 39. | Clone GA1#7 HC | QVQLVQSGGGVVQPGRSLRLSCAASGFTFSSYAMHQVRQAP GKGLEWVAVISYDGSQKYYADSVKGRFTISRDNSKNTLYLQ MNSLRAEDTAVYYCARDALRTYYYYGMDVWGQGTTVTVSS ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPG |
| 40. | Clone GA1#7 LC | LSYELTQPPSVSVFPGQTARITCSGDALPDRYTYWYQQKPGQ APVLVIYSDNERPSGIPERFSGSSSGTIATLTINGVQAEDEADY YCQSSDDTYTFGGGTKLTVLGQPKAAPSVTLFPPSSEELQANK ATLVCLISDFYPGAVTVAWKADSSPVKAGVETTTPSKQSNNK YAASSYLSLTPEQWKSHKSYSCQVTHEGSTVEKTVAPTECS |
| 41. | Clone GA1#8 VH CDR1 | SYAMH |

-continued

| SEQ ID NO | NAME | AMINO ACID SEQUENCE |
|---|---|---|
| 42. | Clone GA1#8 VH CDR2 | SISYDGSNKYYADSVKG |
| 43. | Clone GA1#8 VH CDR3 | DALRTYYYQGMDV |
| 44. | Clone GA1#8 VL CDR1 | SGDALPDRYTY |
| 45. | Clone GA1#8 VL CDR2 | SDNERPR |
| 46. | Clone GA1#8 VL CDR3 | QSADYTYT |
| 47. | Clone GA1#8 VH | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSS |
| 48. | Clone GA1#8 VL | LSYELTQPPSVSVFPGQTARITCSGDALPDRYTYWYQQKPGQ APVLVIYSDNERPRGIPERFSGSSSGTIATLTINGVQAEDEADY YCQSADYTYTFGGGTKLTVLGQP |
| 49. | Clone GA1#8 HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPG |
| 50. | Clone GA1#8 LC | LSYELTQPPSVSVFPGQTARITCSGDALPDRYTYWYQQKPGQ APVLVIYSDNERPRGIPERFSGSSSGTIATLTINGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 51. | Clone GA1#9 VH CDR1 | SYAMH |
| 52. | Clone GA1#9 VH CDR2 | SISYDGSNKYYADSVKG |
| 53. | Clone GA1#9 VH CDR3 | DALRTYYYYGMDV |
| 54. | Clone GA1#9 VL CDR1 | SGDALPDRYTY |
| 55. | Clone GA1#9 VL CDR2 | SDNERPS |
| 56. | Clone GA1#9 VL CDR3 | QSADPTYT |
| 57. | Clone GA1#9 VH | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYYGMDVWGQGTTVTVSS |
| 58. | Clone GA1#9 VL | LSYELTQPPSVSVFPGQTARITCSGDALPDRYTYWYQQKPGQ APVLVIYSDNERPSGIPERFSGSSSGTIATLTINGVQAEDEADY YCQSADPTYTFGGGTKLTVLGQP |
| 59. | Clone GA1#9 HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYYGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH |

SEQUENCE TABLE

-continued

SEQUENCE TABLE

| SEQ ID NO | NAME | AMINO ACID SEQUENCE |
|---|---|---|
| | | KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPG |
| 60. | Clone GA1#9 LC | LSYELTQPPSVSVFPGQTARITCSGDALPDRYTYWYQQKPGQ APVLVIYSDNERPSGIPERFSGSSSGTIATLTINGVQAEDEADY YCQSADPTYTFGGGTKLTVLGQPKAAPSVTLFPPSSEELQANK ATLVCLISDFYPGAVTVAWKADSSPVKAGVETTTPSKQSNNK YAASSYLSLTPEQWKSHKSYSCQVTHEGSTVEKTVAPTECS |
| 61. | Clone GA1#12 VH CDR1 | SYAMH |
| 62. | Clone GA1#12 VH CDR2 | SISYDGSNKAYADSVKG |
| 63. | Clone GA1#12 VH CDR3 | DVLRTYYYAGMDV |
| 64. | Clone GA1#12 VL CDR1 | SGDALPDRYTY |
| 65. | Clone GA1#12 VL CDR2 | LDNERPK |
| 66. | Clone GA1#12 VL CDR3 | QSADDTYT |
| 67. | Clone GA1#12 VH | QVQLVQSGGGVVQPGRSLRLSCAASGFTFSSYAMHQVRQAP GKGLEWVASISYDGSNKAYADSVKGRFTISRDNSKNTLYLQM NSLRAEDTAVYYCARDVLRTYYYAGMDVWGQGTTVTVSS |
| 68. | Clone GA1#12 VL | LSYELTQPPSVSVFPGQTARITCSGDALPDRYTYWYQQKPGQ APVLVIYLDNERPKGIPERFSGSSSGTIATLTINGVQAEDEADY YCQSADDTYTFGGGTKLTVLGQP |
| 69. | Clone GA1#12 HC | QVQLVQSGGGVVQPGRSLRLSCAASGFTFSSYAMHQVRQAP GKGLEWVASISYDGSNKAYADSVKGRFTISRDNSKNTLYLQM NSLRAEDTAVYYCARDVLRTYYYAGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPG |
| 70. | Clone GA1#12 LC | LSYELTQPPSVSVFPGQTARITCSGDALPDRYTYWYQQKPGQ APVLVIYLDNERPKGIPERFSGSSSGTIATLTINGVQAEDEADY YCQSADDTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 71. | Clone GA1#7K HC | QVQLVQSGGGVVQPGRSLRLSCAASGFTFSSYAMHQVRQAP GKGLEWVAVISYDGSQKYYADSVKGRFTISRDNSKNTLYLQ MNSLRAEDTAVYYCARDALRTYYYYGMDVWGQGTTVTVSS ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK |
| 72. | Clone GA1#7K LC | LSYELTQPPSVSVFPGQTARITCSGDALPDRYTYWYQQKPGQ APVLVIYSDNERPSGIPERFSGSSSGTIATLTINGVQAEDEADY YCQSSDDTYTFGGGTKLTVLGQPKAAPSVTLFPPSSEELQANK |

-continued

| SEQ ID NO | NAME | AMINO ACID SEQUENCE |
|---|---|---|
| | | ATLVCLISDFYPGAVTVAWKADSSPVKAGVETTTPSKQSNNK YAASSYLSLTPEQWKSHKSYSCQVTHEGSTVEKTVAPTECS |
| 73. | Clone GA1#7K (LC_FS/IT) HC | QVQLVQSGGGVVQPGRSLRLSCAASGFTFSSYAMHQVRQAP GKGLEWVAVISYDGSQKYYADSVKGRFTISRDNSKNTLYLQ MNSLRAEDTAVYYCARDALRTYYYYGMDVWGQGTTVTVSS ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK |
| 74. | Clone GA1#7K (LC_FS/IT) LC | LSYELTQPPSVSVSPGQTARITCSGDALPDRYTYWYQQKPGQ APVLVIYSDNERPSGIPERFSGSSSGTTATLTINGVQAEDEADY YCQSSDDTYTFGGGTKLTVLGQPKAAPSVTLFPPSSEELQANK ATLVCLISDFYPGAVTVAWKADSSPVKAGVETTTPSKQSNNK YAASSYLSLTPEQWKSHKSYSCQVTHEGSTVEKTVAPTECS |
| 75. | Clone GA1#7 (LC_FS/IT) HC | QVQLVQSGGGVVQPGRSLRLSCAASGFTFSSYAMHQVRQAP GKGLEWVAVISYDGSQKYYADSVKGRFTISRDNSKNTLYLQ MNSLRAEDTAVYYCARDALRTYYYYGMDVWGQGTTVTVSS ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPG |
| 76. | Clone GA1#7 (LC_FS/IT) LC | LSYELTQPPSVSVSPGQTARITCSGDALPDRYTYWYQQKPGQ APVLVIYSDNERPSGIPERFSGSSSGTTATLTINGVQAEDEADY YCQSSDDTYTFGGGTKLTVLGQPKAAPSVTLFPPSSEELQANK ATLVCLISDFYPGAVTVAWKADSSPVKAGVETTTPSKQSNNK YAASSYLSLTPEQWKSHKSYSCQVTHEGSTVEKTVAPTECS |
| 77. | Clone GA1#8K HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 78. | Clone GA1#8K LC | LSYELTQPPSVSVFPGQTARITCSGDALPDRYTYWYQQKPGQ APVLVIYSDNERPRGIPERFSGSSSGTIATLTINGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 79. | Clone GA1#8K (LC_FS/IT) HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 80. | Clone GA1#8K (LC_FS/IT) LC | LSYELTQPPSVSVSPGQTARITCSGDALPDRYTYWYQQKPGQ APVLVIYSDNERPRGIPERFSGSSSGTTATLTINGVQAEDEADY |

-continued

SEQUENCE TABLE

| SEQ ID NO | NAME | AMINO ACID SEQUENCE |
|---|---|---|
| | | YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 81. | Clone GA1#8 (LC_FS/IT) HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPG |
| 82. | Clone GA1#8 (LC_FS/IT) LC | LSYELTQPPSVSVSPGQTARITCSGDALPDRYTYWYQQKPGQ APVLVIYSDNERPRGIPERFSGSSSGTTATLTINGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 83. | Clone GA1#7 (LC_FS/IT) VL | LSYELTQPPSVSVSPGQTARITCSGDALPDRYTYWYQQKPGQ APVLVIYSDNERPSGIPERFSGSSSGTTATLTINGVQAEDEADY YCQSSDDTYTFGGGTKLTVLGQP |
| 84. | Clone GA1#8 (LC_FS/IT) VL | LSYELTQPPSVSVSPGQTARITCSGDALPDRYTYWYQQKPGQ APVLVIYSDNERPRGIPERFSGSSSGTTATLTINGVQAEDEADY YCQSADYTYTFGGGTKLTVLGQP |
| 85. | Clone GA1#8_14 VH | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSS |
| 86. | Clone GA1#8_14 VL | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQP |
| 87. | Clone GA1#8_14 HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVLQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 88. | Clone GA1#8_14 LC | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 89. | Clone GA1#8_17 VH | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSS |
| 90. | Clone GA1#8_17 VL | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQP |
| 91. | Clone GA1#8_17 HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVKQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF |

-continued

| SEQ ID NO | NAME | AMINO ACID SEQUENCE |
|---|---|---|
| | | YPSDIAVEWESNGQPENNYKTTPPVLDSDGSFFLYSKLTVDKS RWQQGNVFSCSVMHEALHNHYTQKSLSLSPGK |
| 92. | Clone GA1#8_17 LC | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 93. | Clone GA1#8_18 VH | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSS |
| 94. | Clone GA1#8_18 VL | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQP |
| 95. | Clone GA1#8_18 HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVDQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 96. | Clone GA1#8_18 LC | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 97. | Clone GA1#8_20 VH | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSS |
| 98. | Clone GA1#8_20 VL | LSYELTQPPSVSVFPGQTARITCSGDALPDRYTYWYQQKPGQ APVLVIYSDNERPRGIPERFSGSSSGTTATLTINGVQAEDEADY YCQSADYTYTFGGGTKLTVLGQP |
| 99. | Clone GA1#8_20 HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG ALTSGVHTFPAVKQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 100. | Clone GA1#8_20 LC | LSYELTQPPSVSVFPGQTARITCSGDALPDRYTYWYQQKPGQ APVLVIYSDNERPRGIPERFSGSSSGTTATLTINGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSKLSLTPEQWKSHKSYSCQVTHEGSTVEKTVAPTECS |
| 101. | Clone GA1#8_21 VH | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSS |
| 102. | Clone GA1#8_21 VL | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQP |
| 103. | Clone GA1#8_21 HC | QVQLVQSGGGVVQPGRSLRLSCAASGFTFSSYAMHQVRQAP GKGLEWVASISYDGSNKYYADSVKGRFTISRDNSKNTLYLQM NSLRAEDTAVYYCARDALRTYYYQGMDVWGQGTTVTVSSA STKGPSVFPLAPSSKSTSGGTAALGCLVKDYFPEPVTVSWNSG |

-continued

SEQUENCE TABLE

| SEQ ID NO | NAME | AMINO ACID SEQUENCE |
|---|---|---|
| | | ALTSGVHTFKAVKQSSGLYSLSSVVTVPSSSLGTQTYICNVNH KPSNTKVDKKVEPKSCDKTHTCPPCPAPELLGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVKGF YPSDIAVEWESNGQPENNYKTTPPVLDSDGSFFLYSKLTVDKS RWQQGNVFSCSVMHEALHNHYTQKSLSLSPGK |
| 104. | Clone GA1#8_21 LC | LSYELTQPPSVSVSPGQTARITCSGDALPDRYTYWYQQKPGQ APVLVIYSDNERPRGIPERFSGSSSGTTATLTITGVQAEDEADY YCQSADYTYTFGGGTKLTVLGQPKAAPSVTLFPPSSEELQAN KATLVCLISDFYPGAVTVAWKADSSPVKAGVETTTPSKQSNN KYAASSYLSLTPEQWKSHKSYSCQVTHEGSTVEKTVAPTECS |
| 105. | Clone hGA17 VH CDR1 | DTYFH |
| 106. | Clone hGA17 VH CDR2 | RIDPTNGNGRYAQKFQG |
| 107. | Clone hGA17 VH CDR3 | STGTGYFALVY |
| 108. | Clone hGA17 VL CDR1 | KASQNVGSAVA |
| 109. | Clone hGA17 VL CDR2 | WSSTRHT |
| 110. | Clone hGA17 VL CDR3 | QQYSNYPLTF |
| 111. | Clone hGA17 VH | QVQLVQSGAEVKKPGASVKVSCKASGFNIKDTYFHWVRQAP GQGLEWMGRIDPTNGNGRYAQKFQGRVTMTRDTSTSTVYME LSSLRSEDTAVYYCATSTGTGYFALVYWGQGTTVTVSS |
| 112. | Clone hGA17 VL | DIQLTQSPSFLSASVGDRVTITCKASQNVGSAVAWYQQKPGK APKLLIYWSSTRHTGVPSRFSGSGSGTEFTLTISSLQPEDFATY YCQQYSNYPLTFGGGTKLEIKRTV |
| 113. | Clone hGA17 HC | QVQLVQSGAEVKKPGASVKVSCKASGFNIKDTYFHWVRQAP GQGLEWMGRIDPTNGNGRYAQKFQGRVTMTRDTSTSTVYME LSSLRSEDTAVYYCATSTGTGYFALVYWGQGTTVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKP REEQYNSTYRVVSVLTVLHQDWLNGKEYKCKVSNKALPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK |
| 114. | Clone hGA17 LC | DIQLTQSPSFLSASVGDRVTITCKASQNVGSAVAWYQQKPGK APKLLIYWSSTRHTGVPSRFSGSGSGTEFTLTISSLQPEDFATY YCQQYSNYPLTFGGGTKLEIKRTVAAPSVFIFPPSDEQLKSGTA SVVCLLNNFYPREAKVQWKVDNALQSGNSQESVTEQDSKDS TYSLSSTLTLSKADYEKHKVYACEVTHQGLSSPVTKSFNRGEC |
| 115. | GARP polypeptide | MRPQILLLLALLTLGLAAQHQDKVPCKMVDKKVSCQVLGLL QVPSVLPPDTETLDLSGNQLRSILASPLGFYTALRHLDLSTNEI SFLQPGAFQALTHLEHLSLAHNRLAMATALSAGGLGPLPRVT SLDLSGNSLYSGLLERLLGEAPSLHTLSLAENSLTRLTRHTFRD MPALEQLDLHSNVLMDIEDGAFEGLPRLTHLNLSRNSLTCISD FSLQQLRVLDLSCNSIEAFQTASQPQAEFQLTWLDLRENKLLH FPDLAALPRLIYLNLSNNLIRLPTGPPQDSKGIHAPSEGWSALP LSAPSGNASGRPLSQLLNLDLSYNEIELIPDSFLEHLTSLCFLNL SRNCLRTFEARRLGSLPCLMLLDLSHNALETLELGARALGSLR TLLLQGNALRDLPPYTFANLASLQRLNLQGNRVSPCGGPDEP GPSGCVAFSGITSLRSLSLVDNEIELLRAGAFLHTPLTELDLSSN PGLEVATGALGGLEASLEVLALQGNGLMVLQVDLPCFICLKR LNLAENRLSHLPAWTQAVSLEVLDLRNNSFSLLPGSAMGGLE TSLRRLYLQGNPLSCCGNGWLAAQLHQGRVDVDATQDLICR |

-continued

SEQUENCE TABLE

| SEQ ID NO | NAME | AMINO ACID SEQUENCE |
|---|---|---|
| | | FSSQEEVSLSHVRPEDCEKGGLKNINLIIILTFILVSAILLTTLAA CCCVRRQKFNQQYKA |
| 116. | GARP polypeptide extracellular domain (ECD) | HQDKVPCKMVDKKVSCQVLGLLQVPSVLPPDTETLDLSGNQ LRSILASPLGFYTALRHLDLSTNEISFLQPGAFQALTHLEHLSL AHNRLAMATALSAGGLGPLPRVTSLDLSGNSLYSGLLERLLG EAPSLHTLSLAENSLTRLTRHTFRDMPALEQLDLHSNVLMDIE DGAFEGLPRLTHLNLSRNSLTCISDFSLQQLRVLDLSCNSIEAF QTASQPQAEFQLTWLDLRENKLLHFPDLAALPRLIYLNLSNNL IRLPTGPPQDSKGIHAPSEGWSALPLSAPSGNASGRPLSQLLNL DLSYNEIELIPDSFLEHLTSLCFLNLSRNCLRTFEARRLGSLPCL MLLDLSHNALETLELGARALGSLRTLLLQGNALRDLPPYTFA NLASLQRLNLQGNRVSPCGGPDEPGPSGCVAFSGITSLRSLSL VDNEIELLRAGAFLHTPLTELDLSSNPGLEVATGALGGLEASL EVLALQGNGLMVLQVDLPCFICLKRLNLAENRLSHLPAWTQA VSLEVLDLRNNSFSLLPGSAMGGLETSLRRLYLQGNPLSCCGN GWLAAQLHQGRVDVDATQDLICRFSSQEEVSLSHVRPEDCEK GGLKNIN |
| 117. | Exemplary linker | GGGGS |
| 118. | Exemplary linker | GSGGSGGSGGSG |
| 119. | Exemplary linker | GGGGSGGGGSGGGGS |
| 120. | Exemplary linker | GGGSG |
| 121. | Exemplary linker | GGGSGGGGSG |
| 122. | Exemplary linker | GGSGGGSG |
| 123. | Exemplary linker | GGSGGGSGGGSG |
| 124. | Exemplary linker | GSGGSG |
| 125. | Exemplary linker | GSGGSGGSG |
| 126. | Exemplary linker | GSGSGSG |
| 127. | Exemplary linker | GGGGSGGGGSGGGGSGGGGSG |
| 128. | Exemplary linker | PAPAP |
| 129. | Exemplary linker | PAPAPPAPAPPAPAP |
| 130. | Exemplary linker | IKRTVAA |
| 131. | Exemplary linker | VSSASTK |
| 132. | Exemplary linker | ASTK |
| 133. | Exemplary linker | ASTKSGGSGGSG |
| 134. | Exemplary linker | AEAAAKA |
| 135. | Exemplary linker | AEAAAKEAAAKA |
| 136. | Exemplary linker | GRPGS GRPGS |
| 137. | Exemplary linker | GRPGS GRPGS GRPGS GRPGS |
| 138. | Exemplary linker | GRGGS GRGGS |
| 139. | Exemplary linker | GRGGS GRGGS GRGGS GRGGS |
| 140. | Exemplary linker | GKPGS GKPGS |
| 141. | Exemplary linker | GKPGS GKPGS GKPGS GKPGS |
| 142. | Exemplary linker | GEPGS GEPGS |
| 143. | Exemplary linker | GEGGS GEGGS GEGGS GEGGS |

-continued

| SEQUENCE TABLE | | |
|---|---|---|
| SEQ ID NO | NAME | AMINO ACID SEQUENCE |
| 144. | Exemplary linker | GDPGS GDPGS |
| 145 | Exemplary linker | GDPGS GDPGS GDPGS GDPGS |

The following examples are merely illustrative of the presently disclosed subject matter and should not be considered as limitations in any way.

EXAMPLES

Example 1. Screening and Testing of Anti-GARP/TGFβ Antibody GA1

Anti-GARP/TGFβ antibody clones were isolated from a naive human Fab phage library synthesized in-house and screened against GARPN-terminal ECD by enzyme linked immunosorbent assay (ELISA) and fluorescent activated cell sorting (FACS). The naive human Fab phage library was generated using PBMC samples isolated from eight healthy donors. The resulting clones were then used to generate full length antibodies by fusing their nucleotide sequences of VL and VH with constant region of human IgG1 using standard assembly PCR techniques. Clone GA1 was identified as the top clone.

Whole cell binding ability of GA1 was tested using transfected CHO-S cells expressing human, cynomolgus and mouse human GARP/TGFβ1 complex as well as activated platelets and Treg cells, which expresses human GARP/latent TGFβ1 on the cell surface. The activation of Treg cells was performed by incubation with anti-CD3/CD28 Dynabead (Gibco) at a cell-to-bead ratio of 1:1 for 24 hrs. The activation of platelets was performed by incubation with thrombin (Sigma) at 1 U/mL for 1 hour. Whole cell binding ability of various antibodies was then tested by incubating the cells with the serially diluted anti-GARP/TGFβ monoclonal antibodies in FACS buffer (1×PBS containing 2% FBS) at 4° C. for a half hour. The cells were washed with FACS buffer, and the binding was detected with goat anti-human IgG(H+L) FITC Ab at 4° C. for another half hour. Flow cytometric analyses were performed using the CytoFLEX platform (Beckman Coulter). Isotype control (bevacizumab) was used as a negative control. GARP ref Ab, an ABBV-151 analog synthesized in-house based on the sequence information disclosed in US 2016/0251438, was used as a positive control. ABBV-151, also known as LHG10.6, is an anti-GARP/TGFβ1 antibody in clinical stage.

Figure 1C:
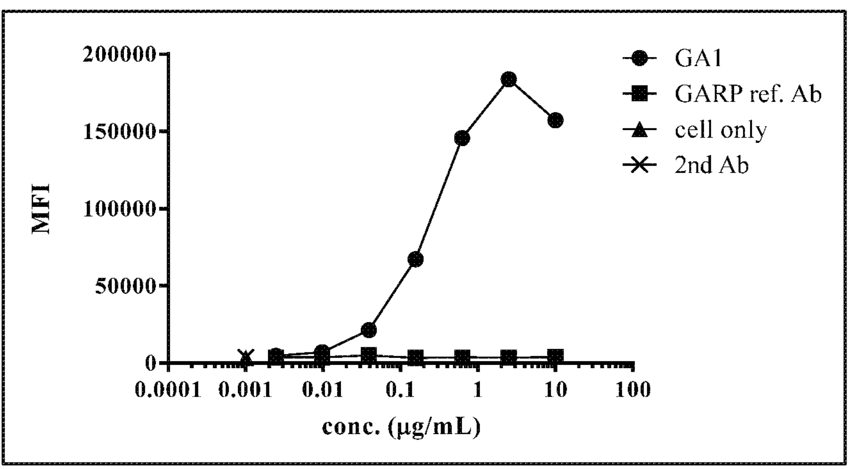
Figure 1D:
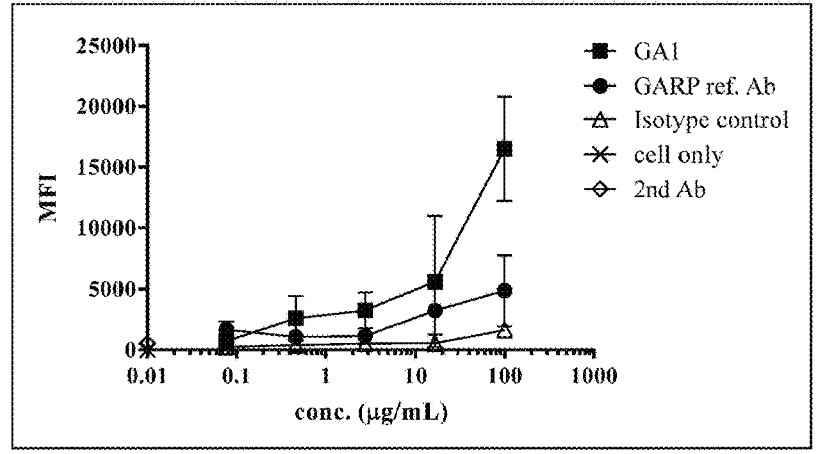
Figure 1E:
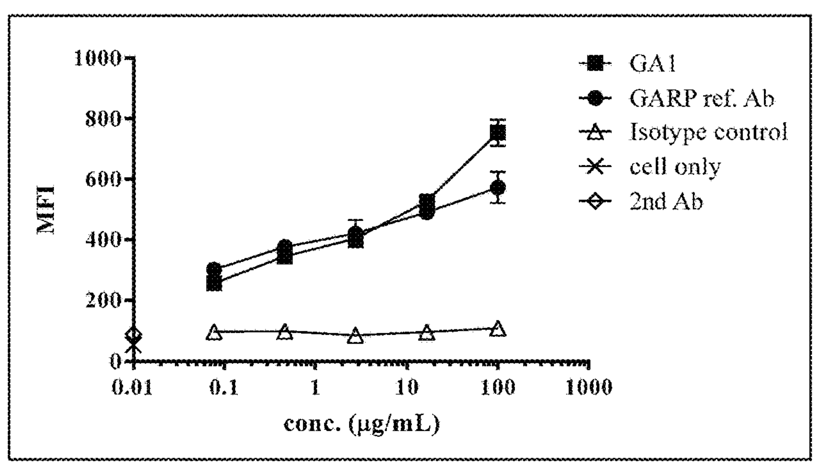

As shown in FIGS. 1A-1E, GA1 bound to human GARP/TGFβ1 complex, cynomolgus GARP/TGFβ1 complex and mouse GARP/TGFβ1 complex expressed on CHO-S cells as well as endogenous human GARP/TGFβ1 complex on thrombin-activated human platelets and activated human Treg cells. In contrast, the ABBV-151 analog was capable of binding to human and cynomolgus GARP/TGFβ1 complex, but was not capable of binding to mouse GARP/TGFβ1 complex as shown in FIG. 1C. The ability to target mouse GARP/TGFβ1 complex in addition to human GARP/TGFβ1 complex gives GA1 an advantage, as its therapeutic efficacy can be tested in various mouse models, which can provide more therapeutic information and guidance prior to entering human clinical trials. Furthermore, as shown in FIGS. 1D and 1E, GA1 exhibited higher binding ability to activated platelets and Treg cells compared to the ABBV-151 analog, indicating an enhanced ability of GA1 to bind to human GARP/TGFβ1 complex.

Next, GA1's ability to inhibit the release of mature TGFβ1 from activated platelets was tested. Platelets were prepared as described as the following. Blood was drawn to a BD vacutainer glass blood collection tubes with acid citrate dextrose (ACD)(BD) and centrifuged for 20 min at 200×g, and the upper layer of platelet-rich plasma was collected. The collected platelet-rich plasma was gently mixed with iso-volume of HEP buffer (140 mM NaCl, 2.7 mM KCl, 3.8 mM HEPES, 5 mM EGTA, pH 7.4) containing 1 μM prostaglandin E1(sigma) and centrifuged for 20 min at 100×g to remove RBC and white blood cells. The supernatant was then transferred to a new tube and the platelets were pelleted down by centrifugation at 800×g for 20 min. The pellet was further rinsed with wash buffer (10 mM sodium citrate, 150 mM NaCl, 1 mM EDTA, 1% (w/v) dextrose, pH 7.4), and resuspended the platelet pellet in Tyrode's buffer (134 mM NaCl, 12 mM $NaHCO_3$, 2.9 mM KCl, 0.34 mM Na2HPO4, 1 mM MgCl2, 10 mM HEPES, pH 7.4). Platelets were stimulated by thrombin (Sigma) at 1 U/mL for 1 hour with shaking at 1000 rpm in the presence or absence of indicated Ab. After stimulation, the supernatant of the reaction was harvested for mature TGFβ1 quantification. Mature TGFβ1 quantification was determined according to the manufacturer's instruction without acidification by TGFβ1 Duoset® ELISA kit (R&D). GARP ref. Ab, an ABBV-151 analog, was used as a positive control.

Figure 2:
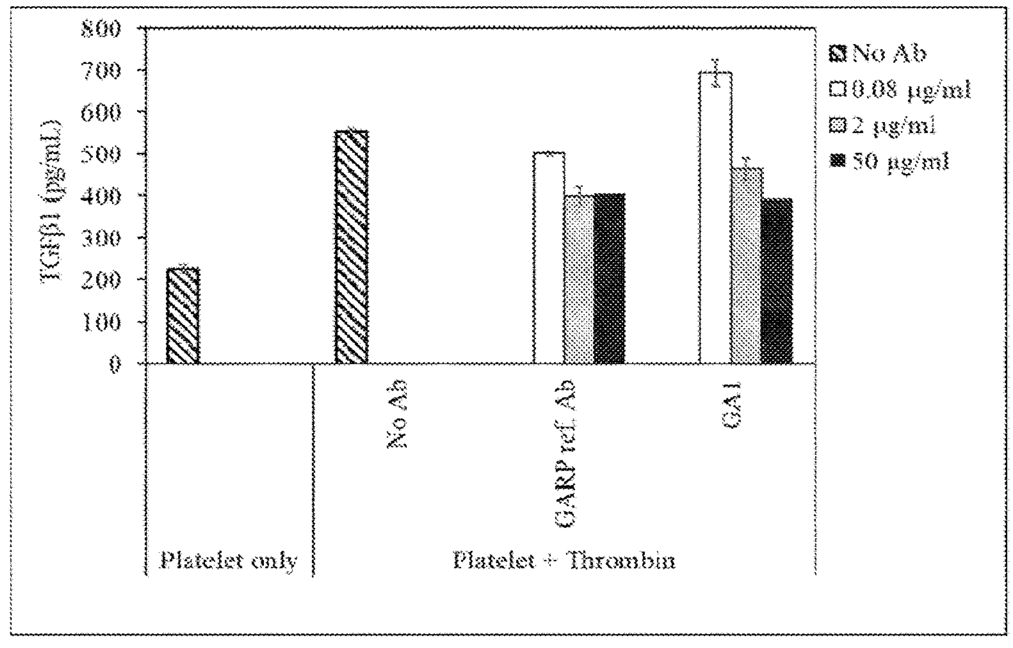
FIG. 2 depicts that GA1 inhibits the release of mature TGFβ1 from activated platelets. Platelets were stimulated by thrombin for 1 hour in the presence or absence of indicated antibodies. After stimulation, the supernatant of the reaction was harvested for mature TGFβ1 quantification. Mature TGFβ1 was detected using a TGFβ1 Duoset® ELISA kit (R&D). GARP ref. Ab, an ABBV-151 analog, was used as a positive control.

As shown in FIG. 2, thrombin stimulated mature TGFβ1 release from platelets compared to platelet only samples, and GA1 inhibited mature TGFβ1 release from thrombin-activated human platelets in a dose dependent manner.

Furthermore, GA1's ability to reduce platelet-mediated T cell suppression was tested. Human CD4+ T cells were isolated by MagniSort Human CD4 T cell Enrichment Kit (eBioscience). CD4+ T cells ($5\times10^{-4}$) were stimulated by anti-CD3/CD28 Dynabeads (Gibco) at a bead-to-cell ratio of 1:40 with or without platelets ($1\times10^{7}$) in the presence or absence of indicated antibodies for 4 days. After incubation, the culture supernatants were collected for IFNγ quantification. The amount of IFNγ were measured by Human IFNγ ELISA MAX Deluxe kit (Biolegend) according to the manufacturer's instruction. Isotype control (bevacizumab) was used as a negative control. GARP ref Ab, an ABBV-151 analog, was used as a positive control.

Figure 3:
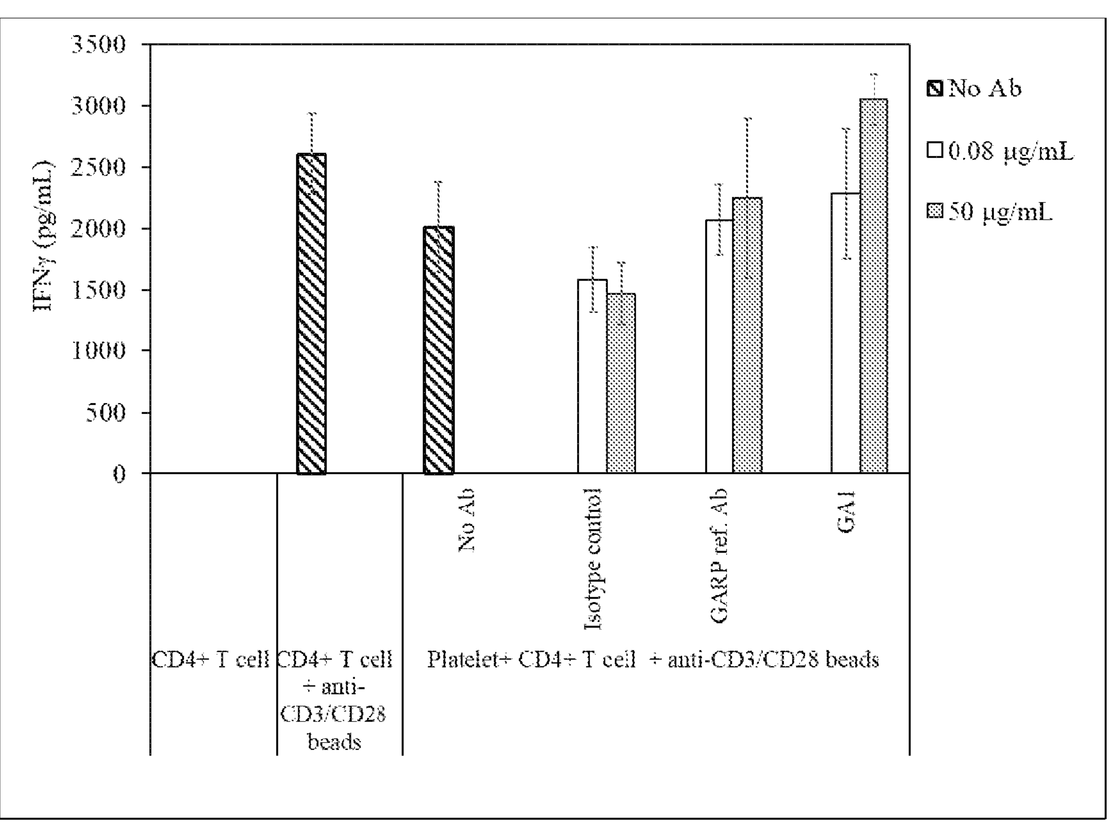
FIG. 3 depicts that GA1 reduces the platelet-mediated T cell suppression. CD4+ T cells were stimulated by anti-CD3/CD28 Dynabeads (Gibco) at a bead-to-cell ratio of 1:40 and incubated with the platelets and GA1 for 4 days. The harvested supernatants were subject to IFNγ quantification. GARP ref. Ab, an ABBV-151 analog, was used as a positive control. Isotype control (bevacizumab) was used as a negative control.

As shown in FIG. 3, IFNγ secretion from CD4+ T cells was stimulated by anti-CD3/CD28 beads compared to T cells only, whereas the addition of platelet suppressed the IFNγ secretion. Both GA1 and the ABBV-151 analog reduced the platelet suppression of the IFNγ secretion, whereas the isotype control antibody did not reduce the platelet suppression. Compared to the ABBV-151 analog, GA1 exhibited higher reduction of the platelet suppression, resulting in higher IFNγ secretion from CD4+ T cells, especially at the higher dosage level. As IFNγ is an important antitumor cytokine, the results indicated that GA1 has improved anti-tumor efficacy.

GA1's ability to reduce Treg-mediated T cell suppression was also tested in the mixed leukocyte reaction assays. Human T cells were isolated by MagniSort Human T cell Enrichment Kit (eBioscience). Human CD4+CD25+ $CD127^{low}$ Treg was isolated by EasySep human CD4+ $CD127^{low}$ CD25+ regulatory T cell isolation kit (Stemcell) according to the instructions provided by the manufacturer, and expanded in the X-VIVO 15 medium (LONZA) containing IL-2 (300 U/ml, eBioscience), rapamycin (1 nM, Selleckchem), and 5% human serum (Sigma) in the presence of anti-CD3/CD28 Dynabeads for 13-15 days. Treg cells ($2.5\times10^3$) were added into the mixture of T cells ($1\times10^5$) and allogeneic dendritic cells (DCs) ($1\times10^4$) with or without dose titrations of antibodies in RPMI-1640 complete medium at 37 C° with an atmosphere of 5% $CO_2$. After 5 days incubation, IFNγ and IL-2 secretion in culture supernatants were quantified by Human IFNγ ELISA MAX Deluxe kit and Human IL-2 ELISA MAX Deluxe kit, respectively (Biolegend). Isotype control (bevacizumab) was used as a negative control. GARP ref. Ab, an ABBV-151 analog, was used as a positive control.

Figure 4A:
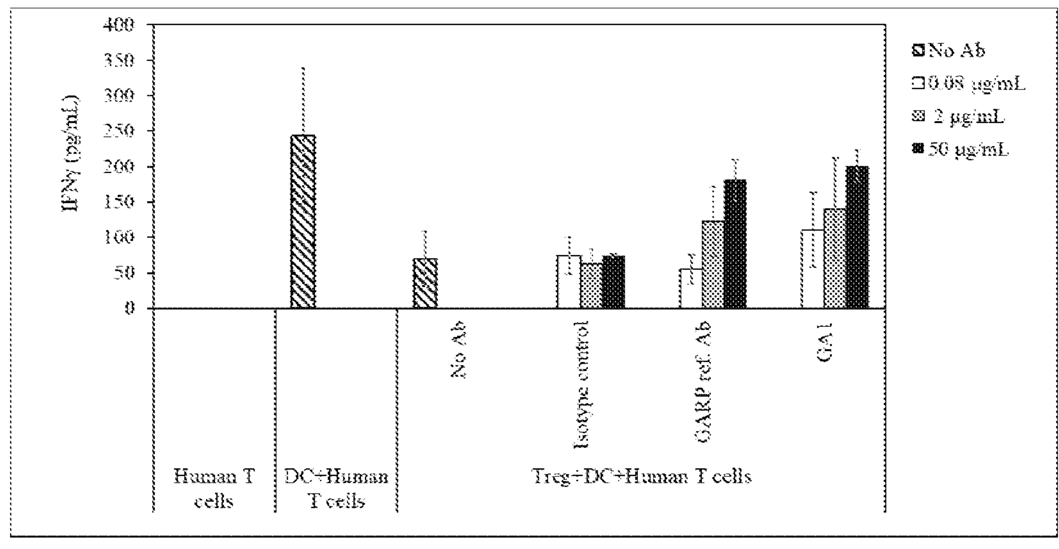
FIGS. 4A and 4B depict that GA1 can reverse the Treg-mediated T cell suppression. In a mixed leukocyte reaction assay, isolated Treg cells ($2.5\times10^3$) were added into a mixture of T cells ($1\times10^5$) and allogeneic dendritic cells (DCs) ($1\times10^4$) with or without antibodies. After 5 days incubation, IFNγ (4A) and IL-2 (4B) secretion in culture supernatants were quantified. GARP ref. Ab, an ABBV-151 analog, was used as a positive control. Isotype control (bevacizumab) was used as a negative control.
Figure 4B:
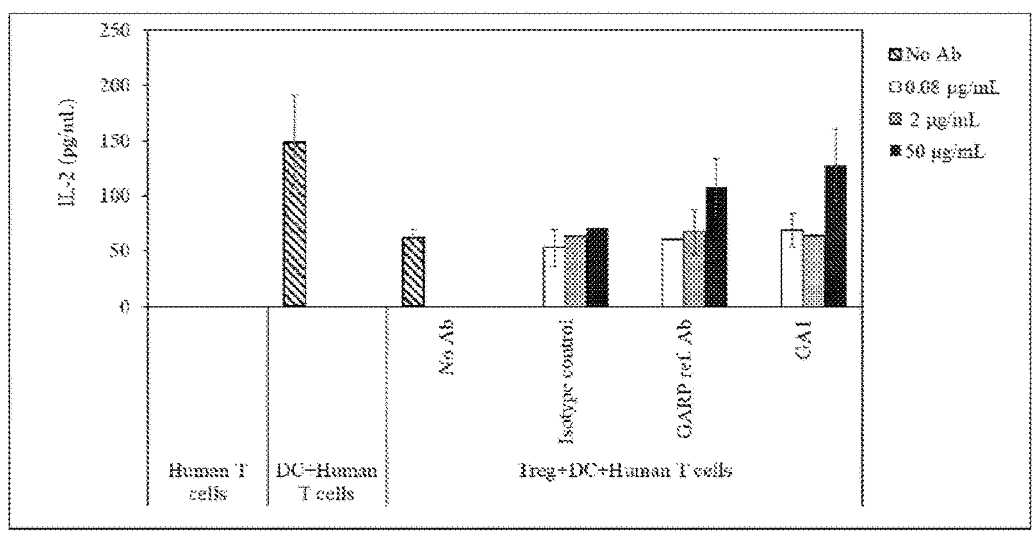

As shown in FIGS. 4A and 4B, IFNγ and TL-2 secretion from human T cells was stimulated by the dendritic cells (DC), whereas the addition of Treg cells suppressed the IFNγ and IL-2 secretion. Both GA1 and the ABBV-151 analog reduced the Treg suppression and elevated the IFNγ and IL-2 secretion levels, compared to the isotype control antibody and the no antibody group. Compared to the ABBV-151 analog, GA1 resulted in higher IFNγ secretion from T cells.

As IFNγ and IL-2 are important antitumor cytokines, the results indicated that GA1 has improved anti-tumor efficacy.

Moreover, the in vivo antitumor efficacy of GA1 was tested alone and in combination with an anti-PD1 antibody in a syngeneic MC38 mouse model (colon cancer). A total of $3\times10^{-5}$ MC38 cells (mouse colon cancer cells) in 100 μL of PBS were mixed with 100 μL of Matrigel (Corning, CA, USA) (in a 1:1 ratio) and subcutaneously implanted into both side flanks of male C57BL/6 mice (Biolasco, Taipei, Taiwan). When tumor size reached 100-150 $mm^3$, indicated antibodies in each group or control reagent were administered intraperitoneally twice per week for 3 weeks. Tumors were observed and measured twice a week. Tumor volume was defined as TV (tumor volume)=(length×width$^2$)/2. All data points represent means±SEM. Tumor growth inhibition (TGI) was calculated by comparing the tumor volume of each treatment group with the vehicle control group.

Figure 5:
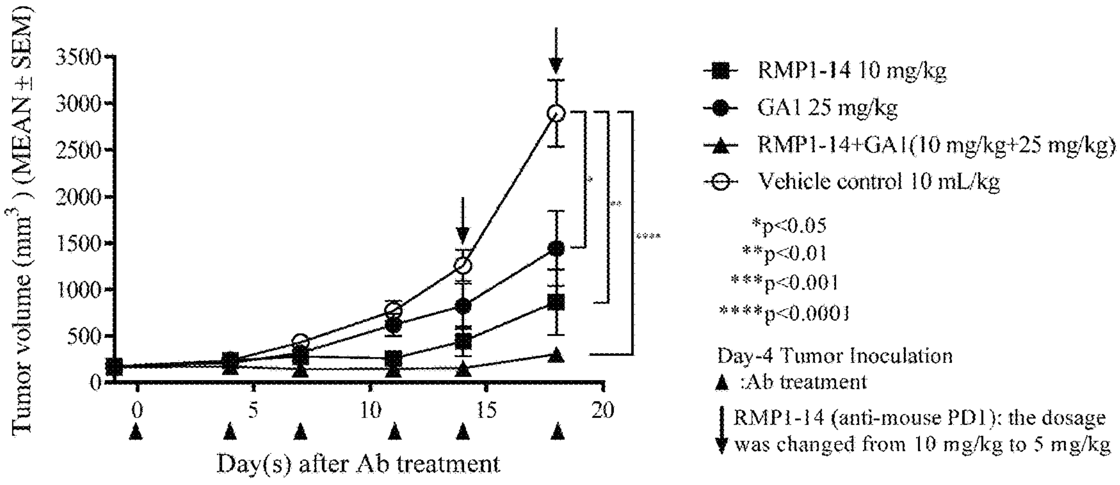
FIG. 5 depicts that GA1 can inhibit tumor growth alone and in combination with an anti-PD1 antibody. In a MC38 (mouse colon cancer) syngeneic mouse model, C57BL/6 mice (n=6 mice/group) were subcutaneously engrafted with MC38 cells. The first dose of each test agent was administered 4 days after tumor inoculation. Mice were intraperitoneally treated with indicated antibodies twice per week for 3 weeks. RMP1-14 was a commercially available anti-mouse PD1 antibody. All data points represent means±SEM.
Figure 6A:
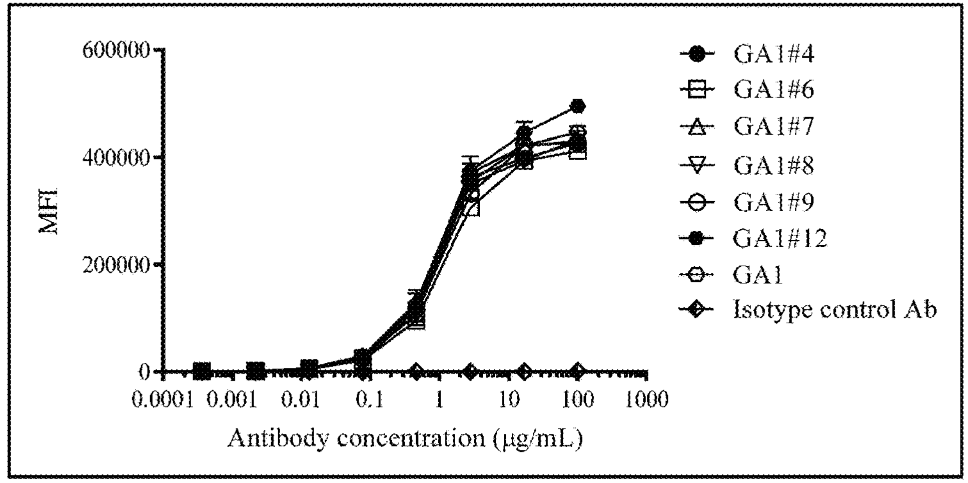
FIGS. 6A-6E depict GARP/latent TGFβ1 binding ability of GA1 top variants. GA1 top variants selected from affinity maturation were tested for their binding ability to human GARP/latent TGFβ1 transfected CHO-S cells (6A), cynomolgus GARP/latent TGFβ1 transfected CHO-S cells (6B), mouse GARP/latent TGFβ1 transfected CHO-S cells (6C), thrombin-activated human platelets (6D), and anti-CD3/CD28 beads-activated human Treg cells (6E) by flow cytometry. Isotype control (bevacizumab) was used as a negative control.
Figure 6B:
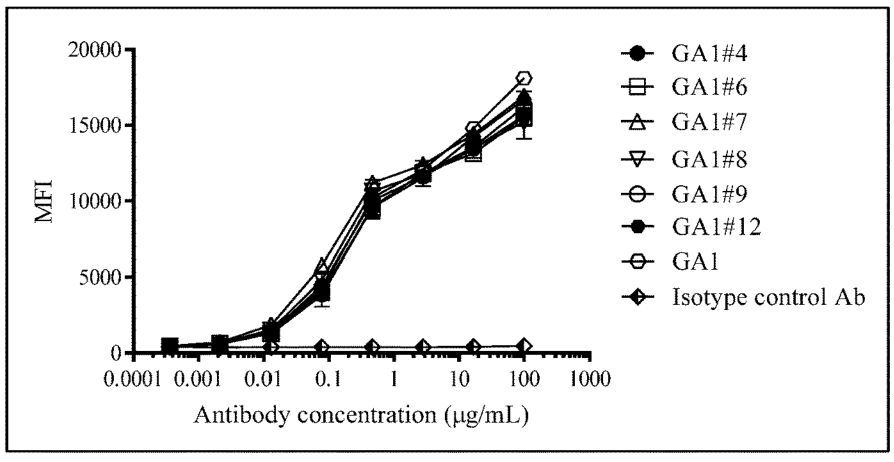
Figure 6C:
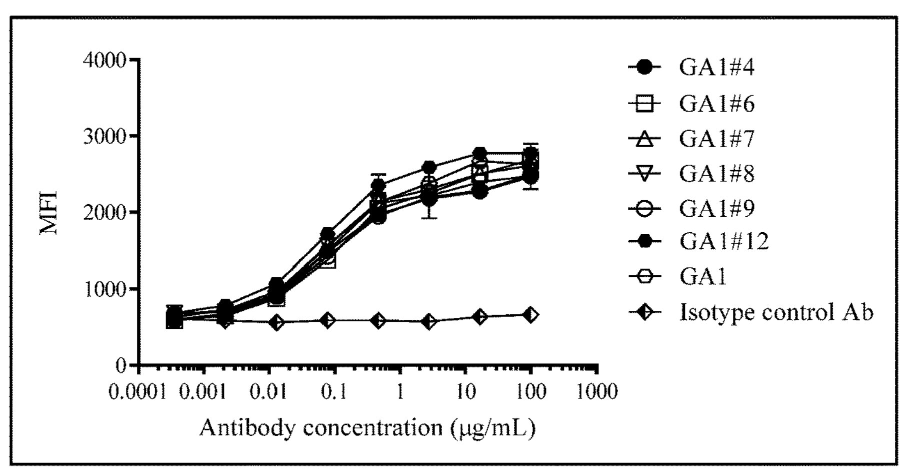
Figure 6D:
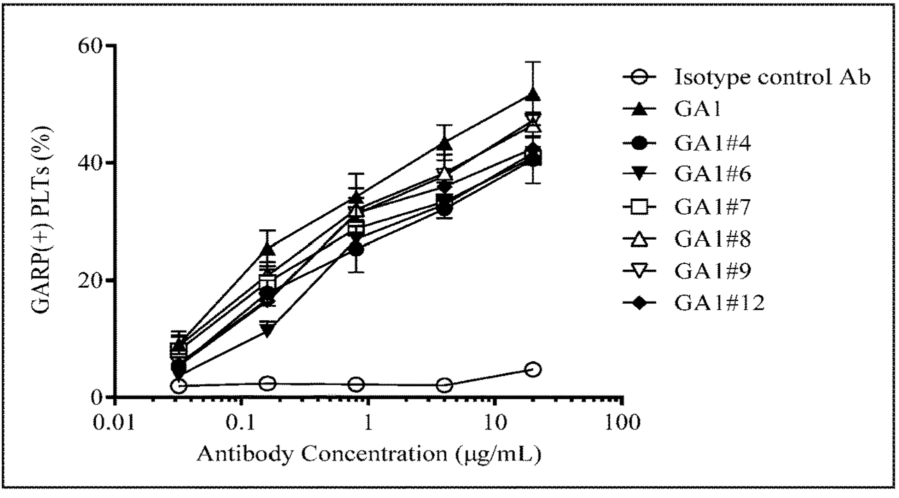
Figure 6E:
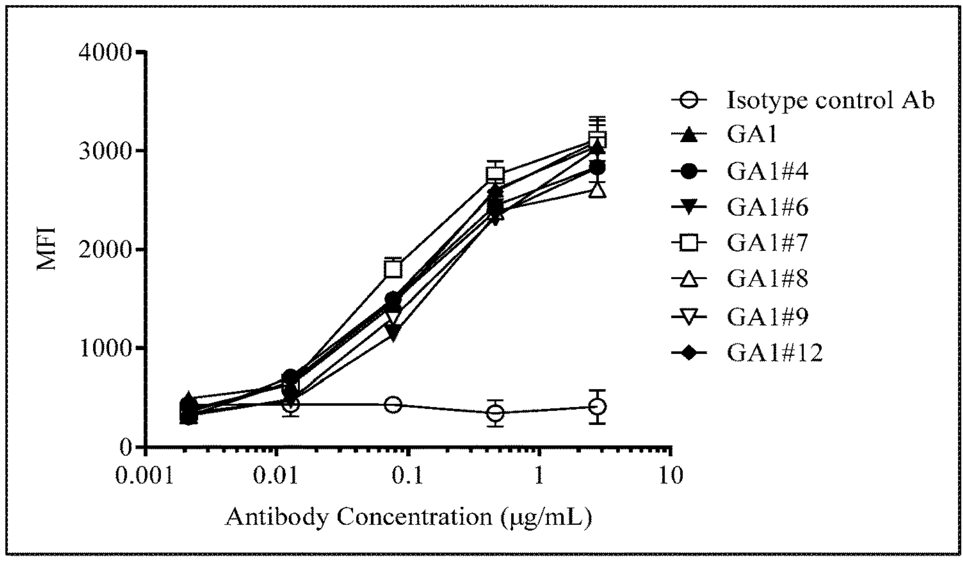

As shown in FIG. 5, GA1 alone significantly reduced tumor growth (TGI=53%) compared to the control group. The anti-PD1 antibody (RMP1-14) alone also significantly reduced tumor growth as expected (TGI=75%). Moreover, the combination of GA1 and the anti-PD1 antibody resulted in further tumor growth inhibition (TGI=95.0%). The results demonstrate that GA1 has antitumor efficacy in vivo on its own, and the combination of GA1 and an anti-PD1 antibody can provide significantly enhanced antitumor efficacy compared toa mono-treatment using either antibody. As anti-PD1 antibodies such as pembrolizumab and nivolumab have been used extensively in treating various types of cancers, the results indicate that GA1 can further improve the therapeutic efficacy of anti-PD1 antibodies when used in combination.

Example 2. Screening and Testing of GA1 Variants

To further improve the therapeutic efficacy of antibody clone GA1, it was subject to in vitro phage display-based affinity maturation to enhance the affinity to the GARP/TGFβ antigen according to standard protocol. Briefly, one or more CDR residues are mutated and the variant antibodies displayed on phage and screened for better binding ability for GARP/TGFβ1 complex by enzyme linked immunosorbent assay (ELISA) and fluorescent activated cell sorting (FACS).

Whole cell binding ability of GA1 variants was tested using transfected CHO-S cells expressing human, cynomolgus and mouse human GARP/TGFβ1 complex as well as activated platelets and Treg cells, which expresses human GARP/TGFβ1 complex on the cell surface. The activation of Treg cells was performed by incubation with anti-CD3/CD28 Dynabead (Gibco) at a cell-to-bead ratio of 1:1 for 24 hrs. The activation of platelets was performed by incubation with thrombin (Sigma) at 1 U/mL for 1 hour. Whole cell binding ability of various antibodies was then tested by incubating the cells with the serially diluted anti-GARP/TGFβ monoclonal antibodies in FACS buffer (lx PBS containing 2% FBS) at 4° C. for a half hour. The cells were washed with FACS buffer, and the binding was detected with goat anti-human IgG(H+L) FITC Ab at 4° C. for another half hour. Flow cytometric analyses were performed using the CytoFLEX platform (Beckman Coulter). Isotype control (bevacizumab) was used as a negative control. GARP ref Ab, an ABBV-151 analog synthesized in-house based on the sequence information disclosed in US 2016/0251438, was used as a positive control.

As shown in FIGS. 6A-6E, GA1 and its variants (GA1 #4, GA1 #6, GA1 #7, GA1 #8, GA1 #9 and GA1 #12) bound to human GARP/TGFβ1 complex, cynomolgus GARP/TGFβ1 complex and mouse GARP/TGFβ1 complex expressed on CHO-S cells as well as the human GARP/TGFβ1 complex on thrombin-activated human platelets and activated human Treg cells.

Figure 7:
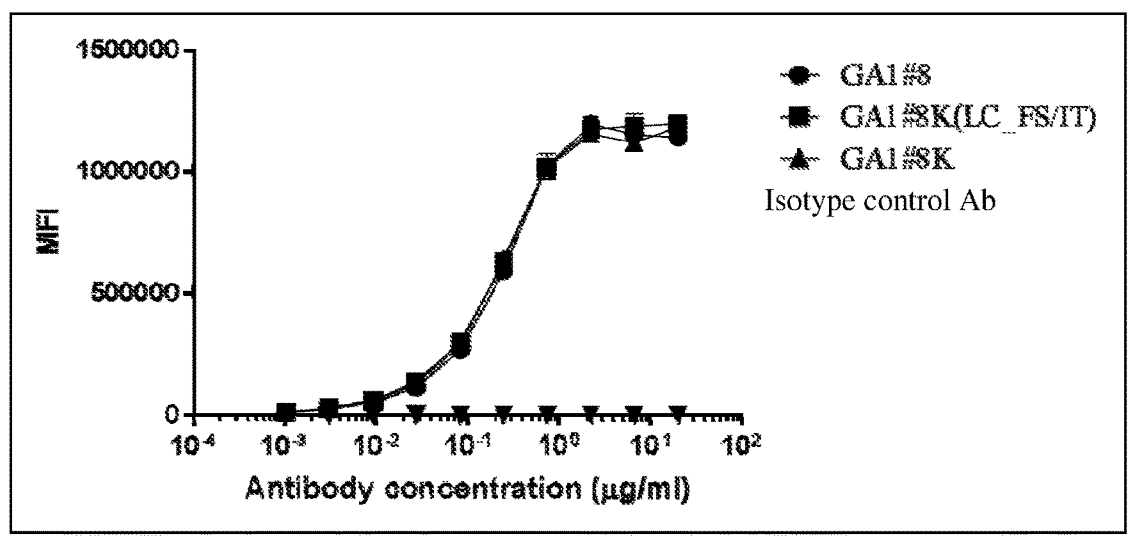
FIG. 7 depicts whole cell binding ability of GA1 framework/constant region variants to human GARP/latent TGFβ1 transfected CHO-S cells. Isotype control (bevacizumab) was used as a negative control.

Additionally, GA1 variants with modifications in the framework/constant regions were also tested. For example, GA1 #8K contains an addition of a heavy chain C-terminal lysine compared to GA1 #8, and GA1 #8K(LC_FS/IT) contains two amino acid substitutions in the light chain framework region (FR1 and FR3) of GA1 #8K. Whole cell binding ability of these constant region variants was tested against human GARP/latent TGFβ1 transfected CHO-S cells using the method describe above. Isotype control (bevacizumab) was used as a negative control. As shown in FIG. 7, the framework/constant region variants (GA1 #8K and GA1 #8K(LC_FS/IT)) were able to bind to human GARP/latent TGFβ1 transfected CHO-S cells in the same manner with GA1 #8. These results demonstrated that modifications in the framework/constant regions do not alter the GA1 variants' ability to bind to the antigen.

Next, GA1 variants' ability to inhibit the release of mature TGFβ1 from activated platelets was tested. Platelets were prepared as described as the following. Blood was drawn to a BD vacutainer glass blood collection tubes with acid citrate dextrose (ACD)(BD) and centrifuged for 20 min at 200×g, and the upper layer of platelet-rich plasma was collected. The collected platelet-rich plasma was gently mixed with iso-volume of HEP buffer (140 mM NaCl, 2.7 mM KCl, 3.8 mM HEPES, 5 mM EGTA, pH 7.4) containing 1 μM prostaglandin E1(sigma) and centrifuged for 20 min at 100×g to remove RBC and white blood cells. The supernatant was then transferred to a new tube and the platelets were pelleted down by centrifugation at 800×g for 20 min. The pellet was further rinsed with wash buffer (10 mM sodium citrate, 150 mM NaCl, 1 mM EDTA, 1% (w/v) dextrose, pH 7.4), and resuspended the platelet pellet in Tyrode's buffer (134 mM NaCl, 12 mM $NaHCO_3$, 2.9 mM KCl, 0.34 mM Na2HPO4, 1 mM MgCl2, 10 mM HEPES, pH 7.4). Platelets were stimulated by thrombin (Sigma) at 1 U/mL for 1 hour with shaking at 1000 rpm in the presence or absence of indicated Ab. After stimulation, the supernatant of the reaction was harvested for mature TGFβ1 quantification. Mature TGFβ1 quantification was determined according to the manufacturer's instruction without acidification by TGFβ1 Duoset® ELISA kit (R&D). Isotype control (bevacizumab) was used as a negative control. GARP ref. Ab, an ABBV-151 analog, was used as a positive control.

Figure 8:
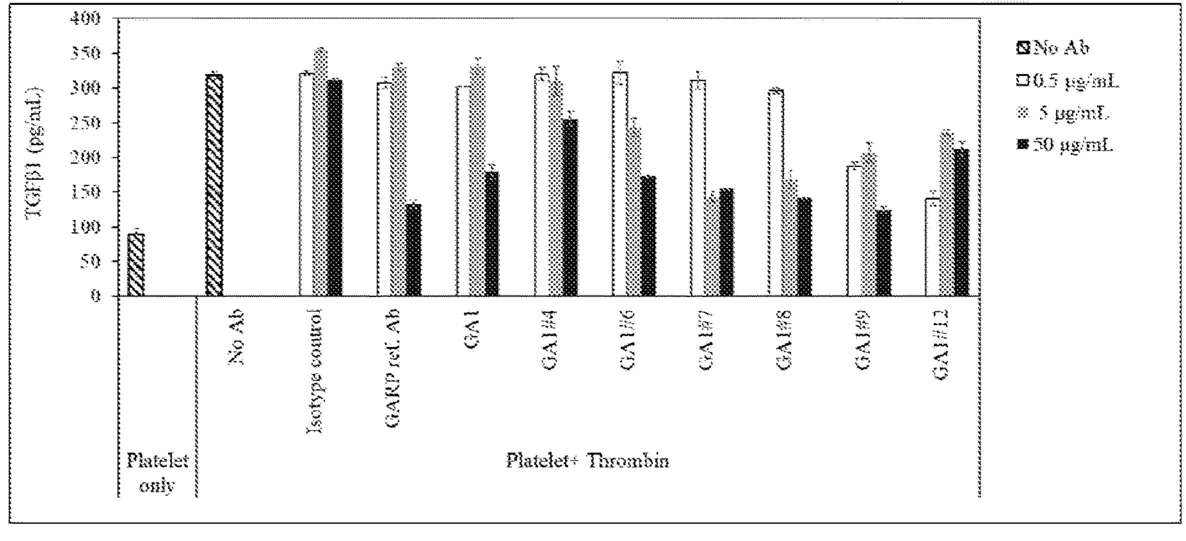
FIG. 8 depicts that GA1 variants inhibit the release of mature TGFβ1 from activated platelets. Platelets were stimulated by thrombin for 1 hour in the presence or absence of indicated antibodies. After stimulation, the supernatants of the reaction were harvested for mature TGFβ1 quantification. Mature TGFβ1 was detected using a TGFβ1 Duoset® ELISA kit (R&D). GARP ref. Ab, an ABBV-151 analog, was used as a positive control. Isotype control (bevacizumab) was used as a negative control.

As shown in FIG. 8, thrombin stimulated mature TGFβ1 release from platelets compared to platelet only samples, and GA1 variants inhibited mature TGFβ1 release from thrombin-activated human platelets in a dose dependent manner.

Furthermore, GA1 variants' ability to reduce platelet-mediated T cell suppression was tested. Human CD4+ T cells were isolated by MagniSort Human CD4 T cell Enrichment Kit (eBioscience). CD4+ T cells ($5\times10^4$) were stimulated by anti-CD3/CD28 Dynabeads (Gibco) at a bead-to-cell ratio of 1:40 with or without platelets ($1\times10^{-7}$) in the presence or absence of indicated antibodies for 4 days. After incubation, the culture supernatants were collected for IFNγ quantification. The amount of IFNγ were measured by Human IFNγ ELISA MAX Deluxe kit (Biolegend) according to the manufacturer's instruction. Isotype control (bevacizumab) was used as a negative control. GARP ref. Ab, an ABBV-151 analog, was used as a positive control.

Figure 9:
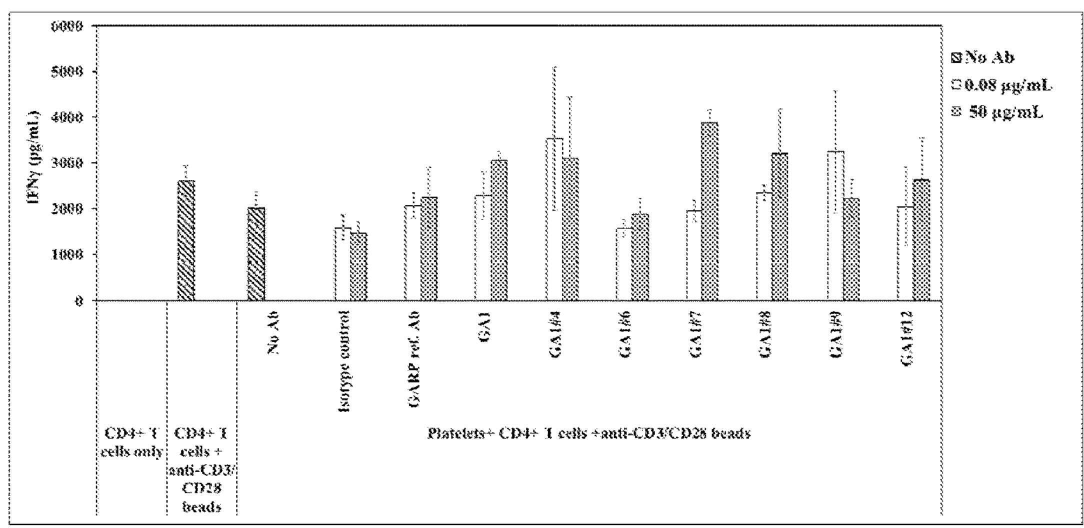
FIG. 9 depicts that GA1 selected variants reduce the platelet-mediated T cell suppression. CD4+ T cells were stimulated by anti-CD3/CD28 Dynabeads (Gibco) at a bead-to-cell ratio of 1:40 with or without platelets in the presence or absence of indicated antibodies for 4 days. The harvested supernatants from the reactions were subject to IFNγ quantification. GARP ref. Ab, an ABBV-151 analog, was used as a positive control. Isotype control (bevacizumab) was used as a negative control.

As shown in FIG. 9, IFNγ secretion from CD4+ T cells was stimulated by anti-CD3/CD28 beads compared to T cells only, whereas the addition of platelet suppressed the IFNγ secretion. Both GA1 variants and the ABBV-151 analog reduced the platelet suppression of the IFNγ secretion, whereas the isotype control antibody did not reduce the platelet suppression of the IFNγ secretion. Compared to the ABBV-151 analog, GA1 variants exhibited higher reduction of the platelet suppression, resulting in higher IFNγ secretion from CD4+ T cells. As IFNγ is an important antitumor cytokine, the results indicated that GA1 variants have improved anti-tumor efficacy.

GA1 variants' ability to reduce Treg-mediated T cell suppression was also tested in the mixed leukocyte reaction assays. Human T cells were isolated by MagniSort Human T cell Enrichment Kit (eBioscience). Human CD4+CD25+ $CD127^{low}$ Treg was isolated by EasySep human CD4+ $CD127^{low}$ CD25+ regulatory T cell isolation kit (Stemcell) according to the instructions provided by the manufacturer, and expanded in the X-VIVO 15 medium (LONZA) containing IL-2 (300 U/ml, eBioscience), rapamycin (1 nM, Selleckchem), and 5% human serum (Sigma) in the presence of anti-CD3/CD28 Dynabeads for 13-15 days. Treg cells ($2.5\times10^3$) were added into the mixture of T cells ($1\times10^5$) and allogeneic dendritic cells (DCs) ($1\times10^4$) with or without dose titrations of antibodies in RPMI-1640 complete medium at 37 C° with an atmosphere of 5% $CO_2$. After 5 days incubation, IFNγ and IL-2 secretion in culture supernatants were quantified by Human IFNγ ELISA MAX Deluxe kit and Human IL-2 ELISA MAX Deluxe kit, respectively (Biolegend). Isotype control (bevacizumab) was used as a negative control. GARP ref. Ab, an ABBV-151 analog, was used as a positive control.

Figure 10A:
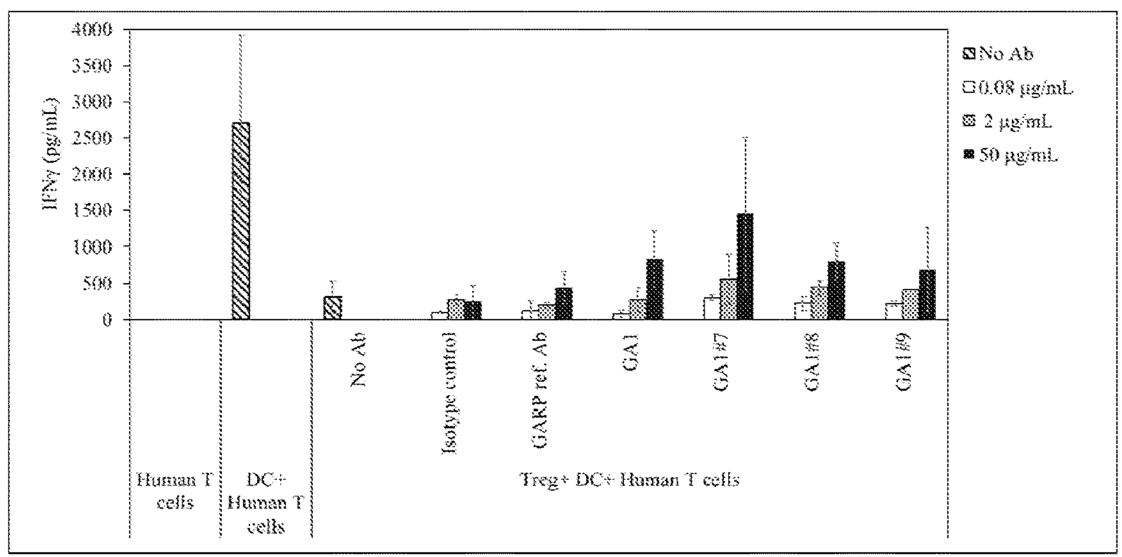
FIGS. 10A and 10B depict that GA1 variants can reverse the Treg-mediated T cell suppression. In a mixed leukocyte reaction assay isolated Treg cells ($2.5\times10^3$) were added into a mixture of T cells ($1\times10^5$) and allogeneic dendritic cells (DCs) ($1\times10^4$) with or without GA1 variants. After 5 days incubation, IFNγ (10A) and IL-2 (10B) secretion in culture supernatants were quantified. GARP ref Ab, an ABBV-151 analog, was used as a positive control. Isotype control (bevacizumab) was used as a negative control.
Figure 10B:
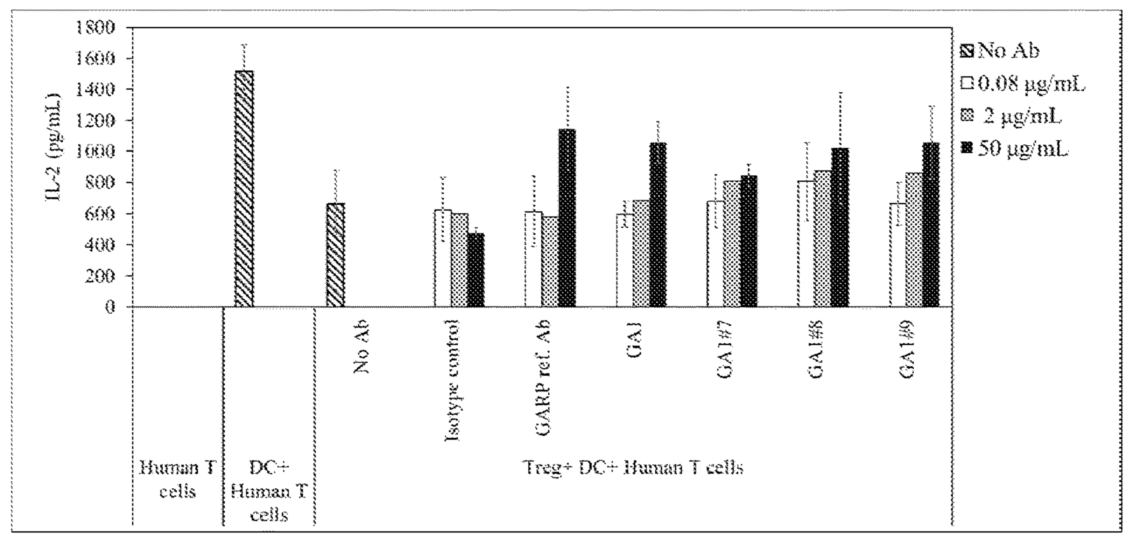

As shown in FIGS. 10A and 10B, IFNγ and TL-2 secretion from human T cells was stimulated by the dendritic cells (DC), whereas the addition of Treg cells suppressed the IFNγ and IL-2 secretion. Both GA1 variants and the ABBV-151 analog reduced the Treg suppression and elevated the IFNγ and IL-2 secretion levels, compared to the isotype control antibody and the no antibody group. Compared to the ABBV-151 analog, GA1 variants resulted in higher IFNγ secretion from T cells. As IFNγ and IL-2 are important antitumor cytokine, the results indicated that GA1 variants has improved anti-tumor efficacy.

GA1 variants' ability to inhibit TGFβ-mediated Smad2 phosphorylation was tested in activated human Treg cells. Human CD4+CD25+$CD127^{low}$ Treg was isolated by EasySep human CD4+$CD127^{low}$ CD25+ regulatory T cell isolation kit (Stemcell) according to the instructions provided by the manufacturer, and expanded in X-VIVO™ 15 medium (LONZA) containing IL-2 (300 U/ml, eBioscience), rapamycin (1 nM, Selleckchem), and 5% human serum (Sigma) in the presence of anti-CD3/CD28 Dynabeads (Thermo) for 13-15 days. Expended Tregs ($1\times10^{-6}$ cells/ml) were stimulated in serum-free X-VIVO 15 medium with anti-CD3/CD28 Dynabeads in the presence or absence of antibodies for 24 hrs. Recombinant human TGFβ1 (20 ng/mL, PeproTech) stimulation was performed by incubation with cells for 30 mins. After stimulation, cells were lysed and submitted to SDS-polyacrylamide gel electrophoresis under reducing conditions. Gels were blotted on nitrocellulose membranes with the Wet/Tank Blotting system (Bio-Rad). After blocking, membranes were incubated with primary antibodies directed against P-Smad2 (Cell Signaling Technology) or GAPDH (Cell Signaling Technology), then with secondary HRP-coupled antibodies, and revealed with an ECL substrate (Thermo). The presence of P-Smad2 indicates the production of active TGFβ1 by the stimulated Tregs. Isotype control (bevacizumab) was used as a negative control. Recombinant human TGFβ (rhTGFβ) and GARP ref Ab, an ABBV-151 analog, were used as positive controls. Anti-TGFβ, a commercially available anti-TGFβ antibody (1D111) from Bio X Cell, was also used as a positive control.

Figure 11:
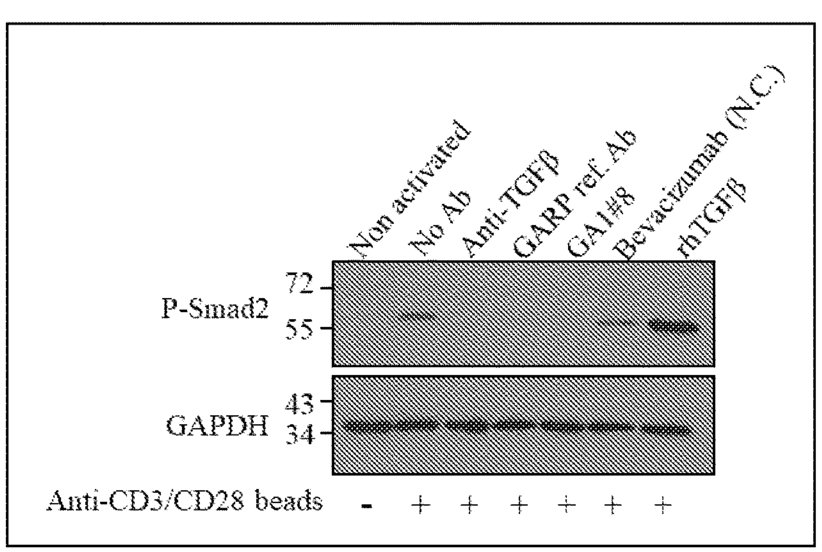
FIG. 11 depicts that GA1 #8 inhibits TGFβ-mediated Smad2 phosphorylation in the activated human Treg cells. Isolated Treg was stimulated with anti-CD3/CD28 Dynabeads (Gibco) at a bead-to-cell ratio of 1:1 in the presence or absence of the indicated antibodies for 24 hrs. Cell lysates were analyzed by Western Blot with antibodies against P-Smad2 (as a readout for active TGFβ1 production) and GAPDH (as the loading control). Anti-TGFβ was a commercially available anti-TGFβ antibody (1D11) from Bio X Cell. Isotype control (bevacizumab) was used as a negative control. GARP ref. Ab, an ABBV-151 analog, was used as a positive control.

As shown in FIG. 11, no antibody sample and the negative control sample showed a similar baseline P-Smad2 level; treatment of recombinant human TGFβ (rhTGFβ) increased the P-Smad2 level as expected; and a representative GA1 variant (GA1 #8), the ABBV-151 analog and anti-TGFβ were able to suppress Smad2 phosphorylation in Treg cells. As TGFβ-mediated Smad2 signaling is important for Treg cell activation, the result indicate that GA1 variant can suppress Treg cell activation, which in turn can enhance effector T cell functions and improve an immune response in a subject against diseases and tumors.

Moreover, the in vivo antitumor efficacy of GA1 variants was tested in a syngeneic MC38 mouse model (colon cancer). A total of $3\times10^{-5}$ MC38 cells (mouse colon cancer cells) in 100 μL of PBS were mixed with 100 μL of Matrigel (Corning, CA, USA) (in a 1:1 ratio) and subcutaneously implanted into both side flanks of male C57BL/6 mice (Biolasco, Taipei, Taiwan). When tumor size reached 100-150 $mm^3$, indicated antibodies in each group or control reagent were administered intraperitoneally twice per week for 3 weeks. Tumors were observed and measured twice a week. Tumor volume was defined as TV (tumor volume)=(length x $width^2$)/2. All data points represent means±SEM.

Tumor growth inhibition (TGI) was calculated by comparing the tumor volume of each treatment group with the vehicle control group.

Figure 12:
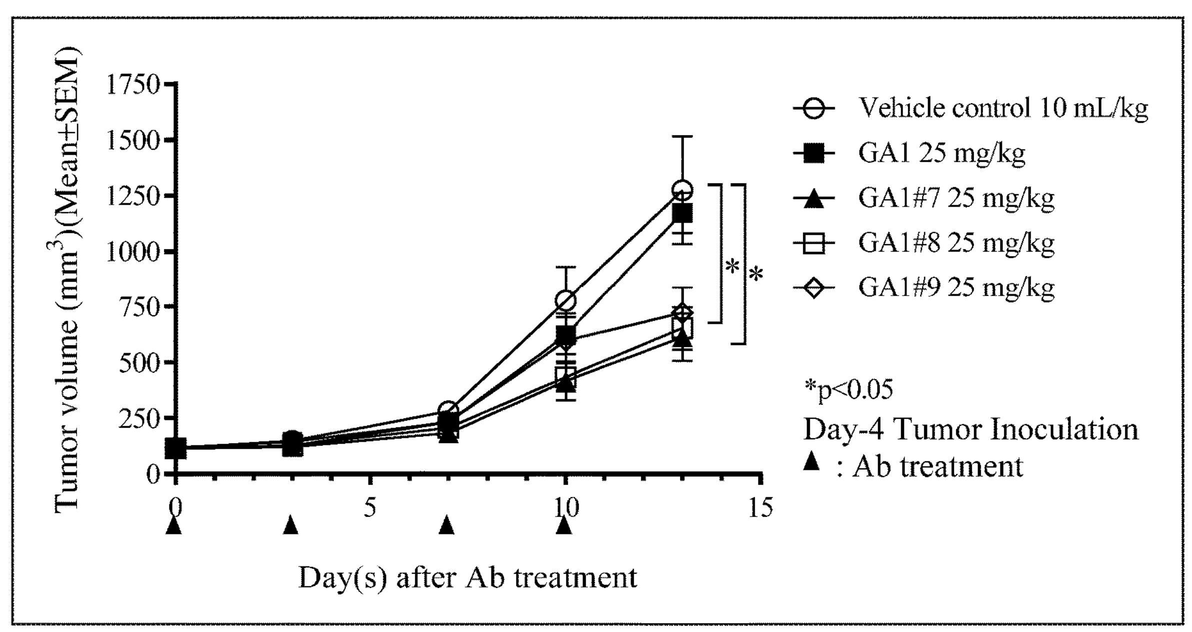
FIG. 12 depicts that GA1 variants can inhibit tumor growth in MC38 (mouse colon cancer) syngeneic mouse model. C57BL/6 mice (n=6 mice/group) were subcutaneously engrafted with MC38 cells. The first dose of each test agent was administered 4 days after tumor inoculation. Mice were intraperitoneally treated with indicated antibodies twice per week for 3 weeks. All data points are the means±SEM.

Although the previous study of GA1 in the MC38 mouse model demonstrated the antitumor efficacy of GA1, GA1 treatment did not show tumor inhibition before day 12 after treatment compared to the control group as shown in FIG. 5. Similarly, in this study, the tumor inhibition from GA1 treatment was minimal on day 13 after treatment (TGI=9%), as shown in FIG. 12. However, greater tumor inhibition was observed from the treatment of GA1 variants GA1 #7 (TGI=57%), GA1 #8 (TGI=54%) and GA1 #9 (TGI=48%) on day 13 after treatment. The results indicated superior antitumor efficacy of GA1 variants GA1 #7, GA1 #8 and GA1 #9 compared to GA1.

Figure 13:
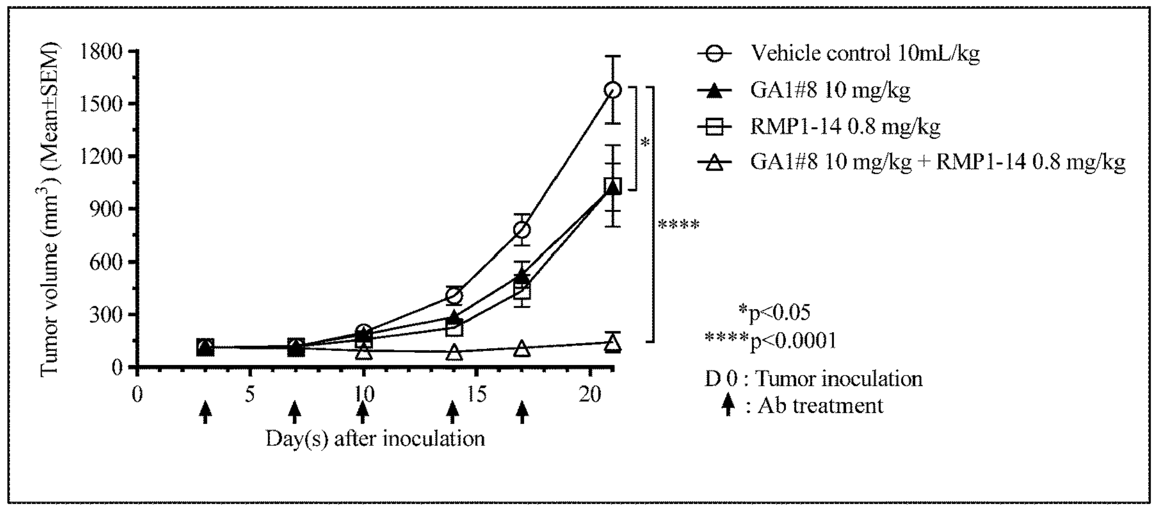
FIG. 13 depicts that GA1 #8 can inhibit tumor growth alone and in combination with an anti-PD1 antibody. In a MC38 (mouse colon cancer) syngeneic mouse model, C57BL/6 mice (n=10 mice/group) were subcutaneously engrafted with MC38 cells. The first dose of each test agent was administered 4 days after tumor inoculation. Mice were intraperitoneally treated with indicated antibodies twice per week for 3 weeks. RMP1-14 was a commercially available anti-mouse PD1 antibody. All data points represent means±SEM.

GA1 #8 was further tested in the MC38 mouse model at a lower dosage level (10 mg/kg) according to the same protocol described above. As show in FIG. 13, GA1 variant GA1 #8 alone significantly reduced tumor growth (TGI=37.8%) compared to the control group similar to the anti-PD1 antibody (RMP1-14; TGI=37.3%). Moreover, the combination of GA1 #8 and the anti-PD1 antibody resulted in further tumor growth inhibition (TGI=98.0%). The results demonstrate that GA1 #8 has antitumor efficacy in vivo at a lower dosage level, on its own and in combination with anti-PD1 antibody.

Furthermore, GA1 #8 was tested at a higher dosage (25 mg/kg) in a CT26 mouse model (mouse colon cancer) syngeneic mouse model. Compared to the MC38 model, the CT26 mouse model is reported as more resistant to PD1 inhibitor treatment and having a higher level of Treg cells in the tumor microenvironment compared to the MC38 model, which can impact the antitumor effect of anti-GARP/TGFβ antibody treatment. A total of $5\times10^{-5}$ CT26 cells (mouse colon cancer) in 100 μL of PBS were mixed with 100 μL of Matrigel (Corning, CA, USA) (in a 1:1 ratio) and subcutaneously implanted into both side flanks of BALB/c mice (Biolasco, Taipei, Taiwan). When tumor size reached 100-150 $mm^3$, indicated antibodies in each group or control were administered intraperitoneally twice per week for 3 weeks. Tumors were observed and measured twice a week. Tumor volume was defined as TV (tumor volume)=(length x $width^2$)/2. All data points represent means±SEM. Tumor growth inhibition (TGI) was calculated by comparing the tumor volume of each treatment group with the vehicle control group.

Figure 14:
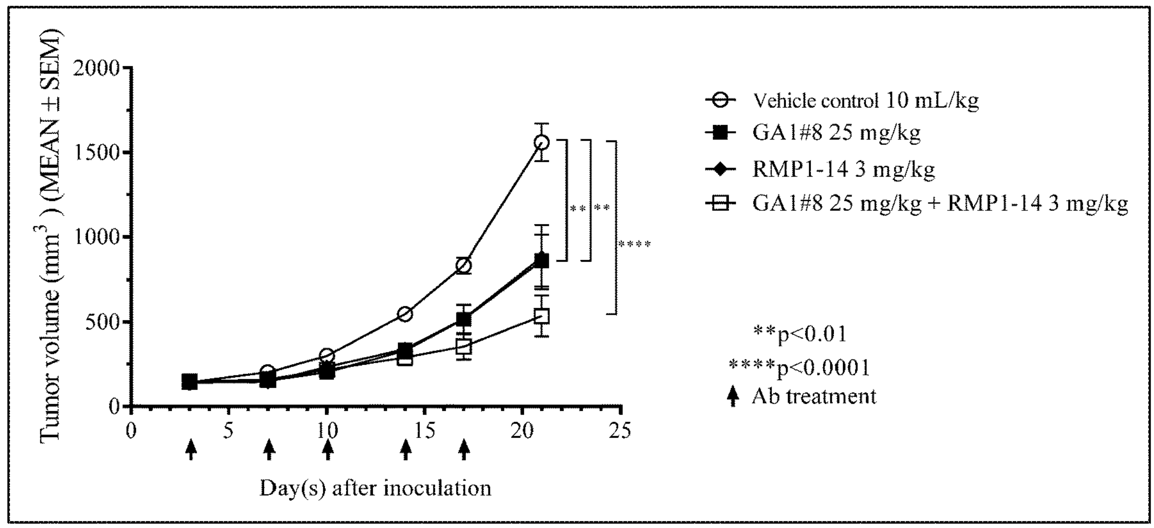
FIG. 14 depicts that GA1 #8 can inhibit tumor growth alone and in combination with an anti-PD1 antibody. In a CT26 (mouse colon cancer) syngeneic mouse model, C57BL/6 mice (n=10 mice/group) were subcutaneously engrafted with CT26 cells. The first dose of each test agent was administered 3 days after tumor inoculation. Mice were intraperitoneally treated with indicated antibodies twice per week for 3 weeks. RMP1-14 was a commercially available anti-mouse PD1 antibody. All data points represent means±SEM.

As shown in FIG. 14, GA1 variant GA1 #8 alone significantly reduced tumor growth (TGI=50%) compared to the control group similar to the anti-PD1 antibody (RMP1-14; TGI=48%). Moreover, the combination of GA1 #8 and the anti-PD1 antibody resulted in further tumor growth inhibition (TGI=73%). The results are consistent with the results from the MC38 model, and together they demonstrate that GA1 variant GA1 #8 has antitumor efficacy in vivo on its own, and the combination of GA1 #8 and an anti-PD1 antibody can provide significantly enhanced antitumor efficacy compared to a mono-treatment using either antibody. As anti-PD1 antibodies such as pembrolizumab and nivolumab have been used extensively in treating various types of cancers, the results indicate that GA1 variants such as GA1 #8 can further improve the therapeutic efficacy of anti-PD1 antibodies when used in combination.

Example 3. Screening and Testing of Anti-GARP/TGFβ Antibody hGA17

Additional anti-GARP/TGFβ antibody clones were identified by screening of a Fab phage library, which was generated from hybridomas constructed from mice immunized with either GARP/TGFβ1 complex or GARP ECD/TGFβ1 complex. One representative clone GA17 was selected for humanization of the framework. Briefly, Igblast was performed using the sequences of the clone to search database of human germline genes. Ideal germline sequences were selected, and mutations of framework sequences were made to change the framework sequences from mouse sequences to human sequences, resulting in a humanized clone hGA17.

ELISA binding of hGA17 was tested using human GARP/TGFβ1 complex and human GARP protein that are not in any GARP/TGFβ1 complex. Ninety-six well plates (Costar, 3690) were coated overnight at 4° C. with 30 μl/well of 4 μg/ml GARP/TGFβ1 complex or 2 μg/ml GARP protein in PBS buffer. Coated plates were washed with PBST buffer (PBS pH 7.4 with 0.05% Tween 20) for 5 times and blocked with SuperBlock™ buffer (Thermo, 37516). Duplicate titrations of hGA17, GA1 #8 and reference antibodies were generated (in the range of 1000 ng/ml to 0.32 ng/ml) and added to washed plates and incubated at room temperature for 2 hours. GARP ref Ab1, an ABBV-151 analog synthesized in-house based on the sequence information disclosed in US 2016/0251438, and GARP ref. Ab2, a DS-1005a analog synthesized in-house based on the sequence information disclosed in US 2018/0258184, were used as positive controls. ABBV-151, also known as LHG10.6, is an anti-GARP/TGFβ1 IgG4 antibody in clinical stage. DS-1005a also known as H151D-H1L1, is an anti-GARP/TGFβ IgG1 antibody in clinical stage. Plates were washed as above and 30 μl/well of a 1/8000 dilution of Goat Anti-Human IgG, Monkey ads-HRP (SouthernBiotech) was added and incubated for a further 1 hour at room temperature. After a further wash, bound antibody was detected with 30 μl/well TMB substrate (SurModics, TMBS-1000-01) and stopped with ELISA stop solution (Solarbio, C1058-100 ml). Absorbance was measured at 450 nm and the binding curves of the test antibodies were compared to the reference antibodies. Absorbance was plotted against sample concentration. The antibodies' binding ability to human GARP and human GARP/TGFβ1 complex was further tested by Octect.

Figure 15A:
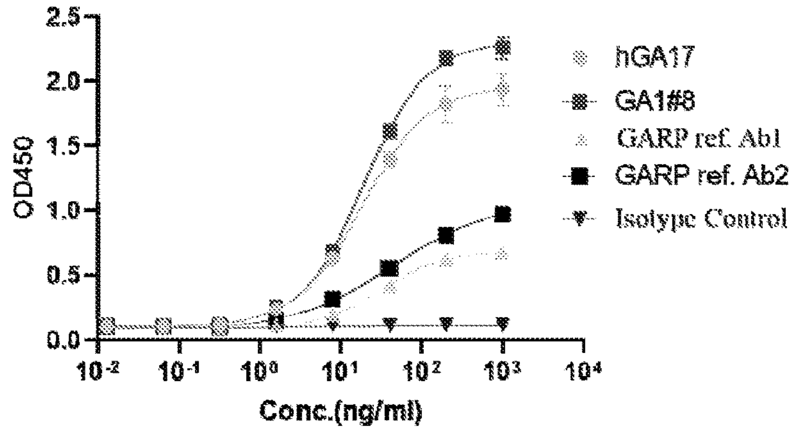
FIGS. 15A and 15B depict the binding of anti-GARP/TGFβ antibodies to human GARP/TGFβ complex (15A) and human GARP alone (15B) assessed by ELISA.
Figure 15B:
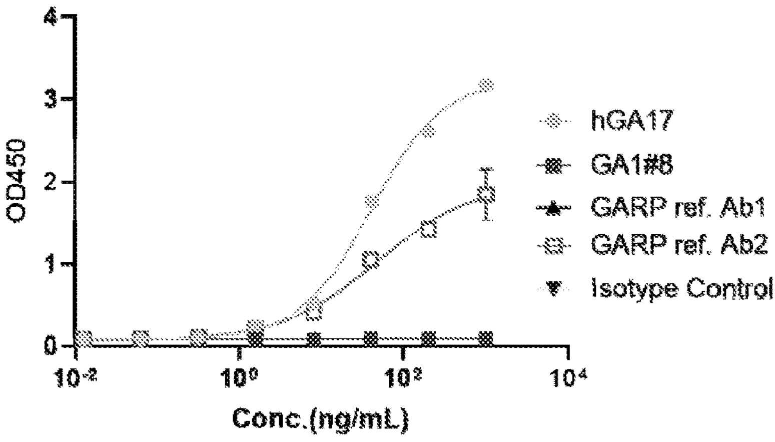

As shown in FIG. 15A, GA1 #8 and hGA17 both bound to human GARP/latent TGFβ1 complex and showed better binding compared to both reference antibodies. As shown in FIG. 15B, hGA17 and GARP Ref Ab2 both bound to human GARP alone, where hGA17 showed much stronger binding compared to GARP Ref. Ab2. In comparison, GARP Ref. Ab1 and GA1 #8 did not bind to human GARP outside of a GARP/TGFβ complex.

The antibodies' binding ability to human GARP and human GARP/TGFβ1 complex was further tested by Octect, and the results are shown in Table 3. Unlike GA1 #8 and ABBV-151, which only bound to GARP/TGFβ1 complex, hGA17 bound to both GARP/TGFβ1 complex and GARP with comparable affinity (Table 3). DS-1005a analog was capable of binding to GARP/TGFβ1 complex and GARP, but the binding was much weaker compared to hGA17.

TABLE 3

Binding affinity of anti-GARP/TGFβ antibodies by Octet

| Affinity (KD) | hGA17 | GA1#8 | GARP ref. Ab1 | GARP ref. Ab2 |
|---|---|---|---|---|
| hGARP | 4.292E−10 | N/A | N/A | 2.025E−09 |
| hGARP/1 TGFβ | 6.956E−10 | 2.813E-10 | 4.282E−10 | 4.120E−09 |

Whole cell binding ability of hGA17 and GA1 #8 was tested using GARP/TGFβ complex expressing tumor cells Hs 578T, GARP transfected CHO-S cells expressing human GARP proteins as well as human platelets and Treg cells, which express human GARP/latent TGFβ1 on the cell surface. Platelets were from Miao Tong Biological Science & Technology. Human CD4+CD25+CD127$^{low}$ Treg cells were isolated from human PBMC (Miao Tong Biological Science & Technology) by EasySep human CD4+CD127$^{low}$ CD25+ regulatory T cell isolation kit (Stemcell) according to the instructions provided by the manufacturer, and expanded in the X-VIVO 15 medium (LONZA) containing IL-2 (300 U/ml, eBioscience), rapamycin (1 nM, Selleckchem), and 5% human serum (Sigma) in the presence of anti-CD3/CD28 Dynabeads for 13-15 days. Activation of Treg cells was performed by incubation with anti-CD3/CD28 Dynabead (Gibco, 111.32D) at a cell-to-bead ratio of 1:1 for 24 hours. Whole cell binding ability of various antibodies was then tested by incubating the cells with the serially diluted anti-GARP/TGFβ monoclonal antibodies in FACS buffer (lx PBS containing 2% FBS) at 4° C. for one hour. Then, cells were washed with FACS buffer, and the binding was detected with goat anti-human IgG PE Ab (Biolegend) at 4° C. for another half hour. Flow cytometric analyses were performed using the CytoFLEX platform (Beckman Coulter). IgG isotype control (an anti-CLDN18.2 antibody) was used as a negative control. GARP ref Abl, the ABBV-151 analog and GARP ref. Ab2, the DS-1005a analog were used as positive controls.

Figure 16A:
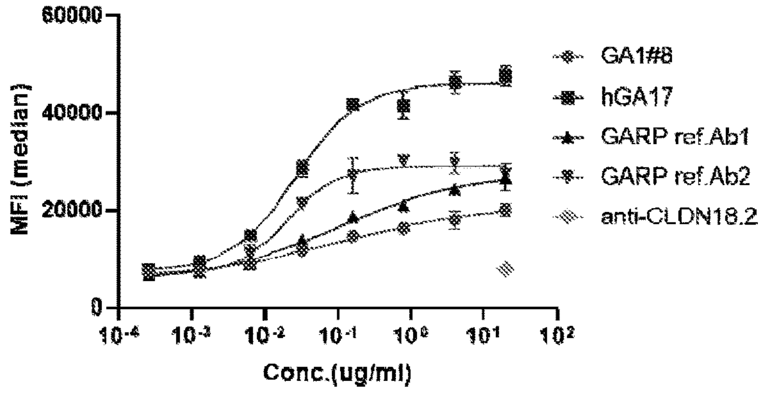
FIGS. 16A-16D depict whole cell binding of anti-GARP/TGFβ antibodies to Hs 578Tcells (16A), human GARP transfected CHO-S cells (16B), human platelets (16C) and human Treg cells (16D) assessed by flow cytometry.
Figure 16B:
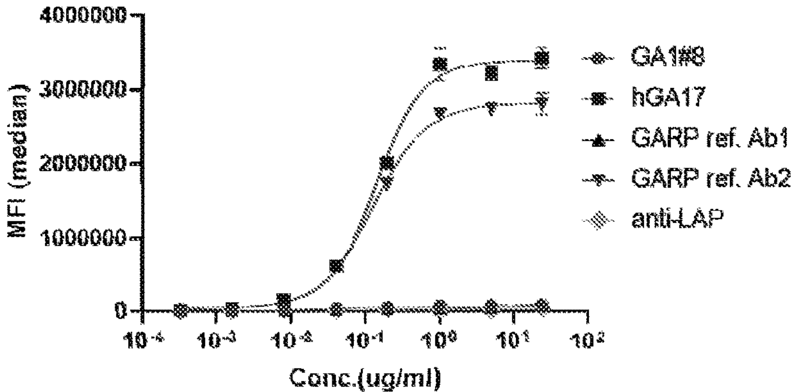
Figure 16C:
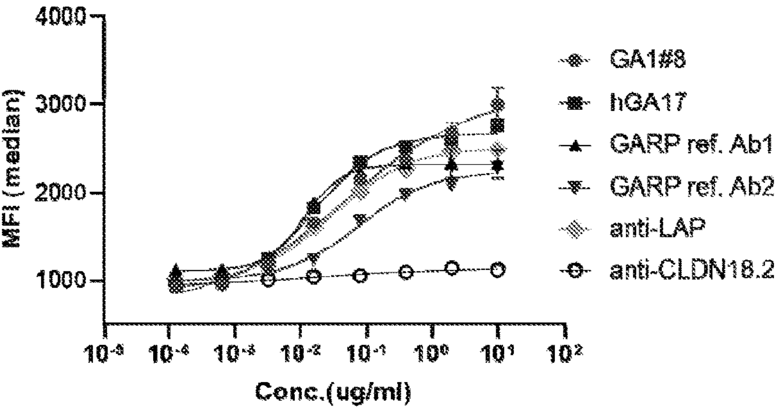
Figure 16D:
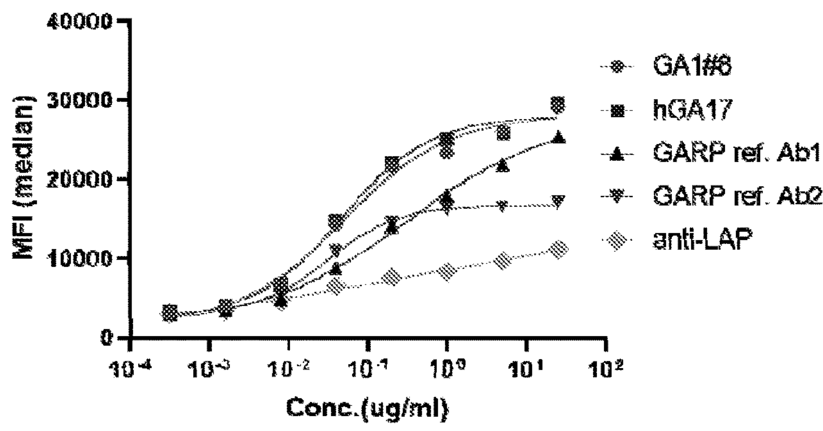

As shown in FIGS. 16A-16D, hGA17 bound to human GARP/TGFβ complex expressed on Hs 578T tumor cells (FIG. 16A), human GARP expressed on CHO-S cells (FIG. 16B) as well as the human GARP/latent TGFβ1 complex on human platelets (FIG. 16C) and activated human Treg cells (FIG. 16D). hGA17 showed much stronger binding activity towards Hs 578T tumor cells than GA1 #8, GARP ref. Abl and GARP ref. Ab2 as shown in FIG. 16A. Furthermore, hGA17 and GARP ref. Ab2 were able to bind human GARP on CHO-S cells and human GARP/latent TGFβ1 complex on human platelets and activated human Treg cells as shown in FIG. 16B. In contrast, GA1 #8 and GARP ref. Abl did not bind to human GARP on CHO cells as shown in FIG. 16B. The ability to target both human GARP outside of a GARP/TGFβ complex and human GARP/TGFβ1 complex can give hGA17 an advantage, as its therapeutic efficacy can be induced by both formats of GARP, thus mediating more extensive ADCC effects. Furthermore, as shown in FIGS. 16C and 16D, hGA17 exhibited higher binding ability to human platelets and Treg cells compared to the GARP ref. Ab2, indicating better binding ability of hGA17 to human GARP/latent TGFβ1 complex compared with GARP ref. Ab2.

Furthermore, hGA17's ability to inhibit the release of mature TGFβ1 from activated platelets was tested. Platelets were from Miao Tong Biological Science & Technology. DMEM medium pre-washed platelets were seeded to 96-well plates and incubated with indicated antibodies at 4 C° for 1 hour and then stimulated by thrombin (Sigma) at 2 U/mL for 1 hour with shaking at 1000 rpm in the presence or absence of indicated Abs. After stimulation, the supernatant of the reaction was harvested for mature TGFβ1 quantification. Mature TGFβ1 quantification was determined according to the manufacturer's instruction without acidification by TGFβ1 Duoset® ELISA kit (R&D). GARP ref. Abl, the ABBV-151 analog and GARP ref. Ab2, the DS-1055a analog were used as positive controls.

Figure 17:
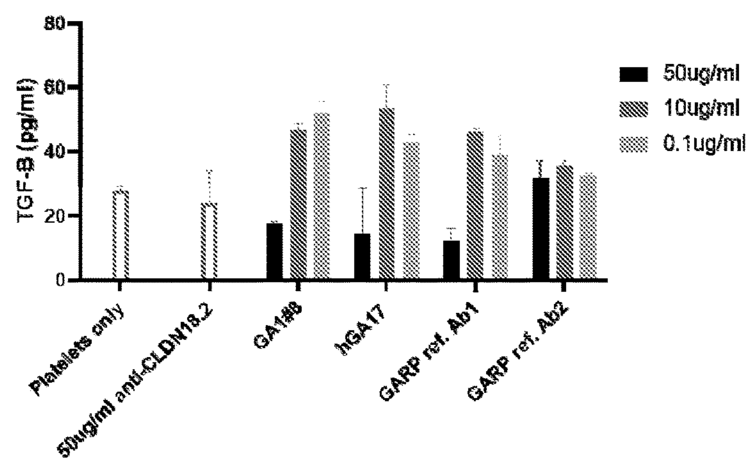
FIG. 17 depicts the ability of anti-GARP/TGFβ antibodies to inhibit TGFβ1 release from thrombin-activated platelets.

As shown in FIG. 17, compared to platelets only samples, GA1 #8 and hGA17 inhibited mature TGFβ1 release from thrombin-activated human platelets at a dose of 50 μg/ml. GARP ref. Ab1 showed a similar pattern of inhibition TGFβ1 release from thrombin-activated human platelets, however, the inhibition effect of GARP ref. Ab2 was not observed in this assay.

Furthermore, hGA17's ability to reduce Treg-mediated T cell suppression was tested. Human CD3$^{+}$ T cells were purchased from Miao Tong Biological Science & Technology. Treg cells were isolated from human PBMC (Miao Tong Biological Science & Technology) by EasySep human CD4+CD127$^{low}$ CD25+ regulatory T cell isolation kit (Stemcell) according to the instructions provided by the manufacturer. CD3+ T cells ($1\times10^5$) were stimulated by anti-CD3/CD28 Dynabeads (Gibco) at a bead-to-cell ratio of 1:10 with or without Treg cells ($5\times10^4$) in the presence or absence of indicated antibodies for 3 days. After incubation, the culture supernatants were collected for IL-2 quantification. The amount of IL-2 was measured by Human IL-2 ELISA MAX Deluxe kit (Biolegend) according to the manufacturer's instruction. Human IgG1 (Sino) was used as a negative control. GARP ref Abl, the ABBV-151 analog, was used as a positive control.

Figure 18:
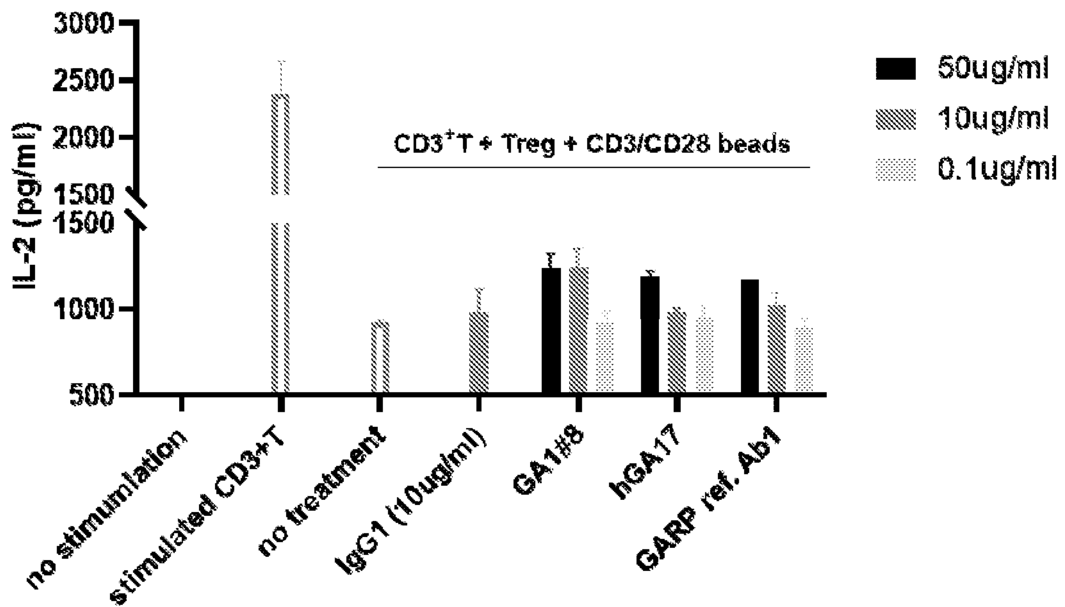
FIG. 18 depicts the ability of anti-GARP/TGFβ antibodies to reduce Treg-mediated suppression of CD3+ T cells.

As shown in FIG. 18, IL-2 secretion from CD3+ T cells was stimulated by anti-CD3/CD28 beads compared to no stimulation sample, whereas the addition of Treg suppressed the IL-2 secretion. GA1 #8, hGA17 and GARP ref. Ab1 reduced the Treg suppression of the IL-2 secretion, whereas the isotype control antibody did not reduce the Treg suppression of the IL-2 secretion. As IL-2 is an important cytokine of immune activation, the results indicated that GA1 #8 and hGA17 can improve the anti-tumor immunity of a patient.

hGA17 was further tested for their ability to promote NK cell-mediated lysis of GARP/TGFβ complex expressing tumor cells as follows. Briefly, Hs 578T tumor cells were used as target cells. PBMC were used as effectors cells. PBMC were mixed with Hs 578T (10000 cells/well) at the effect cell to target cells (E/T) ratio of 20:1 in the presence of antibody at a series dilution (10000 ng/ml to 0.1 ng/ml) over night. GARP ref Ab1, the ABBV-151 analog and GARP ref. Ab2, the DS-1055a analog were used as controls. Cytotoxicity was measured follow the instruction of Cytotoxicity LDH Assay Kit-WST (Dojindi, CK12). The percentage of antibody-dependent cell lysis was calculated based on OD490 read out with the following formula: [(test-mean background)/(mean maximum-mean background)]×100. PBMCs isolated from two healthy donors were tested.

Figure 19A:
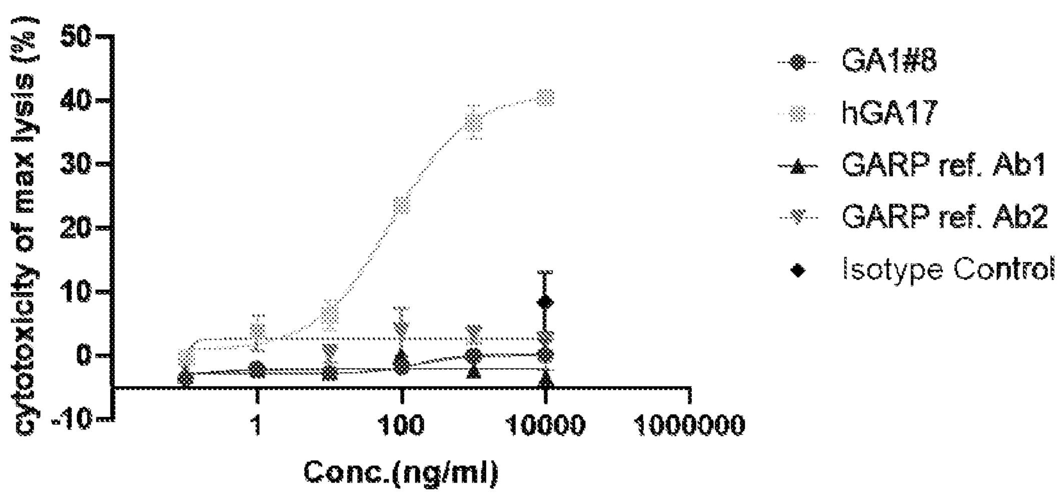
FIGS. 19A and 19B depict anti-GARP/TGFβ antibodies' ADCC effects on Hs 578T cells at the presence of PBMCs from donor 1 (19A) and donor 2 (19B).
Figure 19B:
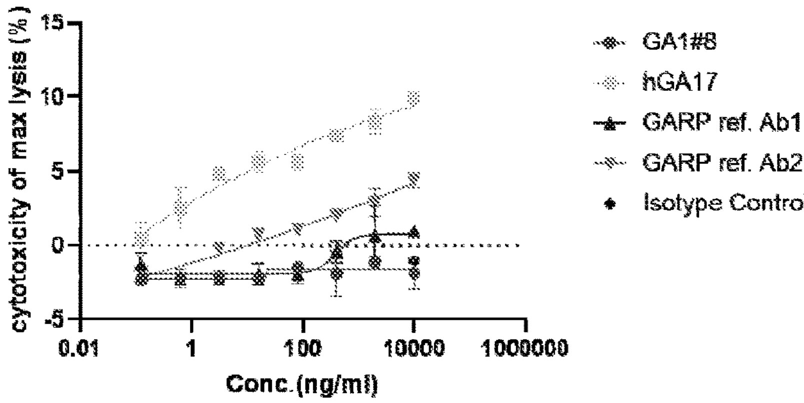

As shown in FIGS. 19A and 19B, hGA17 induced strong cytotoxicity in a dose-depend manner, while other anti-GARP/TGFβ antibodies only induced weak or no cytotoxicity towards Hs 578T cells. The superior ADCC effects of hGA17 indicated that hGA17 can have improved anti-tumor efficacy in tumors having high GARP/TGFβ complex expression.

Furthermore, hGA17's ability to deplete GARP$^{+}$Treg cells were tested. Human PBMCs from four healthy donors (Miao Tong Biological Science & Technology) were cultured in RPMI 1640 with CD3/CD28 dynabeads (Gibco) in the presence of anti-human GARP/TGFβ antibodies or human IgG1 (Sino). GARP ref. Ab2, the DS-1055a analog were used as a control. After two days of culture, the cells were washed and stained with LIVE/DEAD (ThermoFisher), Alexa Flour 700-CD3 (Biolegend), PE/CY7-CD4 (Biolegend), PE/CY5.5-CD25 (Biolegend), Pacific Blue-FOXP3 (Biolegend), PE-GARP (BD). Stained cells were evaluated with a CytoFLEX platform (Beckman Coulter), and the reduction of GARP⁺Treg cell population in the CD3⁺CD25⁺CD4⁺FOXP3⁺ T-cell population was determined.

Figure 20:
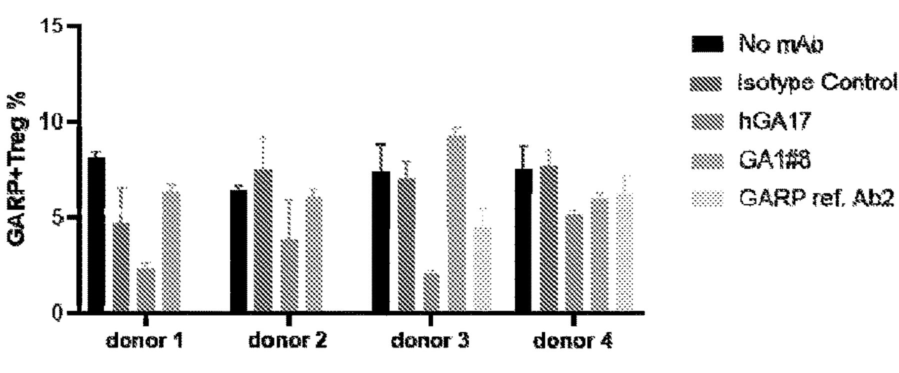
FIG. 20 depicts the ability of anti-GARP/TGFβ antibodies to deplete GARP+ Treg cells in PBMCs from four donors.

As shown in FIG. 20, hGA17 reduced GARP⁺Treg population in four different donors to a greater degree than all other anti-GARP/TGFβ antibodies. The results indicated that hGA17 had superior Treg depletion activity compared to other anti-GARP/TGFβ antibodies and can improve antitumor efficacy by reducing Treg population in the tumor microenvironment.

GA1 #8 can cross react with mouse GARP/TGFβ complex while hGA17, GARP ref. Abl and GARP ref Ab2cannot bind to mouse GARP. To compare the in vivo antitumor efficacy of GA1 #8, hGA17 and the reference antibodies, human GARP knock in (KI) c57/BL6 mice were used for the MC38 colon cancer model. GARP ref Abl, the ABBV-151 analog and GARP ref Ab2, the DS-1055a analog were used as controls.

A total of $5\times10^5$ MC38 cells in 100 μL of PBS were mixed with 100 L of Matrigel (Corning, CA, USA) (in a 1:1 ratio) and subcutaneously implanted into the forelimbs of mice. When tumor size reached 80-100 $mm^3$, indicated antibodies in each group or vehicle were administered intraperitoneally at a dose of 25 mg/kg, twice per week for 3 weeks. Tumors were observed and measured twice a week. Tumor volume was defined as TV (tumor volume)=(length×width2)/2. All data points represent means±SEM. Tumor growth inhibition (TGI) was calculated by comparing the tumor volume of each treatment group with the vehicle control group. Mice were sacrificed on day 24, and the spleens and blood were harvested. The spleens were prepared as single cell suspension by grinding and filtering with 40 pm Cell Strainer (Falcon®) by centrifugation at 400g 4° C. The pellets were suspended with 5 ml of 1x RBC Lysis Buffer (Invitrogen) per spleen and incubate at room temperature for 4 minutes. Red blood cell lysis was stopped with 30 ml of PBS buffer. Mouse blood were lysis with 1 ml of 1x RBC Lysis Buffer per 1 ml of mouse blood for 4 minutes and red blood cell lysis were stopped with 30 ml of PBS buffer. Pellets of spleen and blood cells were collected and stained with surface markers (Live/dead-eflour 506, mCD45-BV605, mCD3-AF700, mCD4-APC-H7, mCD8-Percp-cy5.5, mCD25-PE-cy7, mPD1-APC, hGARP-BV421/mGARP-BV421). After wash with FACS buffer (PBS with 2% FBS), cell pellets were suspended with Foxp3 Fixation/Permeabilization and incubated at 4 C° for 16 hours. After wash with 1× Permeabilization Buffer for 2 times, cells were stained with mFOXP3-PE at 4 C° in the dark for 30 minutes. Finally, cells were washed with 1× Permeabilization Buffer for 2 times and suspended with FACS buffer for flow cytometry analysis.

Figure 21A:
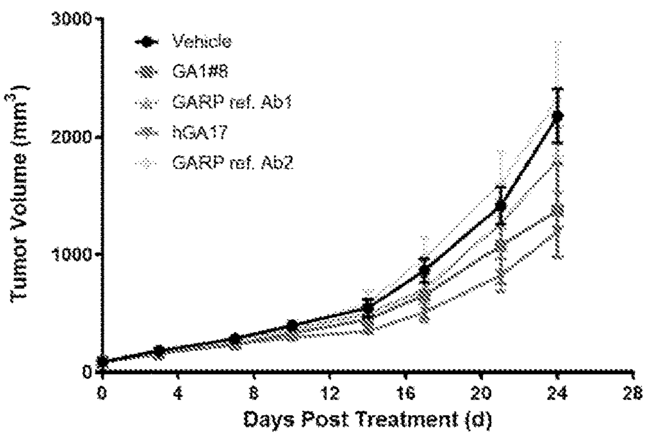
FIGS. 21A-21C depict anti-GARP/TGFβ antibodies' ability to inhibit tumor growth in MC38 mouse colon cancer model.
Figure 21B:
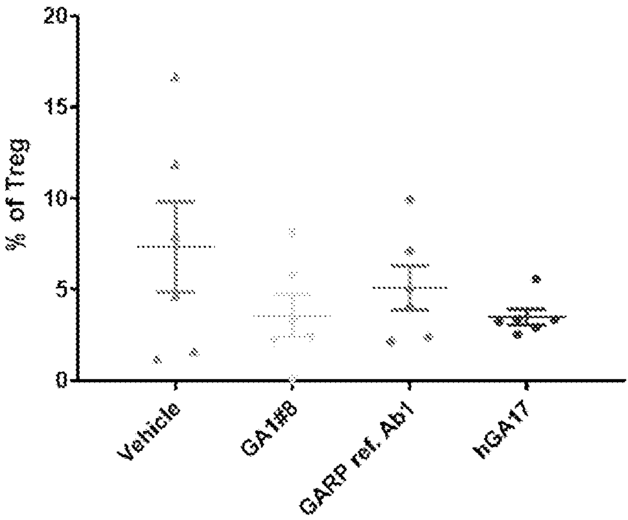
Figure 21C:
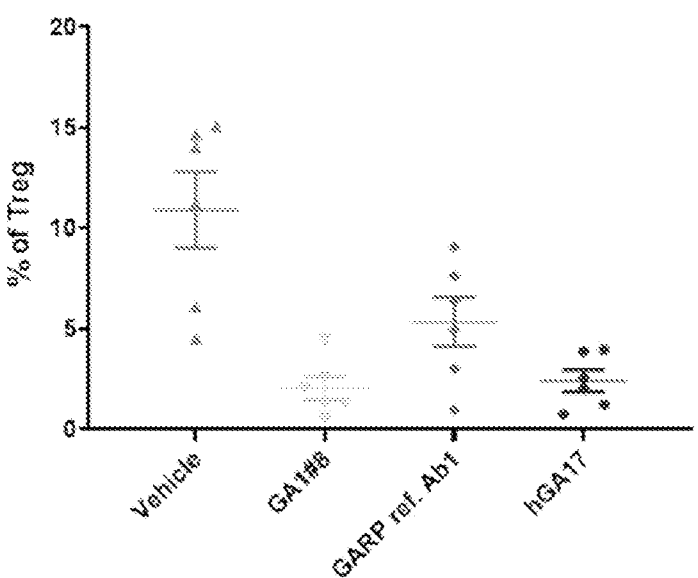

As showed in FIG. 21A, both hGA17 and GA1 #8 showed antitumor efficacy in the human GARP KI MC38 mouse model. The tumor growth inhibition (TGI) of hGA17 and GA1 #8 was 45.81% and 38.55%, respectively, compared to the vehicle control group on day 24. In contrast, on day 24, GARP ref. Abl showed much less tumor growth inhibition (TGI=16.57%), whereas GARP ref. Ab2 treatment did not show tumor inhibition compared to the vehicle control group. Moreover, Treg cells from blood and spleen of human GARP KI mice were analyzed by flow cytometry. As showed in FIGS. 21B and 21C, each antibody treatment group decreased GARP⁺ Treg cells in the blood (FIG. 21B) and the spleens (FIG. 21C) of the hGARP KI mice. These results demonstrated that GA1 #8 and hGA17 showed superior antitumor efficacy and better ability to deplete GARP⁺Treg cells in vivo compared to the reference antibodies.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

Various publications, patents and patent applications are cited herein, the contents of which are hereby incorporated by reference in their entireties.

What is claimed is:

1. An antibody that binds to a GARP/TGFβ complex comprising:

a) a heavy chain variable domain (VH) sequence comprising (1) a CDR-H1 comprising the amino acid sequence set forth in SEQ ID NO: 1, (2) a CDR-H2 comprising the amino acid sequence set forth in SEQ ID NO: 2, and (3) a CDR-H3 comprising the amino acid sequence set forth in SEQ ID NO: 3; and a light chain variable domain (VL) sequence comprising (1) a CDR-L1 comprising the amino acid sequence set forth in SEQ ID NO: 4, (2) a CDR-L2 comprising the amino acid sequence set forth in SEQ ID NO: 5, and (3) a CDR-L3 comprising the amino acid sequence set forth in SEQ ID NO: 6;

b) a heavy chain variable domain (VH) sequence comprising (1) a CDR-H1 comprising the amino acid sequence set forth in SEQ ID NO: 11, (2) a CDR-H2 comprising the amino acid sequence set forth in SEQ ID NO: 12, and (3) a CDR-H3 comprising the amino acid sequence set forth in SEQ ID NO: 13; and a light chain variable domain (VL) sequence comprising (1) a CDR-L1 comprising the amino acid sequence set forth in SEQ ID NO: 14, (2) a CDR-L2 comprising the amino acid sequence set forth in SEQ ID NO: 15, and (3) a CDR-L3 comprising the amino acid sequence set forth in SEQ ID NO: 16;

c) a heavy chain variable domain (VH) sequence comprising (1) a CDR-H1 comprising the amino acid sequence set forth in SEQ ID NO: 21, (2) a CDR-H2 comprising the amino acid sequence set forth in SEQ ID NO: 22, and (3) a CDR-H3 comprising the amino acid sequence set forth in SEQ ID NO: 23; and a light chain variable domain (VL) sequence comprising (1) a CDR-L1 comprising the amino acid sequence set forth in SEQ ID NO: 24, (2) a CDR-L2 comprising the amino acid sequence set forth in SEQ ID NO: 25, and (3) a CDR-L3 comprising the amino acid sequence set forth in SEQ ID NO: 26;

d) a heavy chain variable domain (VH) sequence comprising (1) a CDR-H1 comprising the amino acid sequence set forth in SEQ ID NO: 31, (2) a CDR-H2 comprising the amino acid sequence set forth in SEQ ID NO: 32, and (3) a CDR-H3 comprising the amino acid sequence set forth in SEQ ID NO: 33; and a light chain variable domain (VL) sequence comprising (1) a CDR-L1 comprising the amino acid sequence set forth in SEQ ID NO: 34, (2) a CDR-L2 comprising the amino acid sequence set forth in SEQ ID NO: 35, and (3) a CDR-L3 comprising the amino acid sequence set forth in SEQ ID NO: 36;

e) a heavy chain variable domain (VH) sequence comprising (1) a CDR-H1 comprising the amino acid sequence set forth in SEQ ID NO: 41, (2) a CDR-H2 comprising the amino acid sequence set forth in SEQ ID NO: 42, and (3) a CDR-H3 comprising the amino acid sequence set forth in SEQ ID NO: 43; and a light chain variable domain (VL) sequence comprising (1) a CDR-L1 comprising the amino acid sequence set forth in SEQ ID NO: 44, (2) a CDR-L2 comprising the amino acid sequence set forth in SEQ ID NO: 45, and (3) a CDR-L3 comprising the amino acid sequence set forth in SEQ ID NO: 46;

f) a heavy chain variable domain (VH) sequence comprising (1) a CDR-H1 comprising the amino acid sequence set forth in SEQ ID NO: 51, (2) a CDR-H2 comprising the amino acid sequence set forth in SEQ ID NO: 52, and (3) a CDR-H3 comprising the amino acid sequence set forth in SEQ ID NO: 53; and a light chain variable domain (VL) sequence comprising (1) a CDR-L1 comprising the amino acid sequence set forth in SEQ ID NO: 54, (2) a CDR-L2 comprising the amino acid sequence set forth in SEQ ID NO: 55, and (3) a CDR-L3 comprising the amino acid sequence set forth in SEQ ID NO: 56;

g) a heavy chain variable domain (VH) sequence comprising (1) a CDR-H1 comprising the amino acid sequence set forth in SEQ ID NO: 61, (2) a CDR-H2 comprising the amino acid sequence set forth in SEQ ID NO: 62, and (3) a CDR-H3 comprising the amino acid sequence set forth in SEQ ID NO: 63; and a light chain variable domain (VL) sequence comprising (1) a CDR-L1 comprising the amino acid sequence set forth in SEQ ID NO: 64, (2) a CDR-L2 comprising the amino acid sequence set forth in SEQ ID NO: 65, and (3) a CDR-L3 comprising the amino acid sequence set forth in SEQ ID NO: 66; or h) a heavy chain variable domain (VH) sequence comprising (1) a CDR-H1 comprising the amino acid sequence set forth in SEQ ID NO: 105, (2) a CDR-H2 comprising the amino acid sequence set forth in SEQ ID NO: 106, and (3) a CDR-H3 comprising the amino acid sequence set forth in SEQ ID NO: 107; and a light chain variable domain (VL) sequence comprising (1) a CDR-L1 comprising the amino acid sequence set forth in SEQ ID NO: 108, (2) a CDR-L2 comprising the amino acid sequence set forth in SEQ ID NO: 109, and (3) a CDR-L3 comprising the amino acid sequence set forth in SEQ ID NO: 110.

2. The antibody of claim 1, wherein the antibody comprises a heavy chain variable domain (VH) sequence comprising (1) a CDR-H1 comprising the amino acid sequence set forth in SEQ ID NO: 41, (2) a CDR-H2 comprising the amino acid sequence set forth in SEQ ID NO: 42, and (3) a CDR-H3 comprising the amino acid sequence set forth in SEQ ID NO: 43; and a light chain variable domain (VL) sequence comprising (1) a CDR-L1 comprising the amino acid sequence set forth in SEQ ID NO: 44, (2) a CDR-L2 comprising the amino acid sequence set forth in SEQ ID NO: 45, and (3) a CDR-L3 comprising the amino acid sequence set forth in SEQ ID NO: 46.

3. The antibody of claim 1, wherein the antibody comprises a heavy chain variable domain (VH) sequence comprising (1) a CDR-H1 comprising the amino acid sequence set forth in SEQ ID NO: 105, (2) a CDR-H2 comprising the amino acid sequence set forth in SEQ ID NO: 106, and (3) a CDR-H3 comprising the amino acid sequence set forth in SEQ ID NO: 107; and a light chain variable domain (VL) sequence comprising (1) a CDR-L1 comprising the amino acid sequence set forth in SEQ ID NO: 108, (2) a CDR-L2 comprising the amino acid sequence set forth in SEQ ID NO: 109, and (3) a CDR-L3 comprising the amino acid sequence set forth in SEQ ID NO: 110.

4. The antibody of claim 1, wherein the antibody comprises:

a) a heavy chain variable region comprising the amino acid sequence set forth in SEQ ID NO: 7, and a light chain variable region comprising the amino acid sequence set forth in SEQ ID NO: 8;

b) a heavy chain variable region comprising the amino acid sequence set forth in SEQ ID NO: 17, and a light chain variable region comprising the amino acid sequence set forth in SEQ ID NO: 18;

c) a heavy chain variable region comprising the amino acid sequence set forth in SEQ ID NO: 27, and a light chain variable region comprising the amino acid sequence set forth in SEQ ID NO: 28;

d) a heavy chain variable region comprising the amino acid sequence set forth in SEQ ID NO: 37, and a light chain variable region comprising the amino acid sequence set forth in SEQ ID NO: 38;

e) a heavy chain variable region comprising the amino acid sequence set forth in SEQ ID NO: 37, and a light chain variable region comprising the amino acid sequence set forth in SEQ ID NO: 83;

f) a heavy chain variable region comprising the amino acid sequence set forth in SEQ ID NO: 47, and a light chain variable region comprising the amino acid sequence set forth in SEQ ID NO: 48;

g) a heavy chain variable region comprising the amino acid sequence set forth in SEQ ID NO: 47, and a light chain variable region comprising the amino acid sequence set forth in SEQ ID NO: 84;

h) a heavy chain variable region comprising the amino acid sequence set forth in SEQ ID NO: 57, and a light chain variable region comprising the amino acid sequence set forth in SEQ ID NO: 58;

i) a heavy chain variable region comprising the amino acid sequence set forth in SEQ ID NO: 67, and a light chain variable region comprising the amino acid sequence set forth in SEQ ID NO: 68;

j) a heavy chain variable region comprising the amino acid sequence set forth in SEQ ID NO: 85, and a light chain variable region comprising the amino acid sequence set forth in SEQ ID NO: 86;

k) a heavy chain variable region comprising the amino acid sequence set forth in SEQ ID NO: 89, and a light chain variable region comprising the amino acid sequence set forth in SEQ ID NO: 90;

l) a heavy chain variable region comprising the amino acid sequence set forth in SEQ ID NO: 93, and a light chain variable region comprising the amino acid sequence set forth in SEQ ID NO: 94;

m) a heavy chain variable region comprising the amino acid sequence set forth in SEQ ID NO: 97, and a light chain variable region comprising the amino acid sequence set forth in SEQ ID NO: 98;

n) a heavy chain variable region comprising the amino acid sequence set forth in SEQ ID NO: 101, and a light chain variable region comprising the amino acid sequence set forth in SEQ ID NO: 102; or o) a heavy chain variable region comprising the amino acid sequence set forth in SEQ ID NO: 111, and a light chain variable region comprising the amino acid sequence set forth in SEQ ID NO: 112.

5. The antibody of claim 4, wherein the antibody comprises a heavy chain variable region comprising the amino acid sequence set forth in SEQ ID NO: 85, and a light chain variable region comprising the amino acid sequence set forth in SEQ ID NO: 86.

6. The antibody of claim 4, wherein the antibody comprises a heavy chain variable region comprising the amino acid sequence set forth in SEQ ID NO: 111, and a light chain variable region comprising the amino acid sequence set forth in SEQ ID NO: 112.

7. The antibody of claim 1, wherein the antibody comprises a full-length immunoglobulin, a single-chain Fv (scFv) fragment, a Fab fragment, a Fab' fragment, a F(ab')2, a Fv fragment, a disulfide stabilized Fv fragment (dsFv), a (dsFv)2, a Fv-Fc fusion, a scFv-Fc fusion, a scFv-Fv fusion, a diabody, a tribody, a tetrabody or any combination thereof.

8. The antibody of claim 1, wherein the antibody comprises a Fc region.

9. The antibody of claim 8, wherein the Fc region comprises a Fc region selected from the group consisting of the Fc regions of IgG1, IgG2, IgG3 and IgG4.

10. The antibody of claim 9, wherein the Fc region comprises an IgG1 Fc region or an IgG4 Fc region.

11. The antibody of claim 8, wherein the Fc region comprises a C-terminal lysine.

12. The antibody of claim 8, wherein the Fc region comprises a deletion of a C-terminal lysine.

13. An immunoconjugate comprising the antibody of claim 1, linked to a therapeutic agent or a label.

14. An antigen-recognizing receptor comprising an extracellular antigen-binding domain that comprises an antibody of claim 1.

15. An immunoresponsive cell comprising an antigen-recognizing receptor of claim 14.

16. A pharmaceutical composition comprising a) the antibody of claim 1, and b) a pharmaceutically acceptable carrier.

17. A method for reducing tumor burden in a subject having regulatory T-lymphocytes (Tregs) that express a GARP/TGF-beta complex, the method comprising administering to the subject an effective amount of a pharmaceutical composition of claim 16.

18. A kit comprising an antibody of claim 1.

19. A method of treating cancer in a subject having regulatory T-lymphocytes (Tregs) that express a GARP/TGF-beta complex comprising administering to the subject an effective amount of an anti-GARP/TGFβ antibody and an anti-PD1 antibody, wherein the anti-GARP/TGFβ antibody is an anti-GARP/TGFβ antibody of claim 1.

* * * * *

SEQUENCE LISTING

```
Sequence total quantity: 145
SEQ ID NO: 1           moltype = AA  length = 5
FEATURE                Location/Qualifiers
DOMAIN                 1..5
                       note = Clone GA1 VH CDR1
source                 1..5
                       mol_type = protein
                       organism = synthetic construct
SEQUENCE: 1
SYAMH                                                             5

SEQ ID NO: 2           moltype = AA  length = 17
FEATURE                Location/Qualifiers
DOMAIN                 1..17
                       note = Clone GA1 VH CDR2
source                 1..17
                       mol_type = protein
                       organism = synthetic construct
```

```
SEQUENCE: 2
VISYDGSNKY YADSVKG                                                     17

SEQ ID NO: 3             moltype = AA  length = 13
FEATURE                  Location/Qualifiers
DOMAIN                   1..13
                         note = Clone GA1 VH CDR3
source                   1..13
                         mol_type = protein
                         organism = synthetic construct
SEQUENCE: 3
DVLRTYYYYG MDV                                                         13

SEQ ID NO: 4             moltype = AA  length = 11
FEATURE                  Location/Qualifiers
DOMAIN                   1..11
                         note = Clone GA1 VL CDR1
source                   1..11
                         mol_type = protein
                         organism = synthetic construct
SEQUENCE: 4
SGDALPDRYT Y                                                           11

SEQ ID NO: 5             moltype = AA  length = 7
FEATURE                  Location/Qualifiers
DOMAIN                   1..7
                         note = Clone GA1 VL CDR2
source                   1..7
                         mol_type = protein
                         organism = synthetic construct
SEQUENCE: 5
SDNERPS                                                                7

SEQ ID NO: 6             moltype = AA  length = 8
FEATURE                  Location/Qualifiers
DOMAIN                   1..8
                         note = Clone GA1 VL CDR3
source                   1..8
                         mol_type = protein
                         organism = synthetic construct
SEQUENCE: 6
QSADDTYT                                                               8

SEQ ID NO: 7             moltype = AA  length = 122
FEATURE                  Location/Qualifiers
DOMAIN                   1..122
                         note = Clone GA1 VH
source                   1..122
                         mol_type = protein
                         organism = synthetic construct
SEQUENCE: 7
QVQLVQSGGG VVQPGRSLRL SCAASGFTFS SYAMHQVRQA PGKGLEWVAV ISYDGSNKYY  60
ADSVKGRFTI SRDNSKNTLY LQMNSLRAED TAVYYCARDV LRTYYYYGMD VWGQGTTVTV  120
SS                                                                 122

SEQ ID NO: 8             moltype = AA  length = 109
FEATURE                  Location/Qualifiers
DOMAIN                   1..109
                         note = Clone GA1 VL
source                   1..109
                         mol_type = protein
                         organism = synthetic construct
SEQUENCE: 8
LSYELTQPPS VSVFPGQTAR ITCSGDALPD RYTYWYQQKP GQAPVLVIYS DNERPSGIPE  60
RFSGSSSGTI ATLTINGVQA EDEADYYCQS ADDTYTFGGG TKLTVLGQP              109

SEQ ID NO: 9             moltype = AA  length = 452
FEATURE                  Location/Qualifiers
CHAIN                    1..452
                         note = Clone GA1 HC
source                   1..452
                         mol_type = protein
                         organism = synthetic construct
SEQUENCE: 9
QVQLVQSGGG VVQPGRSLRL SCAASGFTFS SYAMHQVRQA PGKGLEWVAV ISYDGSNKYY  60
ADSVKGRFTI SRDNSKNTLY LQMNSLRAED TAVYYCARDV LRTYYYYGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
```

```
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 10          moltype = AA  length = 212
FEATURE                Location/Qualifiers
CHAIN                  1..212
                       note = Clone GA1 LC
source                 1..212
                       mol_type = protein
                       organism = synthetic construct
SEQUENCE: 10
LSYELTQPPS VSVFPGQTAR ITCSGDALPD RYTYWYQQKP GQAPVLVIYS DNERPSGIPE  60
RFSGSSSGTI ATLTINGVQA EDEADYYCQS ADDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 11          moltype = AA  length = 5
FEATURE                Location/Qualifiers
DOMAIN                 1..5
                       note = Clone GA1#4 VH CDR1
source                 1..5
                       mol_type = protein
                       organism = synthetic construct
SEQUENCE: 11
SYAMH                                                              5

SEQ ID NO: 12          moltype = AA  length = 17
FEATURE                Location/Qualifiers
DOMAIN                 1..17
                       note = Clone GA1#4 VH CDR2
source                 1..17
                       mol_type = protein
                       organism = synthetic construct
SEQUENCE: 12
TISYDGSNKI YADSVKG                                                 17

SEQ ID NO: 13          moltype = AA  length = 13
FEATURE                Location/Qualifiers
DOMAIN                 1..13
                       note = Clone GA1#4 VH CDR3
source                 1..13
                       mol_type = protein
                       organism = synthetic construct
SEQUENCE: 13
DSLRTYYYTG MDV                                                     13

SEQ ID NO: 14          moltype = AA  length = 11
FEATURE                Location/Qualifiers
DOMAIN                 1..11
                       note = Clone GA1#4 VL CDR1
source                 1..11
                       mol_type = protein
                       organism = synthetic construct
SEQUENCE: 14
SGDALPDRYT Y                                                       11

SEQ ID NO: 15          moltype = AA  length = 7
FEATURE                Location/Qualifiers
DOMAIN                 1..7
                       note = Clone GA1#4 VL CDR2
source                 1..7
                       mol_type = protein
                       organism = synthetic construct
SEQUENCE: 15
SDNERPV                                                            7

SEQ ID NO: 16          moltype = AA  length = 8
FEATURE                Location/Qualifiers
DOMAIN                 1..8
                       note = Clone GA1#4 VL CDR3
source                 1..8
                       mol_type = protein
                       organism = synthetic construct
SEQUENCE: 16
QSSDDTYT                                                           8

SEQ ID NO: 17          moltype = AA  length = 122
FEATURE                Location/Qualifiers
```

```
DOMAIN                 1..122
                       note = Clone GA1#4 VH
source                 1..122
                       mol_type = protein
                       organism = synthetic construct
SEQUENCE: 17
QVQLVQSGGG VVQPGRSLRL SCAASGFTFS SYAMHQVRQA PGKGLEWVAT ISYDGSNKIY  60
ADSVKGRFTI SRDNSKNTLY LQMNSLRAED TAVYYCARDS LRTYYYTGMD VWGQGTTVTV  120
SS                                                                122

SEQ ID NO: 18          moltype = AA  length = 109
FEATURE                Location/Qualifiers
DOMAIN                 1..109
                       note = Clone GA1#4 VL
source                 1..109
                       mol_type = protein
                       organism = synthetic construct
SEQUENCE: 18
LSYELTQPPS VSVFPGQTAR ITCSGDALPD RYTYWYQQKP GQAPVLVIYS DNERPVGIPE  60
RFSGSSSGTI ATLTINGVQA EDEADYYCQS SDDTYTFGGG TKLTVLGQP             109

SEQ ID NO: 19          moltype = AA  length = 451
FEATURE                Location/Qualifiers
CHAIN                  1..451
                       note = Clone GA1#4 HC
source                 1..451
                       mol_type = protein
                       organism = synthetic construct
SEQUENCE: 19
QVQLVQSGGG VVQPGRSLRL SCAASGFTFS SYAMHQVRQA PGKGLEWVAT ISYDGSNKIY  60
ADSVKGRFTI SRDNSKNTLY LQMNSLRAED TAVYYCARDS LRTYYYTGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 20          moltype = AA  length = 212
FEATURE                Location/Qualifiers
CHAIN                  1..212
                       note = Clone GA1#4 LC
source                 1..212
                       mol_type = protein
                       organism = synthetic construct
SEQUENCE: 20
LSYELTQPPS VSVFPGQTAR ITCSGDALPD RYTYWYQQKP GQAPVLVIYS DNERPVGIPE  60
RFSGSSSGTI ATLTINGVQA EDEADYYCQS SDDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                               212

SEQ ID NO: 21          moltype = AA  length = 5
FEATURE                Location/Qualifiers
DOMAIN                 1..5
                       note = Clone GA1#6 VH CDR1
source                 1..5
                       mol_type = protein
                       organism = synthetic construct
SEQUENCE: 21
SYAMH                                                             5

SEQ ID NO: 22          moltype = AA  length = 17
FEATURE                Location/Qualifiers
DOMAIN                 1..17
                       note = Clone GA1#6 VH CDR2
source                 1..17
                       mol_type = protein
                       organism = synthetic construct
SEQUENCE: 22
SISYDGSNVY YADSVKG                                                17

SEQ ID NO: 23          moltype = AA  length = 13
FEATURE                Location/Qualifiers
DOMAIN                 1..13
                       note = Clone GA1#6 VH CDR3
source                 1..13
                       mol_type = protein
                       organism = synthetic construct
```

```
SEQUENCE: 23
DVLRTYYYMG MDV                                                    13

SEQ ID NO: 24           moltype = AA  length = 11
FEATURE                 Location/Qualifiers
DOMAIN                  1..11
                        note = Clone GA1#6 VL CDR1
source                  1..11
                        mol_type = protein
                        organism = synthetic construct
SEQUENCE: 24
SGDALPDRYT Y                                                      11

SEQ ID NO: 25           moltype = AA  length = 7
FEATURE                 Location/Qualifiers
DOMAIN                  1..7
                        note = Clone GA1#6 VL CDR2
source                  1..7
                        mol_type = protein
                        organism = synthetic construct
SEQUENCE: 25
SDNERPV                                                           7

SEQ ID NO: 26           moltype = AA  length = 8
FEATURE                 Location/Qualifiers
DOMAIN                  1..8
                        note = Clone GA1#6 VL CDR3
source                  1..8
                        mol_type = protein
                        organism = synthetic construct
SEQUENCE: 26
QSSDDTYT                                                          8

SEQ ID NO: 27           moltype = AA  length = 122
FEATURE                 Location/Qualifiers
DOMAIN                  1..122
                        note = Clone GA1#6 VH
source                  1..122
                        mol_type = protein
                        organism = synthetic construct
SEQUENCE: 27
QVQLVQSGGG VVQPGRSLRL SCAASGFTFS SYAMHQVRQA PGKGLEWVAS ISYDGSNVYY  60
ADSVKGRFTI SRDNSKNTLY LQMNSLRAED TAVYYCARDV LRTYYYMGMD VWGQGTTVTV  120
SS                                                                122

SEQ ID NO: 28           moltype = AA  length = 109
FEATURE                 Location/Qualifiers
DOMAIN                  1..109
                        note = Clone GA1#6 VL
source                  1..109
                        mol_type = protein
                        organism = synthetic construct
SEQUENCE: 28
LSYELTQPPS VSVFPGQTAR ITCSGDALPD RYTYWYQQKP GQAPVLVIYS DNERPVGIPE  60
RFSGSSSGTI ATLTINGVQA EDEADYYCQS SDDTYTFGGG TKLTVLGQP             109

SEQ ID NO: 29           moltype = AA  length = 451
FEATURE                 Location/Qualifiers
CHAIN                   1..451
                        note = Clone GA1#6 HC
source                  1..451
                        mol_type = protein
                        organism = synthetic construct
SEQUENCE: 29
QVQLVQSGGG VVQPGRSLRL SCAASGFTFS SYAMHQVRQA PGKGLEWVAS ISYDGSNVYY  60
ADSVKGRFTI SRDNSKNTLY LQMNSLRAED TAVYYCARDV LRTYYYMGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 30           moltype = AA  length = 212
FEATURE                 Location/Qualifiers
CHAIN                   1..212
                        note = Clone GA1#6 LC
```

```
source                  1..212
                        mol_type = protein
                        organism = synthetic construct
SEQUENCE: 30
LSYELTQPPS VSVFPGQTAR ITCSGDALPD RYTYWYQQKP GQAPVLVIYS DNERPVGIPE  60
RFSGSSSGTI ATLTINGVQA EDEADYYCQS SDDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 31           moltype = AA  length = 5
FEATURE                 Location/Qualifiers
DOMAIN                  1..5
                        note = Clone GA1#7 VH CDR1
source                  1..5
                        mol_type = protein
                        organism = synthetic construct
SEQUENCE: 31
SYAMH                                                              5

SEQ ID NO: 32           moltype = AA  length = 39
FEATURE                 Location/Qualifiers
DOMAIN                  1..39
                        note = Clone GA1#7 VH CDR2
source                  1..39
                        mol_type = protein
                        organism = synthetic construct
SEQUENCE: 32
VISYDGSQKY YADSVKGSYA MHVISYDGSQ KYYADSVKG                         39

SEQ ID NO: 33           moltype = AA  length = 13
FEATURE                 Location/Qualifiers
DOMAIN                  1..13
                        note = Clone GA1#7 VH CDR3
source                  1..13
                        mol_type = protein
                        organism = synthetic construct
SEQUENCE: 33
DALRTYYYYG MDV                                                     13

SEQ ID NO: 34           moltype = AA  length = 11
FEATURE                 Location/Qualifiers
DOMAIN                  1..11
                        note = Clone GA1#7 VL CDR1
source                  1..11
                        mol_type = protein
                        organism = synthetic construct
SEQUENCE: 34
SGDALPDRYT Y                                                       11

SEQ ID NO: 35           moltype = AA  length = 7
FEATURE                 Location/Qualifiers
DOMAIN                  1..7
                        note = Clone GA1#7 VL CDR2
source                  1..7
                        mol_type = protein
                        organism = synthetic construct
SEQUENCE: 35
SDNERPS                                                            7

SEQ ID NO: 36           moltype = AA  length = 8
FEATURE                 Location/Qualifiers
DOMAIN                  1..8
                        note = Clone GA1#7 VL CDR3
source                  1..8
                        mol_type = protein
                        organism = synthetic construct
SEQUENCE: 36
QSSDDTYT                                                           8

SEQ ID NO: 37           moltype = AA  length = 122
FEATURE                 Location/Qualifiers
DOMAIN                  1..122
                        note = Clone GA1#7 VH
source                  1..122
                        mol_type = protein
                        organism = synthetic construct
SEQUENCE: 37
QVQLVQSGGG VVQPGRSLRL SCAASGFTFS SYAMHQVRQA PGKGLEWVAV ISYDGSQKYY  60
ADSVKGRFTI SRDNSKNTLY LQMNSLRAED TAVYYCARDA LRTYYYYGMD VWGQGTTVTV  120
```

```
SS                                                            122

SEQ ID NO: 38           moltype = AA  length = 109
FEATURE                 Location/Qualifiers
DOMAIN                  1..109
                        note = Clone GA1#7 VL
source                  1..109
                        mol_type = protein
                        organism = synthetic construct
SEQUENCE: 38
LSYELTQPPS VSVFPGQTAR ITCSGDALPD RYTYWYQQKP GQAPVLVIYS DNERPSGIPE  60
RFSGSSSGTI ATLTINGVQA EDEADYYCQS SDDTYTFGGG TKLTVLGQP             109

SEQ ID NO: 39           moltype = AA  length = 451
FEATURE                 Location/Qualifiers
CHAIN                   1..451
                        note = Clone GA1#7 HC
source                  1..451
                        mol_type = protein
                        organism = synthetic construct
SEQUENCE: 39
QVQLVQSGGG VVQPGRSLRL SCAASGFTFS SYAMHQVRQA PGKGLEWVAV ISYDGSQKYY  60
ADSVKGRFTI SRDNSKNTLY LQMNSLRAED TAVYYCARDA LRTYYYYGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                451

SEQ ID NO: 40           moltype = AA  length = 212
FEATURE                 Location/Qualifiers
CHAIN                   1..212
                        note = Clone GA1#7 LC
source                  1..212
                        mol_type = protein
                        organism = synthetic construct
SEQUENCE: 40
LSYELTQPPS VSVFPGQTAR ITCSGDALPD RYTYWYQQKP GQAPVLVIYS DNERPSGIPE  60
RFSGSSSGTI ATLTINGVQA EDEADYYCQS SDDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                               212

SEQ ID NO: 41           moltype = AA  length = 5
FEATURE                 Location/Qualifiers
DOMAIN                  1..5
                        note = Clone GA1#8 VH CDR1
source                  1..5
                        mol_type = protein
                        organism = synthetic construct
SEQUENCE: 41
SYAMH                                                             5

SEQ ID NO: 42           moltype = AA  length = 17
FEATURE                 Location/Qualifiers
DOMAIN                  1..17
                        note = Clone GA1#8 VH CDR2
source                  1..17
                        mol_type = protein
                        organism = synthetic construct
SEQUENCE: 42
SISYDGSNKY YADSVKG                                                17

SEQ ID NO: 43           moltype = AA  length = 13
FEATURE                 Location/Qualifiers
DOMAIN                  1..13
                        note = Clone GA1#8 VH CDR3
source                  1..13
                        mol_type = protein
                        organism = synthetic construct
SEQUENCE: 43
DALRTYYYQG MDV                                                    13

SEQ ID NO: 44           moltype = AA  length = 11
FEATURE                 Location/Qualifiers
DOMAIN                  1..11
                        note = Clone GA1#8 VL CDR1
```

```
source                  1..11
                        mol_type = protein
                        organism = synthetic construct
SEQUENCE: 44
SGDALPDRYT Y                                             11

SEQ ID NO: 45           moltype = AA  length = 7
FEATURE                 Location/Qualifiers
DOMAIN                  1..7
                        note = Clone GA1#8 VL CDR2
source                  1..7
                        mol_type = protein
                        organism = synthetic construct
SEQUENCE: 45
SDNERPR                                                  7

SEQ ID NO: 46           moltype = AA  length = 8
FEATURE                 Location/Qualifiers
DOMAIN                  1..8
                        note = Clone GA1#8 VL CDR3
source                  1..8
                        mol_type = protein
                        organism = synthetic construct
SEQUENCE: 46
QSADYTYT                                                 8

SEQ ID NO: 47           moltype = AA  length = 122
FEATURE                 Location/Qualifiers
DOMAIN                  1..122
                        note = Clone GA1#8 VH
source                  1..122
                        mol_type = protein
                        organism = synthetic construct
SEQUENCE: 47
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SS                                                       122

SEQ ID NO: 48           moltype = AA  length = 109
FEATURE                 Location/Qualifiers
DOMAIN                  1..109
                        note = Clone GA1#8 VL
source                  1..109
                        mol_type = protein
                        organism = synthetic construct
SEQUENCE: 48
LSYELTQPPS VSVFPGQTAR ITCSGDALPD RYTYWYQQKP GQAPVLVIYS DNERPRGIPE  60
RFSGSSSGTI ATLTINGVQA EDEADYYCQS ADYTYTFGGG TKLTVLGQP          109

SEQ ID NO: 49           moltype = AA  length = 451
FEATURE                 Location/Qualifiers
CHAIN                   1..451
                        note = Clone GA1#8 HC
source                  1..451
                        mol_type = protein
                        organism = synthetic construct
SEQUENCE: 49
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                       451

SEQ ID NO: 50           moltype = AA  length = 212
FEATURE                 Location/Qualifiers
CHAIN                   1..212
                        note = Clone GA1#8 LC
source                  1..212
                        mol_type = protein
                        organism = synthetic construct
SEQUENCE: 50
LSYELTQPPS VSVFPGQTAR ITCSGDALPD RYTYWYQQKP GQAPVLVIYS DNERPRGIPE  60
RFSGSSSGTI ATLTINGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                      212
```

-continued

```
SEQ ID NO: 51          moltype = AA  length = 5
FEATURE                Location/Qualifiers
DOMAIN                 1..5
                       note = Clone GA1#9 VH CDR1
source                 1..5
                       mol_type = protein
                       organism = synthetic construct
SEQUENCE: 51
SYAMH                                                         5

SEQ ID NO: 52          moltype = AA  length = 17
FEATURE                Location/Qualifiers
DOMAIN                 1..17
                       note = Clone GA1#9 VH CDR2
source                 1..17
                       mol_type = protein
                       organism = synthetic construct
SEQUENCE: 52
SISYDGSNKY YADSVKG                                            17

SEQ ID NO: 53          moltype = AA  length = 13
FEATURE                Location/Qualifiers
DOMAIN                 1..13
                       note = Clone GA1#9 VH CDR3
source                 1..13
                       mol_type = protein
                       organism = synthetic construct
SEQUENCE: 53
DALRTYYYYG MDV                                                13

SEQ ID NO: 54          moltype = AA  length = 11
FEATURE                Location/Qualifiers
DOMAIN                 1..11
                       note = Clone GA1#9 VL CDR1
source                 1..11
                       mol_type = protein
                       organism = synthetic construct
SEQUENCE: 54
SGDALPDRYT Y                                                  11

SEQ ID NO: 55          moltype = AA  length = 7
FEATURE                Location/Qualifiers
DOMAIN                 1..7
                       note = Clone GA1#9 VL CDR2
source                 1..7
                       mol_type = protein
                       organism = synthetic construct
SEQUENCE: 55
SDNERPS                                                       7

SEQ ID NO: 56          moltype = AA  length = 8
FEATURE                Location/Qualifiers
DOMAIN                 1..8
                       note = Clone GA1#9 VL CDR3
source                 1..8
                       mol_type = protein
                       organism = synthetic construct
SEQUENCE: 56
QSADPTYT                                                      8

SEQ ID NO: 57          moltype = AA  length = 122
FEATURE                Location/Qualifiers
DOMAIN                 1..122
                       note = Clone GA1#9 VH
source                 1..122
                       mol_type = protein
                       organism = synthetic construct
SEQUENCE: 57
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYYGMD VWGQGTTVTV  120
SS                                                            122

SEQ ID NO: 58          moltype = AA  length = 109
FEATURE                Location/Qualifiers
DOMAIN                 1..109
                       note = Clone GA1#9 VL
source                 1..109
                       mol_type = protein
                       organism = synthetic construct
```

```
SEQUENCE: 58
LSYELTQPPS VSVFPGQTAR ITCSGDALPD RYTYWYQQKP GQAPVLVIYS DNERPSGIPE  60
RFSGSSSGTI ATLTINGVQA EDEADYYCQS ADPTYTFGGG TKLTVLGQP              109

SEQ ID NO: 59          moltype = AA  length = 451
FEATURE                Location/Qualifiers
CHAIN                  1..451
                       note = Clone GA1#9 HC
source                 1..451
                       mol_type = protein
                       organism = synthetic construct
SEQUENCE: 59
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYYGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 60          moltype = AA  length = 212
FEATURE                Location/Qualifiers
CHAIN                  1..212
                       note = Clone GA1#9 LC
source                 1..212
                       mol_type = protein
                       organism = synthetic construct
SEQUENCE: 60
LSYELTQPPS VSVFPGQTAR ITCSGDALPD RYTYWYQQKP GQAPVLVIYS DNERPSGIPE  60
RFSGSSSGTI ATLTINGVQA EDEADYYCQS ADPTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 61          moltype = AA  length = 5
FEATURE                Location/Qualifiers
DOMAIN                 1..5
                       note = Clone GA1#12 VH CDR1
source                 1..5
                       mol_type = protein
                       organism = synthetic construct
SEQUENCE: 61
SYAMH                                                              5

SEQ ID NO: 62          moltype = AA  length = 17
FEATURE                Location/Qualifiers
DOMAIN                 1..17
                       note = Clone GA1#12 VH CDR2
source                 1..17
                       mol_type = protein
                       organism = synthetic construct
SEQUENCE: 62
SISYDGSNKA YADSVKG                                                 17

SEQ ID NO: 63          moltype = AA  length = 13
FEATURE                Location/Qualifiers
DOMAIN                 1..13
                       note = Clone GA1#12 VH CDR3
source                 1..13
                       mol_type = protein
                       organism = synthetic construct
SEQUENCE: 63
DVLRTYYYAG MDV                                                     13

SEQ ID NO: 64          moltype = AA  length = 11
FEATURE                Location/Qualifiers
DOMAIN                 1..11
                       note = Clone GA1#12 VL CDR1
source                 1..11
                       mol_type = protein
                       organism = synthetic construct
SEQUENCE: 64
SGDALPDRYT Y                                                       11

SEQ ID NO: 65          moltype = AA  length = 7
FEATURE                Location/Qualifiers
DOMAIN                 1..7
                       note = Clone GA1#12 VL CDR2
```

```
source                  1..7
                        mol_type = protein
                        organism = synthetic construct
SEQUENCE: 65
LDNERPK                                                                   7

SEQ ID NO: 66           moltype = AA  length = 8
FEATURE                 Location/Qualifiers
DOMAIN                  1..8
                        note = Clone GA1#12 VL CDR3
source                  1..8
                        mol_type = protein
                        organism = synthetic construct
SEQUENCE: 66
QSADDTYT                                                                  8

SEQ ID NO: 67           moltype = AA  length = 122
FEATURE                 Location/Qualifiers
DOMAIN                  1..122
                        note = Clone GA1#12 VH
source                  1..122
                        mol_type = protein
                        organism = synthetic construct
SEQUENCE: 67
QVQLVQSGGG VVQPGRSLRL SCAASGFTFS SYAMHQVRQA PGKGLEWVAS ISYDGSNKAY  60
ADSVKGRFTI SRDNSKNTLY LQMNSLRAED TAVYYCARDV LRTYYYAGMD VWGQGTTVTV  120
SS                                                                  122

SEQ ID NO: 68           moltype = AA  length = 109
FEATURE                 Location/Qualifiers
DOMAIN                  1..109
                        note = Clone GA1#12 VL
source                  1..109
                        mol_type = protein
                        organism = synthetic construct
SEQUENCE: 68
LSYELTQPPS VSVFPGQTAR ITCSGDALPD RYTYWYQQKP GQAPVLVIYL DNERPKGIPE  60
RFSGSSSGTI ATLTINGVQA EDEADYYCQS ADDTYTFGGG TKLTVLGQP              109

SEQ ID NO: 69           moltype = AA  length = 451
FEATURE                 Location/Qualifiers
CHAIN                   1..451
                        note = Clone GA1#12 HC
source                  1..451
                        mol_type = protein
                        organism = synthetic construct
SEQUENCE: 69
QVQLVQSGGG VVQPGRSLRL SCAASGFTFS SYAMHQVRQA PGKGLEWVAS ISYDGSNKAY  60
ADSVKGRFTI SRDNSKNTLY LQMNSLRAED TAVYYCARDV LRTYYYAGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                  451

SEQ ID NO: 70           moltype = AA  length = 212
FEATURE                 Location/Qualifiers
CHAIN                   1..212
                        note = Clone GA1#12 LC
source                  1..212
                        mol_type = protein
                        organism = synthetic construct
SEQUENCE: 70
LSYELTQPPS VSVFPGQTAR ITCSGDALPD RYTYWYQQKP GQAPVLVIYL DNERPKGIPE  60
RFSGSSSGTI ATLTINGVQA EDEADYYCQS ADDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                 212

SEQ ID NO: 71           moltype = AA  length = 452
FEATURE                 Location/Qualifiers
CHAIN                   1..452
                        note = Clone GA1#7K HC
source                  1..452
                        mol_type = protein
                        organism = synthetic construct
SEQUENCE: 71
QVQLVQSGGG VVQPGRSLRL SCAASGFTFS SYAMHQVRQA PGKGLEWVAV ISYDGSQKYY  60
ADSVKGRFTI SRDNSKNTLY LQMNSLRAED TAVYYCARDA LRTYYYYGMD VWGQGTTVTV  120
```

```
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 72           moltype = AA  length = 212
FEATURE                 Location/Qualifiers
CHAIN                   1..212
                        note = Clone GA1#7K LC
source                  1..212
                        mol_type = protein
                        organism = synthetic construct
SEQUENCE: 72
LSYELTQPPS VSVFPGQTAR ITCSGDALPD RYTYWYQQKP GQAPVLVIYS DNERPSGIPE  60
RFSGSSSGTI ATLTINGVQA EDEADYYCQS SDDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 73           moltype = AA  length = 452
FEATURE                 Location/Qualifiers
CHAIN                   1..452
                        note = Clone GA1#7K (LC_FS/IT) HC
source                  1..452
                        mol_type = protein
                        organism = synthetic construct
SEQUENCE: 73
QVQLVQSGGG VVQPGRSLRL SCAASGFTFS SYAMHQVRQA PGKGLEWVAV ISYDGSQKYY  60
ADSVKGRFTI SRDNSKNTLY LQMNSLRAED TAVYYCARDA LRTYYYYGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 74           moltype = AA  length = 212
FEATURE                 Location/Qualifiers
CHAIN                   1..212
                        note = Clone GA1#7K (LC_FS/IT) LC
source                  1..212
                        mol_type = protein
                        organism = synthetic construct
SEQUENCE: 74
LSYELTQPPS VSVSPGQTAR ITCSGDALPD RYTYWYQQKP GQAPVLVIYS DNERPSGIPE  60
RFSGSSSGTT ATLTINGVQA EDEADYYCQS SDDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 75           moltype = AA  length = 451
FEATURE                 Location/Qualifiers
CHAIN                   1..451
                        note = Clone GA1#7 (LC_FS/IT) HC
source                  1..451
                        mol_type = protein
                        organism = synthetic construct
SEQUENCE: 75
QVQLVQSGGG VVQPGRSLRL SCAASGFTFS SYAMHQVRQA PGKGLEWVAV ISYDGSQKYY  60
ADSVKGRFTI SRDNSKNTLY LQMNSLRAED TAVYYCARDA LRTYYYYGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451

SEQ ID NO: 76           moltype = AA  length = 212
FEATURE                 Location/Qualifiers
CHAIN                   1..212
                        note = Clone GA1#7 (LC_FS/IT) LC
source                  1..212
                        mol_type = protein
                        organism = synthetic construct
SEQUENCE: 76
LSYELTQPPS VSVSPGQTAR ITCSGDALPD RYTYWYQQKP GQAPVLVIYS DNERPSGIPE  60
RFSGSSSGTT ATLTINGVQA EDEADYYCQS SDDTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212
```

```
SEQ ID NO: 77          moltype = AA  length = 452
FEATURE                Location/Qualifiers
CHAIN                  1..452
                       note = Clone GA1#8K HC
source                 1..452
                       mol_type = protein
                       organism = synthetic construct
SEQUENCE: 77
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 78          moltype = AA  length = 212
FEATURE                Location/Qualifiers
CHAIN                  1..212
                       note = Clone GA1#8K LC
source                 1..212
                       mol_type = protein
                       organism = synthetic construct
SEQUENCE: 78
LSYELTQPPS VSVFPGQTAR ITCSGDALPD RYTYWYQQKP GQAPVLVIYS DNERPRGIPE  60
RFSGSSSGTI ATLTINGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 79          moltype = AA  length = 452
FEATURE                Location/Qualifiers
CHAIN                  1..452
                       note = Clone GA1#8K (LC_FS/IT) HC
source                 1..452
                       mol_type = protein
                       organism = synthetic construct
SEQUENCE: 79
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 80          moltype = AA  length = 212
FEATURE                Location/Qualifiers
CHAIN                  1..212
                       note = Clone GA1#8K (LC_FS/IT) LC
source                 1..212
                       mol_type = protein
                       organism = synthetic construct
SEQUENCE: 80
LSYELTQPPS VSVSPGQTAR ITCSGDALPD RYTYWYQQKP GQAPVLVIYS DNERPRGIPE  60
RFSGSSSGTT ATLTINGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 81          moltype = AA  length = 451
FEATURE                Location/Qualifiers
CHAIN                  1..451
                       note = Clone GA1#8 (LC_FS/IT) HC
source                 1..451
                       mol_type = protein
                       organism = synthetic construct
SEQUENCE: 81
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP G                                 451
```

```
SEQ ID NO: 82          moltype = AA  length = 212
FEATURE                Location/Qualifiers
CHAIN                  1..212
                       note = Clone GA1#8 (LC_FS/IT) LC
source                 1..212
                       mol_type = protein
                       organism = synthetic construct
SEQUENCE: 82
LSYELTQPPS VSVSPGQTAR ITCSGDALPD RYTYWYQQKP GQAPVLVIYS DNERPRGIPE  60
RFSGSSSGTT ATLTINGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 83          moltype = AA  length = 109
FEATURE                Location/Qualifiers
DOMAIN                 1..109
                       note = Clone GA1#7 (LC_FS/IT) VL
source                 1..109
                       mol_type = protein
                       organism = synthetic construct
SEQUENCE: 83
LSYELTQPPS VSVSPGQTAR ITCSGDALPD RYTYWYQQKP GQAPVLVIYS DNERPSGIPE  60
RFSGSSSGTT ATLTINGVQA EDEADYYCQS SDDTYTFGGG TKLTVLGQP              109

SEQ ID NO: 84          moltype = AA  length = 109
FEATURE                Location/Qualifiers
DOMAIN                 1..109
                       note = Clone GA1#8 (LC_FS/IT) VL
source                 1..109
                       mol_type = protein
                       organism = synthetic construct
SEQUENCE: 84
LSYELTQPPS VSVSPGQTAR ITCSGDALPD RYTYWYQQKP GQAPVLVIYS DNERPRGIPE  60
RFSGSSSGTT ATLTINGVQA EDEADYYCQS ADYTYTFGGG TKLTVLGQP              109

SEQ ID NO: 85          moltype = AA  length = 122
FEATURE                Location/Qualifiers
DOMAIN                 1..122
                       note = Clone GA1#8_14 VH
source                 1..122
                       mol_type = protein
                       organism = synthetic construct
SEQUENCE: 85
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SS                                                                 122

SEQ ID NO: 86          moltype = AA  length = 109
FEATURE                Location/Qualifiers
DOMAIN                 1..109
                       note = Clone GA1#8_14 VL
source                 1..109
                       mol_type = protein
                       organism = synthetic construct
SEQUENCE: 86
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQP              109

SEQ ID NO: 87          moltype = AA  length = 452
FEATURE                Location/Qualifiers
CHAIN                  1..452
                       note = Clone GA1#8_14 HC
source                 1..452
                       mol_type = protein
                       organism = synthetic construct
SEQUENCE: 87
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452
```

```
SEQ ID NO: 88          moltype = AA  length = 212
FEATURE                Location/Qualifiers
CHAIN                  1..212
                       note = Clone GA1#8_14 LC
source                 1..212
                       mol_type = protein
                       organism = synthetic construct
SEQUENCE: 88
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 89          moltype = AA  length = 122
FEATURE                Location/Qualifiers
DOMAIN                 1..122
                       note = Clone GA1#8_17 VH
source                 1..122
                       mol_type = protein
                       organism = synthetic construct
SEQUENCE: 89
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SS                                                                 122

SEQ ID NO: 90          moltype = AA  length = 109
FEATURE                Location/Qualifiers
DOMAIN                 1..109
                       note = Clone GA1#8_17 VL
source                 1..109
                       mol_type = protein
                       organism = synthetic construct
SEQUENCE: 90
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQP              109

SEQ ID NO: 91          moltype = AA  length = 452
FEATURE                Location/Qualifiers
CHAIN                  1..452
                       note = Clone GA1#8_17 HC
source                 1..452
                       mol_type = protein
                       organism = synthetic construct
SEQUENCE: 91
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVKQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 92          moltype = AA  length = 212
FEATURE                Location/Qualifiers
CHAIN                  1..212
                       note = Clone GA1#8_17 LC
source                 1..212
                       mol_type = protein
                       organism = synthetic construct
SEQUENCE: 92
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 93          moltype = AA  length = 122
FEATURE                Location/Qualifiers
DOMAIN                 1..122
                       note = Clone GA1#8_18 VH
source                 1..122
                       mol_type = protein
                       organism = synthetic construct
SEQUENCE: 93
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SS                                                                 122
```

```
SEQ ID NO: 94          moltype = AA  length = 109
FEATURE                Location/Qualifiers
DOMAIN                 1..109
                       note = Clone GA1#8_18 VL
source                 1..109
                       mol_type = protein
                       organism = synthetic construct
SEQUENCE: 94
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQP              109

SEQ ID NO: 95          moltype = AA  length = 452
FEATURE                Location/Qualifiers
CHAIN                  1..452
                       note = Clone GA1#8_18 HC
source                 1..452
                       mol_type = protein
                       organism = synthetic construct
SEQUENCE: 95
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVDQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 96          moltype = AA  length = 212
FEATURE                Location/Qualifiers
CHAIN                  1..212
                       note = Clone GA1#8_18 LC
source                 1..212
                       mol_type = protein
                       organism = synthetic construct
SEQUENCE: 96
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 97          moltype = AA  length = 122
FEATURE                Location/Qualifiers
DOMAIN                 1..122
                       note = Clone GA1#8_20 VH
source                 1..122
                       mol_type = protein
                       organism = synthetic construct
SEQUENCE: 97
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SS                                                                 122

SEQ ID NO: 98          moltype = AA  length = 109
FEATURE                Location/Qualifiers
DOMAIN                 1..109
                       note = Clone GA1#8_20 VL
source                 1..109
                       mol_type = protein
                       organism = synthetic construct
SEQUENCE: 98
LSYELTQPPS VSVFPGQTAR ITCSGDALPD RYTYWYQQKP GQAPVLVIYS DNERPRGIPE  60
RFSGSSSGTT ATLTINGVQA EDEADYYCQS ADYTYTFGGG TKLTVLGQP              109

SEQ ID NO: 99          moltype = AA  length = 452
FEATURE                Location/Qualifiers
CHAIN                  1..452
                       note = Clone GA1#8_20 HC
source                 1..452
                       mol_type = protein
                       organism = synthetic construct
SEQUENCE: 99
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFPAVKQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
```

```
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 100          moltype = AA  length = 212
FEATURE                 Location/Qualifiers
CHAIN                   1..212
                        note = Clone GA1#8_20 LC
source                  1..212
                        mol_type = protein
                        organism = synthetic construct
SEQUENCE: 100
LSYELTQPPS VSVFPGQTAR ITCSGDALPD RYTYWYQQKP GQAPVLVIYS DNERPRGIPE  60
RFSGSSSGTT ATLTINGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSKLSL  180
TPEQWKSHKS YSCQVTHEGS TVEKTVAPTE CS                                212

SEQ ID NO: 101          moltype = AA  length = 122
FEATURE                 Location/Qualifiers
DOMAIN                  1..122
                        note = Clone GA1#8_21 VH
source                  1..122
                        mol_type = protein
                        organism = synthetic construct
SEQUENCE: 101
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SS                                                                 122

SEQ ID NO: 102          moltype = AA  length = 109
FEATURE                 Location/Qualifiers
DOMAIN                  1..109
                        note = Clone GA1#8_21 VL
source                  1..109
                        mol_type = protein
                        organism = synthetic construct
SEQUENCE: 102
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQP              109

SEQ ID NO: 103          moltype = AA  length = 452
FEATURE                 Location/Qualifiers
CHAIN                   1..452
                        note = Clone GA1#8_21 HC
source                  1..452
                        mol_type = protein
                        organism = synthetic construct
SEQUENCE: 103
QVQLVQSGGG VVQPGRSLRL SCAASGFTFS SYAMHQVRQA PGKGLEWVAS ISYDGSNKYY  60
ADSVKGRFTI SRDNSKNTLY LQMNSLRAED TAVYYCARDA LRTYYYQGMD VWGQGTTVTV  120
SSASTKGPSV FPLAPSSKST SGGTAALGCL VKDYFPEPVT VSWNSGALTS GVHTFKAVKQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 104          moltype = AA  length = 212
FEATURE                 Location/Qualifiers
CHAIN                   1..212
                        note = Clone GA1#8_21 LC
source                  1..212
                        mol_type = protein
                        organism = synthetic construct
SEQUENCE: 104
LSYELTQPPS VSVSPGQTAR ITCSGDALPD RYTYWYQQKP GQAPVLVIYS DNERPRGIPE  60
RFSGSSSGTT ATLTITGVQA EDEADYYCQS ADYTYTFGGG TKLTVLGQPK AAPSVTLFPP  120
SSEELQANKA TLVCLISDFY PGAVTVAWKA DSSPVKAGVE TTTPSKQSNN KYAASSYLSL  180
TPEQWKSHKS YSCQVTHEGS TVEKTVAPTE CS                                212

SEQ ID NO: 105          moltype = AA  length = 5
FEATURE                 Location/Qualifiers
DOMAIN                  1..5
                        note = Clone hGA17 VH CDR1
source                  1..5
                        mol_type = protein
                        organism = synthetic construct
SEQUENCE: 105
DTYFH                                                              5
```

-continued

```
SEQ ID NO: 106          moltype = AA  length = 17
FEATURE                 Location/Qualifiers
DOMAIN                  1..17
                        note = Clone hGA17 VH CDR2
source                  1..17
                        mol_type = protein
                        organism = synthetic construct
SEQUENCE: 106
RIDPTNGNGR YAQKFQG                                                17

SEQ ID NO: 107          moltype = AA  length = 11
FEATURE                 Location/Qualifiers
DOMAIN                  1..11
                        note = Clone hGA17 VH CDR3
source                  1..11
                        mol_type = protein
                        organism = synthetic construct
SEQUENCE: 107
STGTGYFALV Y                                                      11

SEQ ID NO: 108          moltype = AA  length = 11
FEATURE                 Location/Qualifiers
DOMAIN                  1..11
                        note = Clone hGA17 VL CDR1
source                  1..11
                        mol_type = protein
                        organism = synthetic construct
SEQUENCE: 108
KASQNVGSAV A                                                      11

SEQ ID NO: 109          moltype = AA  length = 7
FEATURE                 Location/Qualifiers
DOMAIN                  1..7
                        note = Clone hGA17 VL CDR2
source                  1..7
                        mol_type = protein
                        organism = synthetic construct
SEQUENCE: 109
WSSTRHT                                                           7

SEQ ID NO: 110          moltype = AA  length = 10
FEATURE                 Location/Qualifiers
DOMAIN                  1..10
                        note = Clone hGA17 VL CDR3
source                  1..10
                        mol_type = protein
                        organism = synthetic construct
SEQUENCE: 110
QQYSNYPLTF                                                        10

SEQ ID NO: 111          moltype = AA  length = 120
FEATURE                 Location/Qualifiers
DOMAIN                  1..120
                        note = Clone hGA17 VH
source                  1..120
                        mol_type = protein
                        organism = synthetic construct
SEQUENCE: 111
QVQLVQSGAE VKKPGASVKV SCKASGFNIK DTYFHWVRQA PGQGLEWMGR IDPTNGNGRY  60
AQKFQGRVTM TRDTSTSTVY MELSSLRSED TAVYYCATST GTGYFALVYW GQGTTVTVSS  120

SEQ ID NO: 112          moltype = AA  length = 110
FEATURE                 Location/Qualifiers
DOMAIN                  1..110
                        note = Clone hGA17 VL
source                  1..110
                        mol_type = protein
                        organism = synthetic construct
SEQUENCE: 112
DIQLTQSPSF LSASVGDRVT ITCKASQNVG SAVAWYQQKP GKAPKLLIYW SSTRHTGVPS  60
RFSGSGSGTE FTLTISSLQP EDFATYYCQQ YSNYPLTFGG GTKLEIKRTV            110

SEQ ID NO: 113          moltype = AA  length = 450
FEATURE                 Location/Qualifiers
CHAIN                   1..450
                        note = Clone hGA17 HC
source                  1..450
                        mol_type = protein
                        organism = synthetic construct
```

-continued

```
SEQUENCE: 113
QVQLVQSGAE VKKPGASVKV SCKASGFNIK DTYFHWVRQA PGQGLEWMGR IDPTNGNGRY  60
AQKFQGRVTM TRDTSTSTVY MELSSLRSED TAVYYCATST GTGYFALVYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                 450

SEQ ID NO: 114         moltype = AA  length = 214
FEATURE                Location/Qualifiers
CHAIN                  1..214
                       note = Clone hGA17 LC
source                 1..214
                       mol_type = protein
                       organism = synthetic construct
SEQUENCE: 114
DIQLTQSPSF LSASVGDRVT ITCKASQNVG SAVAWYQQKP GKAPKLLIYW SSTRHTGVPS  60
RFSGSGSGTE FTLTISSLQP EDFATYYCQQ YSNYPLTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 115         moltype = AA  length = 662
FEATURE                Location/Qualifiers
PEPTIDE                1..662
                       note = GARP polypeptide
source                 1..662
                       mol_type = protein
                       organism = synthetic construct
SEQUENCE: 115
MRPQILLLLA LLTLGLAAQH QDKVPCKMVD KKVSCQVLGL LQVPSVLPPD TETLDLSGNQ  60
LRSILASPLG FYTALRHLDL STNEISFLQP GAFQALTHLE HLSLAHNRLA MATALSAGGL  120
GPLPRVTSLD LSGNSLYSGL LERLLGEAPS LHTLSLAENS LTRLTRHTFR DMPALEQLDL  180
HSNVLMDIED GAFEGLPRLT HLNLSRNSLT CISDFSLQQL RVLDLSCNSI EAFQTASQPQ  240
AEFQLTWLDL RENKLLHFPD LAALPRLIYL NLSNNLIRLP TGPPQDSKGI HAPSEGWSAL  300
PLSAPSGNAS GRPLSQLLNL DLSYNEIELI PDSFLEHLTS LCFLNLSRNC LRTFEARRLG  360
SLPCLMLLDL SHNALETLEL GARALGSLRT LLLQGNALRD LPPYTFANLA SLQRLNLQGN  420
RVSPCGGPDE PGPSGCVAFS GITSLRSLSL VDNEIELLRA GAFLHTPLTE LDLSSNPGLE  480
VATGALGGLE ASLEVLALQG NGLMVLQVDL PCFICLKRLN LAENRLSHLP AWTQAVSLEV  540
LDLRNNSFSL LPGSAMGGLE TSLRRLYLQG NPLSCCGNGW LAAQLHQGRV DVDATQDLIC  600
RFSSQEEVSL SHVRPEDCEK GGLKNINLII ILTFILVSAI LLTTLAACCC VRRQKFNQQY  660
KA                                                               662

SEQ ID NO: 116         moltype = AA  length = 608
FEATURE                Location/Qualifiers
DOMAIN                 1..608
                       note = GARP polypeptide extracellular domain (ECD)
source                 1..608
                       mol_type = protein
                       organism = synthetic construct
SEQUENCE: 116
HQDKVPCKMV DKKVSCQVLG LLQVPSVLPP DTETLDLSGN QLRSILASPL GFYTALRHLD  60
LSTNEISFLQ PGAFQALTHL EHLSLAHNRL AMATALSAGG LGPLPRVTSL DLSGNSLYSG  120
LLERLLGEAP SLHTLSLAEN SLTRLTRHTF RDMPALEQLD LHSNVLMDIE DGAFEGLPRL  180
THLNLSRNSL TCISDFSLQQ LRVLDLSCNS IEAFQTASQP QAEFQLTWLD LRENKLLHFP  240
DLAALPRLIY LNLSNNLIRL PTGPPQDSKG IHAPSEGWSA LPLSAPSGNA SGRPLSQLLN  300
LDLSYNEIEL IPDSFLEHLT SLCFLNLSRN CLRTFEARRL GSLPCLMLLD LSHNALETLE  360
LGARALGSLR TLLLQGNALR DLPPYTFANL ASLQRLNLQG NRVSPCGGPD EPGPSGCVAF  420
SGITSLRSLS LVDNEIELLR AGAFLHTPLT ELDLSSNPGL EVATGALGGL EASLEVLALQ  480
GNGLMVLQVD LPCFICLKRL NLAENRLSHL PAWTQAVSLE VLDLRNNSFS LLPGSAMGGL  540
ETSLRRLYLQ GNPLSCCGNG WLAAQLHQGR VDVDATQDLI CRFSSQEEVS LSHVRPEDCE  600
KGGLKNIN                                                         608

SEQ ID NO: 117         moltype = AA  length = 5
FEATURE                Location/Qualifiers
DOMAIN                 1..5
                       note = 117Exemplary linker
source                 1..5
                       mol_type = protein
                       organism = synthetic construct
SEQUENCE: 117
GGGGS                                                            5

SEQ ID NO: 118         moltype = AA  length = 12
FEATURE                Location/Qualifiers
DOMAIN                 1..12
                       note = 118Exemplary linker
```

```
source                  1..12
                        mol_type = protein
                        organism = synthetic construct
SEQUENCE: 118
GSGGSGGSGG SG                                                12

SEQ ID NO: 119          moltype = AA  length = 15
FEATURE                 Location/Qualifiers
DOMAIN                  1..15
                        note = 119Exemplary linker
source                  1..15
                        mol_type = protein
                        organism = synthetic construct
SEQUENCE: 119
GGGGSGGGGS GGGGS                                             15

SEQ ID NO: 120          moltype = AA  length = 5
FEATURE                 Location/Qualifiers
DOMAIN                  1..5
                        note = 120Exemplary linker
source                  1..5
                        mol_type = protein
                        organism = synthetic construct
SEQUENCE: 120
GGGSG                                                        5

SEQ ID NO: 121          moltype = AA  length = 10
FEATURE                 Location/Qualifiers
DOMAIN                  1..10
                        note = 121Exemplary linker
source                  1..10
                        mol_type = protein
                        organism = synthetic construct
SEQUENCE: 121
GGGSGGGGSG                                                   10

SEQ ID NO: 122          moltype = AA  length = 8
FEATURE                 Location/Qualifiers
DOMAIN                  1..8
                        note = 122Exemplary linker
source                  1..8
                        mol_type = protein
                        organism = synthetic construct
SEQUENCE: 122
GGSGGGSG                                                     8

SEQ ID NO: 123          moltype = AA  length = 12
FEATURE                 Location/Qualifiers
DOMAIN                  1..12
                        note = 123Exemplary linker
source                  1..12
                        mol_type = protein
                        organism = synthetic construct
SEQUENCE: 123
GGSGGGSGGG SG                                                12

SEQ ID NO: 124          moltype = AA  length = 6
FEATURE                 Location/Qualifiers
DOMAIN                  1..6
                        note = 124Exemplary linker
source                  1..6
                        mol_type = protein
                        organism = synthetic construct
SEQUENCE: 124
GSGGSG                                                       6

SEQ ID NO: 125          moltype = AA  length = 9
FEATURE                 Location/Qualifiers
DOMAIN                  1..9
                        note = 125Exemplary linker
source                  1..9
                        mol_type = protein
                        organism = synthetic construct
SEQUENCE: 125
GSGGSGGSG                                                    9

SEQ ID NO: 126          moltype = AA  length = 7
FEATURE                 Location/Qualifiers
DOMAIN                  1..7
```

```
                        note = 126Exemplary linker
source                  1..7
                        mol_type = protein
                        organism = synthetic construct
SEQUENCE: 126
GSGSGSG                                                                7

SEQ ID NO: 127          moltype = AA  length = 21
FEATURE                 Location/Qualifiers
DOMAIN                  1..21
                        note = 127Exemplary linker
source                  1..21
                        mol_type = protein
                        organism = synthetic construct
SEQUENCE: 127
GGGGSGGGGS GGGGSGGGGS G                                                21

SEQ ID NO: 128          moltype = AA  length = 5
FEATURE                 Location/Qualifiers
DOMAIN                  1..5
                        note = 128Exemplary linker
source                  1..5
                        mol_type = protein
                        organism = synthetic construct
SEQUENCE: 128
PAPAP                                                                  5

SEQ ID NO: 129          moltype = AA  length = 15
FEATURE                 Location/Qualifiers
DOMAIN                  1..15
                        note = 129Exemplary linker
source                  1..15
                        mol_type = protein
                        organism = synthetic construct
SEQUENCE: 129
PAPAPPAPAP PAPAP                                                       15

SEQ ID NO: 130          moltype = AA  length = 7
FEATURE                 Location/Qualifiers
DOMAIN                  1..7
                        note = 130Exemplary linker
source                  1..7
                        mol_type = protein
                        organism = synthetic construct
SEQUENCE: 130
IKRTVAA                                                                7

SEQ ID NO: 131          moltype = AA  length = 7
FEATURE                 Location/Qualifiers
DOMAIN                  1..7
                        note = 131Exemplary linker
source                  1..7
                        mol_type = protein
                        organism = synthetic construct
SEQUENCE: 131
VSSASTK                                                                7

SEQ ID NO: 132          moltype = AA  length = 4
FEATURE                 Location/Qualifiers
DOMAIN                  1..4
                        note = 132Exemplary linker
source                  1..4
                        mol_type = protein
                        organism = synthetic construct
SEQUENCE: 132
ASTK                                                                   4

SEQ ID NO: 133          moltype = AA  length = 12
FEATURE                 Location/Qualifiers
DOMAIN                  1..12
                        note = 133Exemplary linker
source                  1..12
                        mol_type = protein
                        organism = synthetic construct
SEQUENCE: 133
ASTKSGGSGG SG                                                          12

SEQ ID NO: 134          moltype = AA  length = 7
FEATURE                 Location/Qualifiers
```

```
DOMAIN                  1..7
                        note = 134Exemplary linker
source                  1..7
                        mol_type = protein
                        organism = synthetic construct
SEQUENCE: 134
AEAAAKA                                                             7

SEQ ID NO: 135          moltype = AA  length = 12
FEATURE                 Location/Qualifiers
DOMAIN                  1..12
                        note = 135Exemplary linker
source                  1..12
                        mol_type = protein
                        organism = synthetic construct
SEQUENCE: 135
AEAAAKEAAA KA                                                       12

SEQ ID NO: 136          moltype = AA  length = 10
FEATURE                 Location/Qualifiers
DOMAIN                  1..10
                        note = 136Exemplary linker
source                  1..10
                        mol_type = protein
                        organism = synthetic construct
SEQUENCE: 136
GRPGSGRPGS                                                          10

SEQ ID NO: 137          moltype = AA  length = 20
FEATURE                 Location/Qualifiers
DOMAIN                  1..20
                        note = 137Exemplary linker
source                  1..20
                        mol_type = protein
                        organism = synthetic construct
SEQUENCE: 137
GRPGSGRPGS GRPGSGRPGS                                               20

SEQ ID NO: 138          moltype = AA  length = 10
FEATURE                 Location/Qualifiers
DOMAIN                  1..10
                        note = 138Exemplary linker
source                  1..10
                        mol_type = protein
                        organism = synthetic construct
SEQUENCE: 138
GRGGSGRGGS                                                          10

SEQ ID NO: 139          moltype = AA  length = 20
FEATURE                 Location/Qualifiers
DOMAIN                  1..20
                        note = 139Exemplary linker
source                  1..20
                        mol_type = protein
                        organism = synthetic construct
SEQUENCE: 139
GRGGSGRGGS GRGGSGRGGS                                               20

SEQ ID NO: 140          moltype = AA  length = 10
FEATURE                 Location/Qualifiers
DOMAIN                  1..10
                        note = 140Exemplary linker
source                  1..10
                        mol_type = protein
                        organism = synthetic construct
SEQUENCE: 140
GKPGSGKPGS                                                          10

SEQ ID NO: 141          moltype = AA  length = 20
FEATURE                 Location/Qualifiers
DOMAIN                  1..20
                        note = 141Exemplary linker
source                  1..20
                        mol_type = protein
                        organism = synthetic construct
SEQUENCE: 141
GKPGSGKPGS GKPGSGKPGS                                               20

SEQ ID NO: 142          moltype = AA  length = 10
```

-continued

```
FEATURE                Location/Qualifiers
DOMAIN                 1..10
                       note = 142Exemplary linker
source                 1..10
                       mol_type = protein
                       organism = synthetic construct
SEQUENCE: 142
GEPGSGEPGS                                                          10

SEQ ID NO: 143         moltype = AA  length = 20
FEATURE                Location/Qualifiers
DOMAIN                 1..20
                       note = 143Exemplary linker
source                 1..20
                       mol_type = protein
                       organism = synthetic construct
SEQUENCE: 143
GEGGSGEGGS GEGGSGEGGS                                               20

SEQ ID NO: 144         moltype = AA  length = 10
FEATURE                Location/Qualifiers
DOMAIN                 1..10
                       note = 144Exemplary linker
source                 1..10
                       mol_type = protein
                       organism = synthetic construct
SEQUENCE: 144
GDPGSGDPGS                                                          10

SEQ ID NO: 145         moltype = AA  length = 20
FEATURE                Location/Qualifiers
DOMAIN                 1..20
                       note = 145Exemplary linker
source                 1..20
                       mol_type = protein
                       organism = synthetic construct
SEQUENCE: 145
GDPGSGDPGS GDPGSGDPGS                                               20
```